United States Patent
Perez et al.

(10) Patent No.: US 7,939,278 B2
(45) Date of Patent: May 10, 2011

(54) METHODS AND COMPOSITIONS FOR RISK STRATIFICATION

(75) Inventors: Omar D. Perez, San Francisco, CA (US); Garry P. Nolan, San Francisco, CA (US); Jonathan M. Irish, Palo Alto, CA (US)

(73) Assignee: The Board of Trustees of Leland Stanford Junior University, Palo Alto, CA (US)

( * ) Notice: Subject to any disclaimer, the term of this patent is extended or adjusted under 35 U.S.C. 154(b) by 427 days.

(21) Appl. No.: 12/016,174

(22) Filed: Jan. 17, 2008

(65) Prior Publication Data

US 2008/0182262 A1     Jul. 31, 2008

Related U.S. Application Data

(62) Division of application No. 10/898,734, filed on Jul. 21, 2004, now Pat. No. 7,393,656.

(51) Int. Cl.
*G01N 33/567* (2006.01)

(52) U.S. Cl. .................... 435/7.21; 435/2; 435/4; 435/6; 435/7.23; 435/7.24; 435/40.51; 435/375; 435/287.2; 435/973; 436/546; 436/10; 436/56; 436/63; 436/64; 436/172; 436/174; 422/82.09

(58) Field of Classification Search .................. 435/2, 4, 435/7.1, 7.21, 7.23, 7.24, 7.4, 7.92, 8, 18, 435/23, 40.5, 375, 973, 287.2; 436/503, 436/519, 538, 546, 10, 17, 37, 56, 63, 64, 436/172, 174; 422/82.09

See application file for complete search history.

(56) References Cited

U.S. PATENT DOCUMENTS

| | | | |
|---|---|---|---|
| 4,979,824 A | 12/1990 | Mathies et al. | |
| 5,137,809 A | 8/1992 | Loken et al. | |
| 5,919,646 A | 7/1999 | Okun et al. | |
| 5,968,738 A | 10/1999 | Anderson et al. | |
| 6,280,967 B1 | 8/2001 | Ransom et al. | |
| 6,379,917 B1 | 4/2002 | Okun et al. | |
| 6,558,916 B2 | 5/2003 | Veerapandian et al. | |
| 6,673,554 B1 * | 1/2004 | Kauvar | 435/7.1 |
| 6,821,740 B2 | 11/2004 | Darzynkiewicz et al. | |

(Continued)

FOREIGN PATENT DOCUMENTS

WO     03/067210     8/2003

OTHER PUBLICATIONS

Krutzik et al., Analysis of protein phosphorylation and cellular signaling events by flow cytometry: techniques and clinical applications, Clinical Immunology 110: 206-221 (Mar. 2004).*

(Continued)

*Primary Examiner* — Gailene R Gabel

(74) *Attorney, Agent, or Firm* — David C. Scherer; Bozicevic, Field & Francis LLP

(57) ABSTRACT

The present invention provides an approach for the simultaneous determination of the activation states of a plurality of proteins in single cells. This approach permits the rapid detection of heterogeneity in a complex cell population based on activation states, and the identification of cellular subsets that exhibit correlated changes in activation within the cell population. Moreover, this approach allows the correlation of cellular activities or properties. In addition, the use of potentiators of cellular activation allows for characterization of such pathways and cell populations.

29 Claims, 14 Drawing Sheets

U.S. PATENT DOCUMENTS

| | | | |
|---|---|---|---|
| 6,958,221 B2 | 10/2005 | Veerapandian et al. | |
| 7,070,943 B2 | 7/2006 | Darzynkiewicz et al. | |
| 7,183,385 B2 | 2/2007 | Comb et al. | |
| 7,236,888 B2 | 6/2007 | Albritton et al. | |
| 7,326,577 B2 | 2/2008 | Shults et al. | |
| 7,393,656 B2 * | 7/2008 | Perez et al. | 435/7.21 |
| 2002/0197658 A1 | 12/2002 | Delaney et al. | |
| 2003/0190688 A1 | 10/2003 | Crosby et al. | |
| 2003/0190689 A1 | 10/2003 | Crosby et al. | |
| 2004/0063088 A1 | 4/2004 | Berg et al. | |
| 2004/0072184 A1 | 4/2004 | Yoganathan et al. | |
| 2004/0106156 A1 | 6/2004 | Perez et al. | |
| 2004/0126784 A1 | 7/2004 | Hitoshi et al. | |
| 2004/0137539 A1 | 7/2004 | Bradford | |
| 2004/0170995 A1 | 9/2004 | Lograsso et al. | |
| 2004/0180380 A1 | 9/2004 | Lee et al. | |
| 2004/0219592 A1 | 11/2004 | Berg et al. | |
| 2004/0224371 A1 | 11/2004 | DeMatos et al. | |
| 2004/0229284 A1 | 11/2004 | Luciw et al. | |
| 2004/0241636 A1 | 12/2004 | Michnick et al. | |
| 2004/0248151 A1 | 12/2004 | Bacus et al. | |
| 2005/0009112 A1 | 1/2005 | Edgar et al. | |
| 2005/0074834 A1 | 4/2005 | Chaplen et al. | |
| 2005/0131006 A1 | 6/2005 | Mukherjee et al. | |
| 2005/0216961 A1 | 9/2005 | Delaney | |
| 2005/0250127 A1 | 11/2005 | Fisher et al. | |
| 2005/0281743 A1 | 12/2005 | Delaney | |
| 2006/0029944 A1 | 2/2006 | Huang et al. | |
| 2006/0035211 A1 | 2/2006 | Levinson et al. | |
| 2006/0040338 A1 | 2/2006 | Westwick et al. | |
| 2006/0046249 A1 | 3/2006 | Huang et al. | |
| 2006/0073474 A1 | 4/2006 | Perez et al. | |

OTHER PUBLICATIONS

Allende, L. M., et al.. (2000). "A novel CD18 genomic deletion in a patient with severe leucocyte adhesion deficiency: a possible CD2Aymphocyte function-associated antigen-1 functional association in humans." Immunology, 99:440-50.

Anderson, M. T. et al. (1996). "Simultaneous fluorescence-activated cell sorter analysis of two distinct transcriptional elements within a single cell using engineered green fluorescent proteins." Proc Natl Acad Sci USA 93,8508-11.

Belloc et al. "Flow Cytometry Detection of Caspase 3 Activation in Preapoptic Leukemic Cells," Cytometry (2000) 41:151-160.

Bleijs, D. A., et al. (2001). "A single amino acid in the cytoplasmic domain of the beta 2 integrin lymphocyte function-associated antigen-1 regulates avidity-dependent inside-out signaling." J Biol Chem 276, 10338-10346.

Calo et al. "STAT Proteins; From Normal Control of Cellular Events to Tumorigenesis," Journal of Cellular Physiology (2003) 197:157-168.

Castillo et al. "Proliferative Response of Mantle Cell Lymphoma Cells Stimulated by CD40 Ligation and IL-4," Leukemia (2000) 14:292-298.

Chow et al., "Measurement of MAP Kinase Activation in Flow Cytometry Using Phospho-Specific Antibodies to MEK and ERK: Potential for Pharmacodynamic Monitoring of Signal Transduction Inhibitors", Cytometry (Comms. In Clinical Cytometry) 46:72-78 (May 2001).

Colucci, F., et al. (1999). "Redundant role of the Syk protein tyrosine kinase in mouse NK cell differentiation." J Immunol163,1769-1774.

Damle, N. K., et al. (1992c). "Differential regulatory effects of intercellular adhesion molecule-1 on costimulation by the CD28 counter-receptor B7." J Immunol 149, 2541-2548.

Dantuma, N. P., et al. "Short-lived green fluorescent proteins for quantifying ubiquitin/proteasome-dependent proteolysis in living cells." Nat Biotechnol 18, 538-43. (2000).

Davis, K. A., et al. (1998). Determination of CD4 antigen density on cells: role of antibody valency, avidity, clones, and conjugation. Cytometry 33,197-205.

De Fougerolles, A. R., et al. (1995). "Heterogenous glycosylation of ICAM-3 and lack of interaction with Mac-1 and p150,95." Eur J Immunol 25,1008-12.

De Fougerolles, et al. (1991). "Characterization of ICAM-2 and evidence for a third counter-receptor for LFA-1." J Exp Med 174,253-67.

De Rosa. S. C., et al. "11-color, 13-parameter flow cytometry: Identification of human naive T cells by phenotype, function, and T-cell receptor diversity." Nat Med 7, 245-248. (2001).

Deeths, M. J., and Mescher, M. F. (1999). "ICAM-1 and 87-1 provide similar but distinct costimulation for CD8+ T cells, while CD4+ T cells are poorly costimulated by ICAM-1." Eur J Immunol 29, 45-53.

Devine, L., et al. "Role of LFA-1, ICAM-1, VLA4 and VCAM-1 in lymphocyte migration across retinal pigment epithelial monolayers in vitro." Immunology 88, 456-62. (1996).

Diacovo, T. G., et al. (1994). "A functional integrin ligand on the surface of platelets: intercellular adhesion molecule-2." J Clin Invest 94.1243-51.

Dikic. I., et al. (1996). "A role for Pyk2 and Src in linking G-protein-coupled receptors with MAP kinase activation." Nature 383, 547-50.

Donskov, F., et al. (1996). "Expression and function of LFA-1 on A-NK and T-LAK cells: role in tumor target killing and migration into tumor tissue." Nat Immun 15,134-146.

Erlanson et al. "Flow Cytometric Quantification of Cyclin E in Human Cell Lines and Hematopoietic Malignancies," Cytometry (1998) 32:214-222.

Fiering, S. N. et al. "Improved FAGS-Gal: flow cytometric analysis and sorting of viable eukaryotic cells expressing reporter gene constructs." Cytometry 12, 291-301. (1991).

Fine, J. S., and Kruisbeek, A. M. (1991). "The role of LFA-I/ICAM-1 interactions during murine T lymphocyte development." J Immunol 147, 2852-2859.

Geiger, C., et al. (2000). "Cytohesin-1 regulates beta-2 integrin-mediated adhesion through both ARF-GEF function and interaction with LFA-1." Embo J 19,2525-2536.

Griffioen, A. W., et al. (1996). "Endothelial intercellular adhesion molecule-1 expression is suppressed in human malignancies: the role of angiogenic factors." Cancer Res 56, 111 1-17.

Griffioen, A. W., et al. (1996). "Tumor angiogenesis is accompanied by a decreased inflammatory response of tumor-associated endothelium." Blood 88, 667-73.

Helander, T. S., et al. (1996). "ICAM-2 redistributed by ezrin as a target for killer cells." Nature 382, 265-8.

Hogg N., et al. (1999). "A novel leukocyte adhesion deficiency caused by expressed but nonfunctional beta2 integrins Mac-1 and LFA-1." J Clin Invest 103, 97-106.

Igietseme, J. U., et al. (1999). "The intercellular adhesion molecule type-1 is required for rapid activation of T helper type 1 lymphocytes that control early acute phase of genital chlamydial infection in mice." Immunology 98, 510-8.

Irish et al. "Single Cell Profiling of Potentiated Phospho-Protein Networks in Cancer Cells," Cell (2004) 118:217-228.

Iyer, S. B., et al. (1998). Quantitation of CD38 expression.using QuantiBRITE™ beads. Cytometry 33, 206-12.

Jiang, K., et al. (2000). "Pivotal role of phosphoinositide-3 kinase in regulation of cytotoxicity in natural killer cells." Nat Immunol 1, 419-425.

Johnson, V. L., et al. (2000). "Effector caspases are dispensable for the early nudear morphological changes during chemical-induced apoptosis." J Cell Sci 113, 2941-53.

Kennedy, S. G., et al. (1999). "Akt/Protein kinase B inhibits cell death by preventing the release of cytochrome c from mitochondria." Mol Cell Biol 19, 5800-10.

Kliche. S., et al. (2001). "Signaling by human herpesvirus 8 kaposin A through direct membrane recruitment of cytohesin-1." Mol Cell 7, 833-843.

Krutzik et al. "Analysis of Protein Phosphorylation and Cellular Signaling Events by Flow Cytometry: Techniques and Clinical Applications," Clinical Immunology (2004) 110:206-221.

Krutzik et al. "Intracellular Phospho-protein Staining Techniques for Flow Cytometry: Monitoring Single Cell Signaling Events," Cytometry Part A (2005) 55A:61-70.

Kulik, G. et al. (1997). "Antiapoptotic signalling by the insulin-like growth factor I receptor, phosphatidylinositol 3-kinase, and Akt." Mol Cell Biol 17, 1595-606.

Lecoeur, H., et al. (2001). "A novel flow cytometric assay for quantitation and multiparametric characterization of cell-mediated cytotoxicity." J Immunol Methods 253, 177-187.

Lenkei, R., et al. (1998). "Performance of calibration standards for antigen quantitation with flow cytometry." Cytometry 33, 188-96.

Lub, M., et al. (1997). "Dual role of the actin cytoskeleton in regulating cell adhesion mediated by the integrin lymphocyte function-associated molecule-1 ." Mol Biol Cell 8, 341-351.

Matsumoto, G., et al. (2000). "Adhesion mediated by LFA-1 is required for efficient IL-12-induced NK and NKT cell cytotoxicity." Eur J Immunol 30, 3723-3731.

McDowall. A., et al. (1998). "The I domain of integrin leukocyte function-associated antigen-I is involved in a conformational change leading to high affinity binding to ligand intercellular adhesion molecule 1 (ICAM-1)." J Biol Chem 273, 27396-27403.

Miller, J., et al. (1995). "Intercellular adhesion molecule-1 dimerization and its consequences for adhesion mediated by lymphocyte function associated-1." J Exp Med 182,1231-41.

Morgan et al., "Cell-cycle-dependent activation of mitogen-activated protein kinase kinase (MEK-½) in myeloid leukemia cell lines and induction of growth inhibition and apoptosis by inhibitors of RAS signaling", Neoplasia, Mar. 15, 2001, vol. 97, No. 6, pp. 1823-1834.

Morgan, M. M., et al. (2001). "Superantigen-induced T cell:B cell conjugation is mediated by LFA-1 and requires signaling through Lck, but not ZAP-70." J Immunol 167, 5708-5718.

Morkve et al. "Quantitation of Biological Tumor Markers (p53, c-myc, Ki-67 and DNA Ploidy) By Multiparameter Flow Cytometry in Non-Small-Cell Lung Cancer," Int. J. Cancer (1992) 52:851-855.

Moser, C., et al. (2002). "Improved outcome of chronic *Pseudomonas aeruginosa* lung infection is associated with induction of a Th1-dominated cytokine response." Clin Exp Immunol 127, 206-213.

Mukai, S., et al. (1999). "Critical role of CD11a (LFA-1) in therapeutic efficacy of systemically transferred antitumor effector T cells." Cell Immunol 192, 122-132.

Neeson, P. J., et al. (2000). "Characterization of activated lymphocyte-tumor cell adhesion." J Leukoc Biol 67, 847-855.

Nielsen, S. D., et al. "Expression of the activation antigen CD69 predicts functionality of in vitro expanded peripheral blood mononuclear cells (PBMC) from healthy donors and HIV-infected patients." Clin Exp Immunol 114, 66-72. (1998).

Nishimura, T., et al. (1999). "Distinct role of antigen-specific T helper type 1 (Th1) and Th2 cells in tumor eradication in vivo." J Exp Med 190, 617-627.

Nolan, G. P., et al. "Fluorescence activated cell analysis and sorting of viable mammalian cells based on beta-D-galactosidase activity after transduction of *Escherichia coli* lacZ." Proc Natl Acad Sci USA 85, 2603-7. (1988).

Nolan, Garry; et al., "Methods for determining kinase activity", U.S. Appl. No. 60/310,141, filed Aug. 2, 2001.

Olsen, M. J. et al. "Function-based isolation of novel enzymes from a large library." Nat Biotechnol 18, 10714.

Onishi, M., et al. (1996). "Applications of retrovirus-mediated expression cloning." Exp Hemato 124, 324-9.

Perez et al. "Flow Cytometric Analysis of Kinase Signaling Cascades," Methods in Molecular Biology (2004) 263:67-94.

Perez et al. "LFA-1 Signaling Through p44/42 is Coupled to Perform Degranulation in CD56+CD8+ Natural Killer Cells," Blood (2004) 104(4):1083-1093.

Perez O. D., et. al., "Leukocyte functional antigen 1 lowers T cell activation thresholds and signaling through cytohesin-1 and Jun-activating binding protein 1". Nature Immunology. Nov. 2003;4(11):1083-92.

Perez, O. D., and Nolan, G. P. (2002). "Simultaneous measurement of multiple active kinase states using polychromatic flow cytometry." Nat Biotechnol 20, 155-62.

Perez, O. D., et al;. (2002). "Activation of the PKBIAKT Pathway by ICAM-2." Immunity 16, 51-65.

Perez, Omar; et al., "Methods for the simultaneous determination of the activation state of multiple proteins", U.S. Appl. No. 60/304,434, filed Jul. 10, 2001.

Peterson, E. J., et al. (2001). "Coupling of the TCR to integrin activation by Slap-130/Fyb." Science 293, 2263-2265.

Radoja, S., et al. (2001). "CD8+ tumor-infiltrating T cells are deficient in perforin-mediated cytolytic activity due to defective microtubule-organizing center mobilization and lytic granule exocytosis." J Immunol 167, 5042-5051.

Risso. A. et al. "CD69 in resting and activated T lymphocytes. Its association with a GTP binding protein and biochemical requirements for its expression." J Immunol 146, 4105-14. (1991).

Salomon, B., and Bluestone, J. A. (1998). "LFA-1 interaction with ICAM-I and ICAM-2 regulates Th2 cytokine production." J Immunol161, 5138-5142.

Scharffeiter-Kochanek, K., et al. (1998). "Spontaneous skin ulceration and defective T cell function in CD18 null mice." J Exp Med 188, 119-131.

Shankaran et al. "IFNy and Lymphocytes Prevent Primary Tumour Development and Shape Tumour Immunogenicity," Nature (2001) 410:1107-1111.

Shibuya. K.. et al. (1999). "Physical and functional association of LFA-1 with DNAM-1 adhesion molecule." Immunity 11, 615-623.

Shier, P., et al. (1999). Defective CD8+ T cell activation and cytolytic function in the absence of LFA-1 cannot be restored by increased TCR signaling. J Immunol163, 4826-4832.

Soede. R. D., et al. (1999). LFA-1 to LFA-1 signals involve zeta-associated protein-70 (ZAP-70) tyrosine kinase: relevance for invasion and migration of a T cell hybridoma. J Immunol163, 4253-4261.

Somersalo, K., et al. (1995). "Activation of natural killer cell migration by leukocyte integrin-binding peptide from intracellular adhesion molecule-2 (ICAM-2)." J Biol Chem 270. 8629-8636.

Song, X., et at. "Flow cytometry-based biosensor for detection of multivalent proteins." Anal Biochem 284, 35-41. (2000).

Staquet, M. J., et al. (1995). "Expression of ICAM-3 on human epidermal dendritic cells." Immunobiology 192, 249-61.

Starling, G. C., et at. (1995). "Intercellular adhesion molecule3 is the predominant co-stimulatory ligand for leukocyte function antigen-1 on human blood dendritic cells." Eur J Immunol 25, 2528-2532.

Sugai. T., et al. (2000). "Allelic losses of 17p, 5q, and 18q loci in diploid and aneuploid populations of multiploid colorectal carcinomas." Hum Pathol 31, 925-30.

Tanaka Y, et al. "Intercellular adhesion molecule 1 underlies the functional heterogeneity of synovial cells in patients with rheumatoid arthritis: involvement of cell cycle machinery." Arthritis Rheum. Nov. 2000;43(11):2513-22.

Weber, K. S., et al. (2001). "Cytohesin-1 is a dynamic regulator of distinct LFA-1 functions in leukocyte arrest and transmigration triggered by chemokines." Curr Biol 11, 1969-1974.

Yu, T. K., et al. (2000). "IL-2 activation of NK cells: involvement of MKK1/2/ERK but not p38 kinase pathway." J Immunol 164. 6244-6251.

* cited by examiner

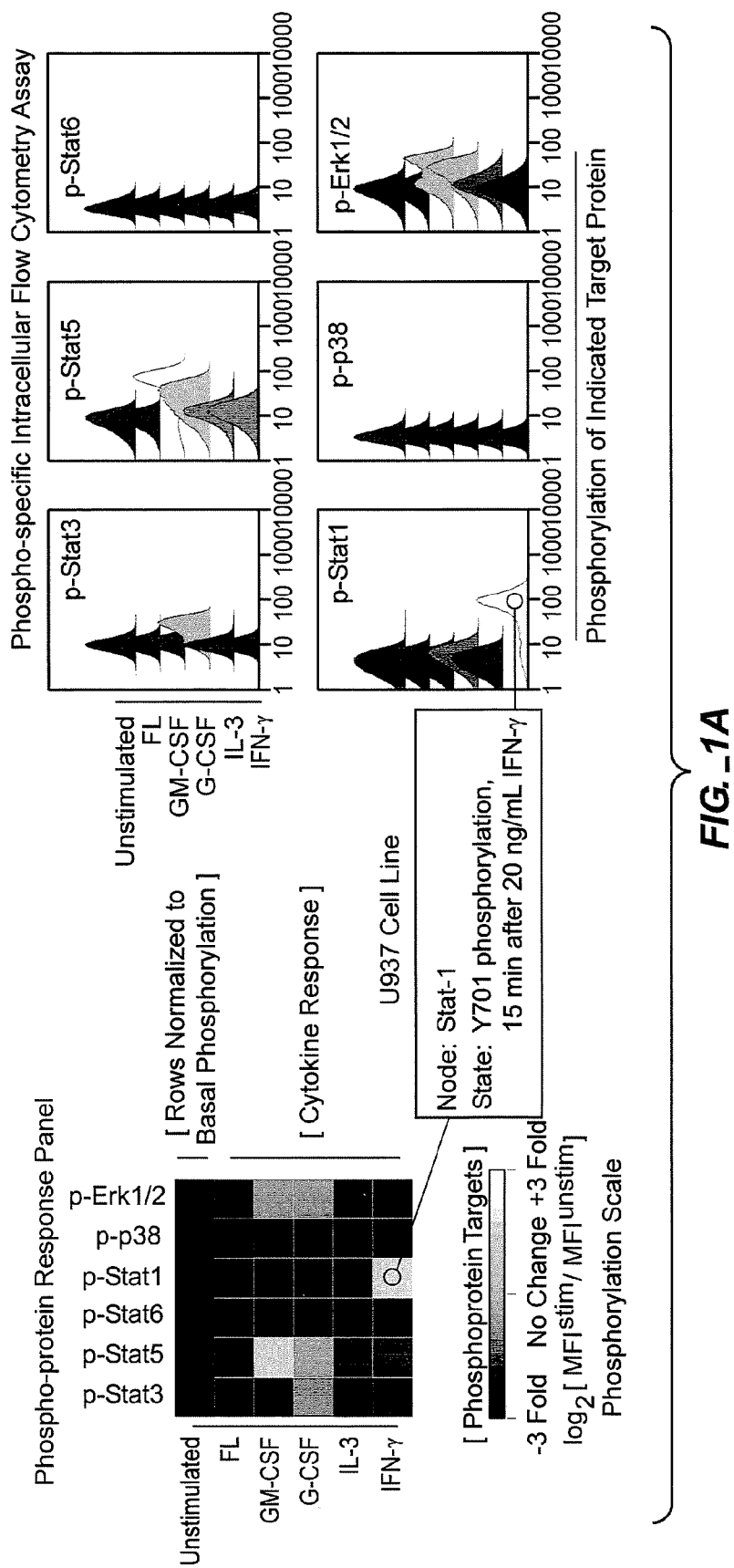
FIG._1A

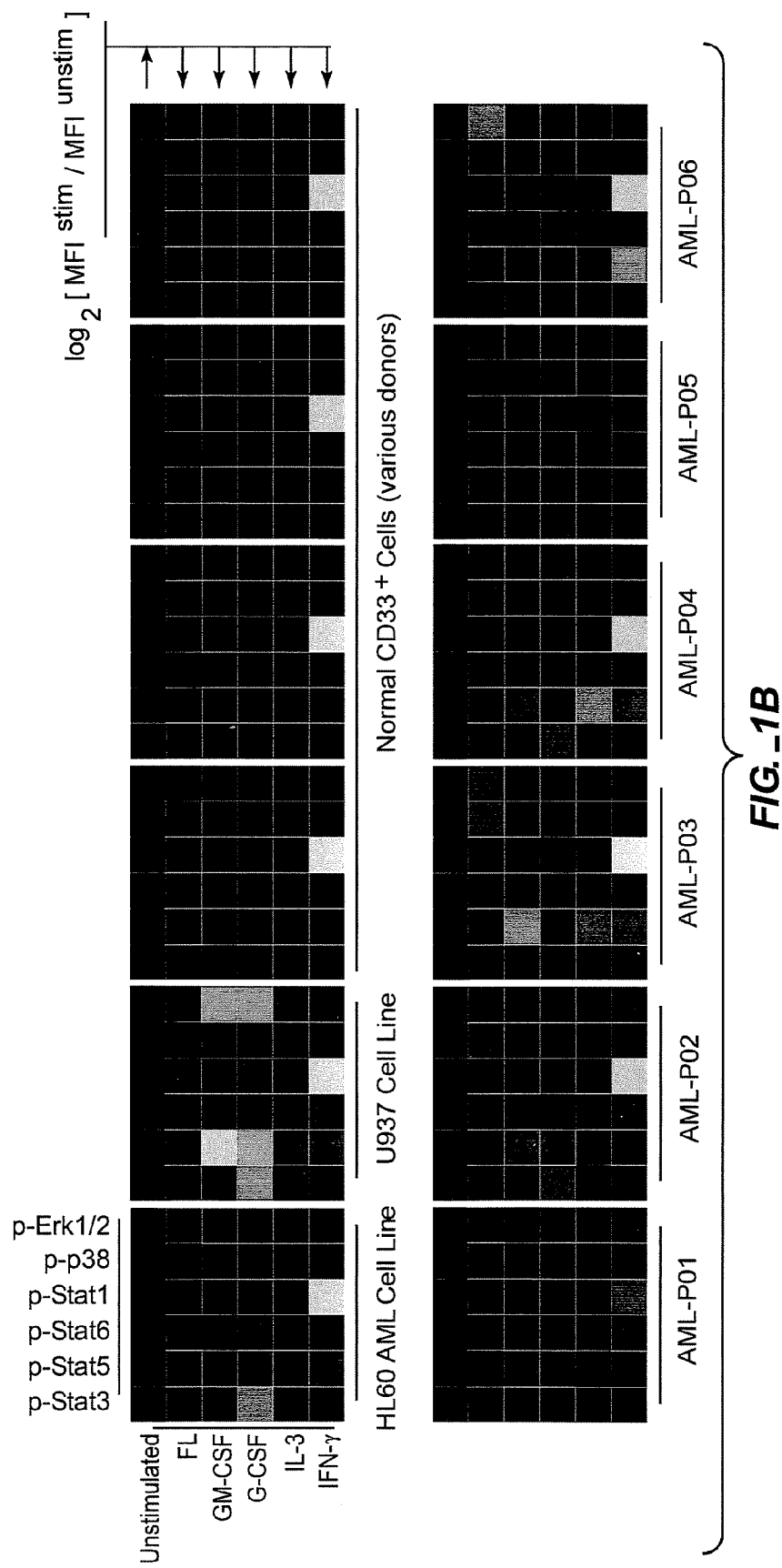
FIG._1B

| Nodes | AML P01 - P30 | Node State Variance ($\sigma^2$) | |
|---|---|---|---|
| p-Stat3 | | Basal | 0.45 |
| | | FL | 0.01 |
| | | GM-CSF | 0.01 |
| | | G-CSF | 0.37 |
| | | IL-3 | 0.03 |
| | | IFN-$\gamma$ | 0.06 |
| p-Stat5 | | Basal | 0.35 |
| | | FL | 0.05 |
| | | GM-CSF | 0.11 |
| | | G-CSF | 0.29 |
| | | IL-3 | 0.63 |
| | | IFN-$\gamma$ | 0.33 |
| p-Stat6 | | Basal | 0.55 |
| | | FL | 0.02 |
| | | GM-CSF | 0.01 |
| | | G-CSF | 0.01 |
| | | IL-3 | 0.01 |
| | | IFN-$\gamma$ | 0.01 |
| p-Stat1 | | Basal | 0.15 |
| | | FL | 0.01 |
| | | GM-CSF | 0.02 |
| | | G-CSF | 0.07 |
| | | IL-3 | 0.01 |
| | | IFN-$\gamma$ | 1.72 |
| p-p38 | | Basal | 0.22 |
| | | FL | 0.04 |
| | | GM-CSF | 0.02 |
| | | G-CSF | 0.02 |
| | | IL-3 | 0.03 |
| | | IFN-$\gamma$ | 0.02 |
| p-Erk1/2 | | Basal | 0.45 |
| | | FL | 0.13 |
| | | GM-CSF | 0.05 |
| | | G-CSF | 0.04 |
| | | IL-3 | 0.08 |
| | | IFN-$\gamma$ | 0.06 |

FIG._2A

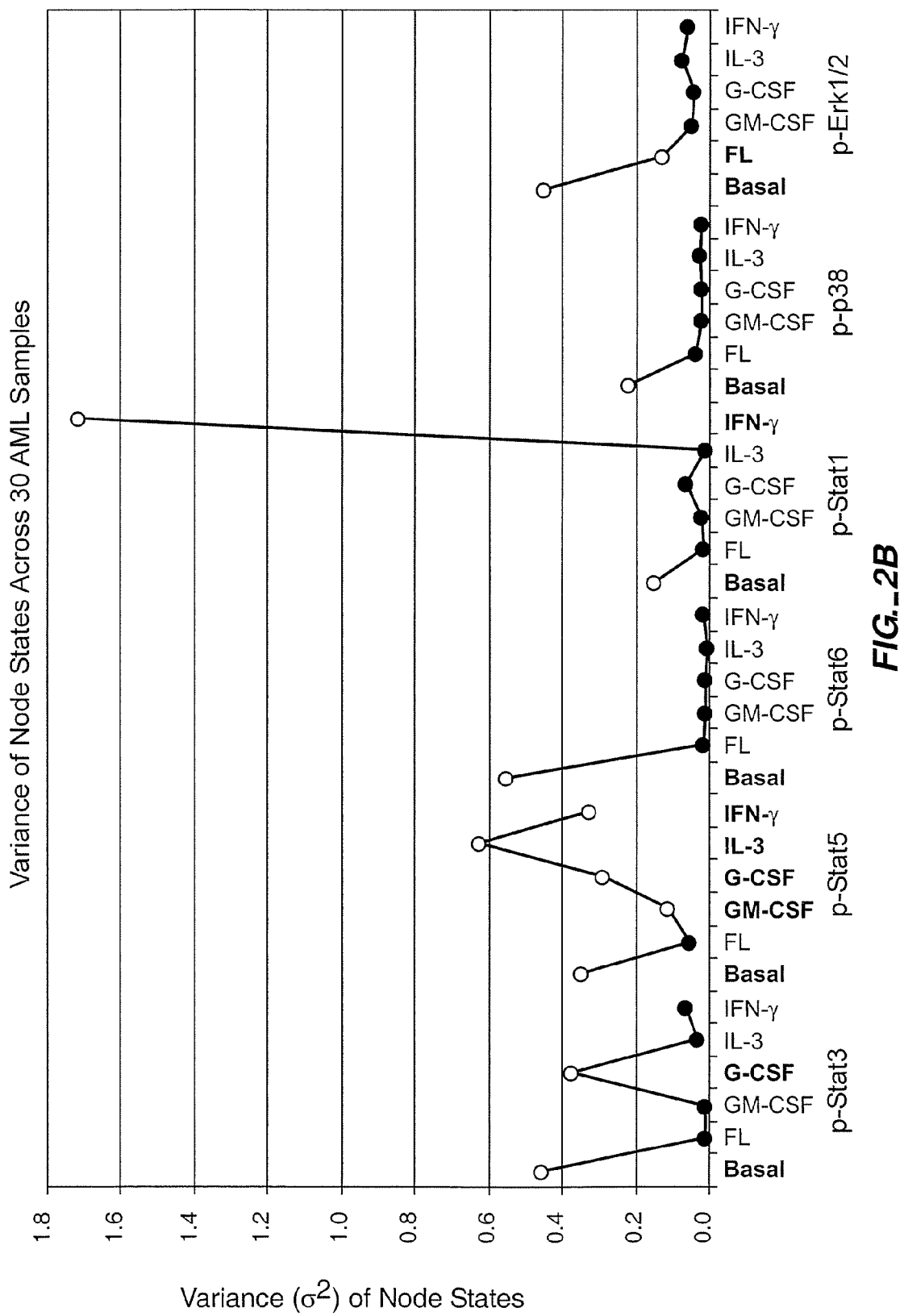
FIG._2B

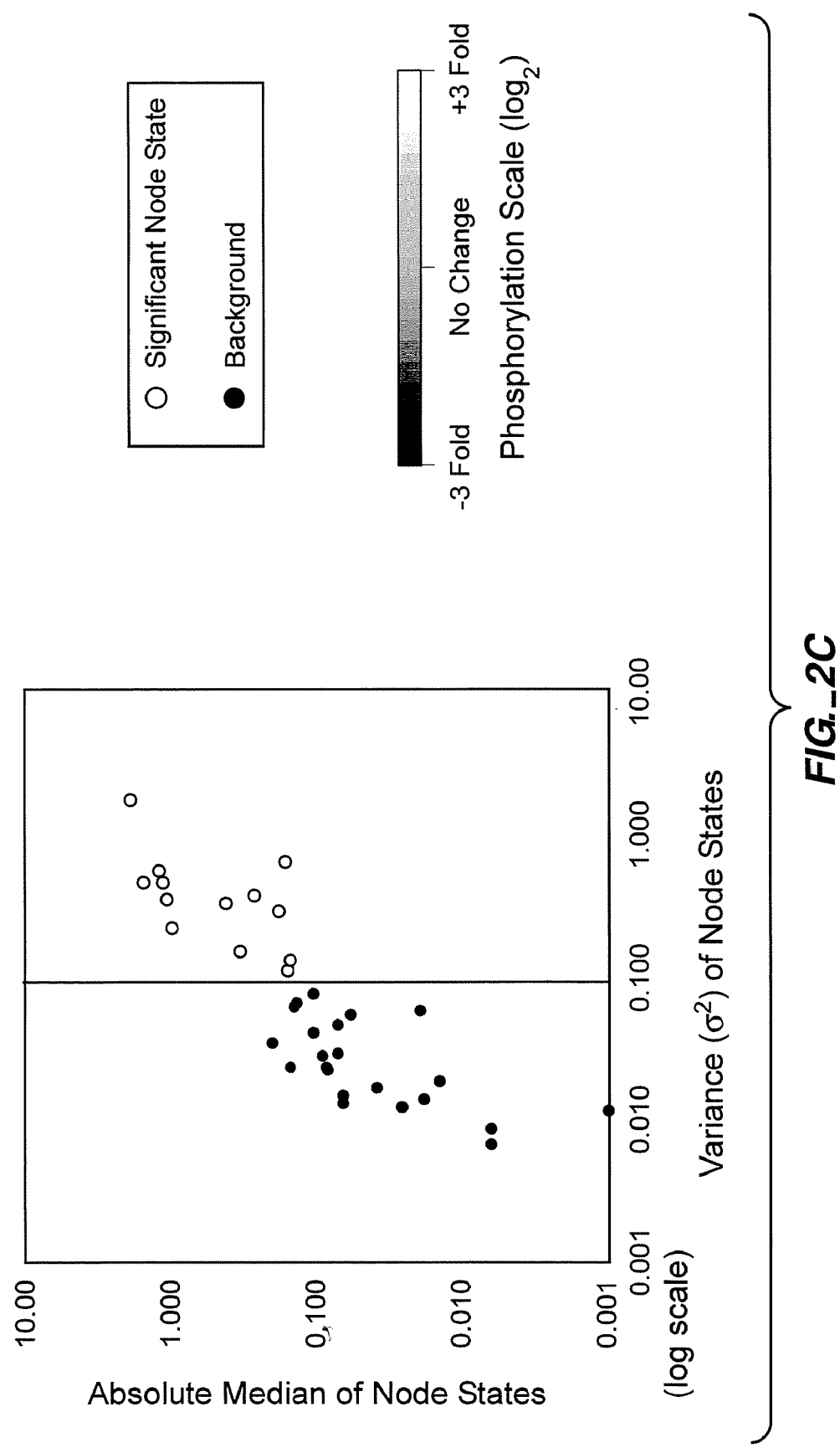
FIG._2C

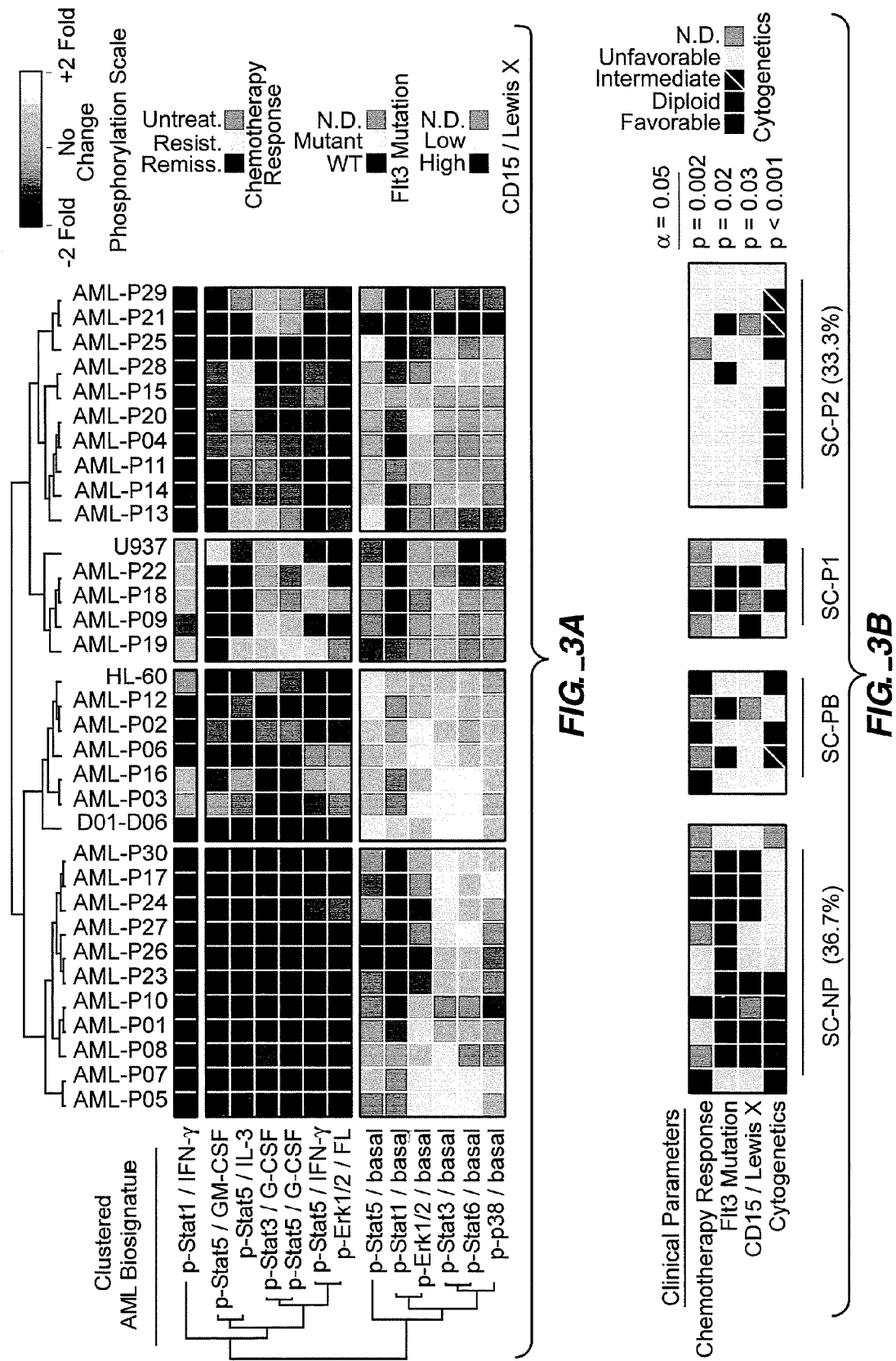
FIG._3A
FIG._3B

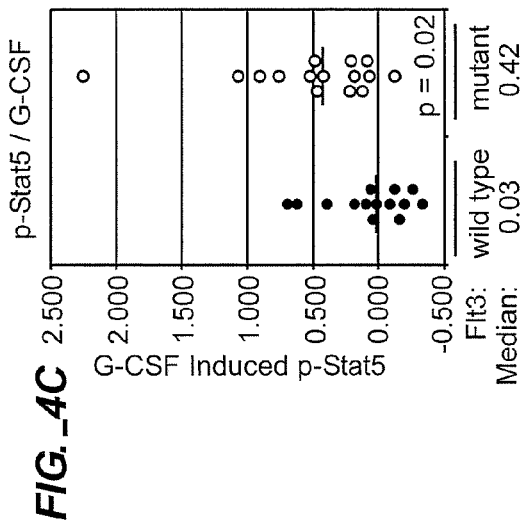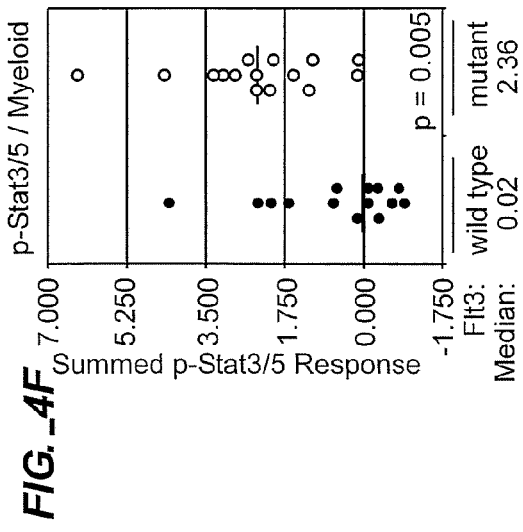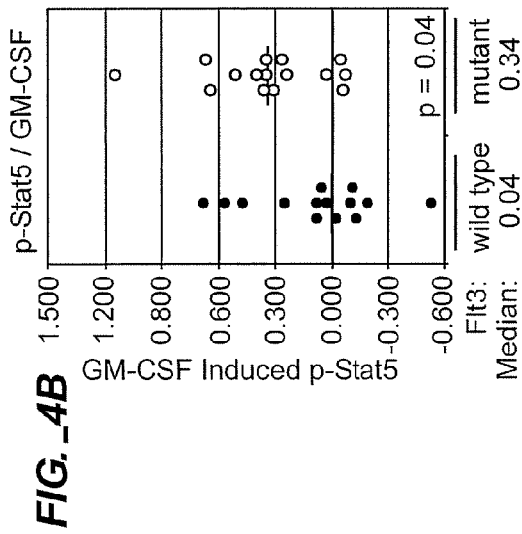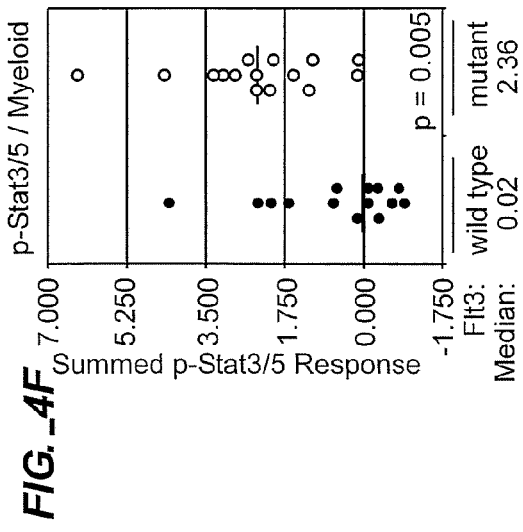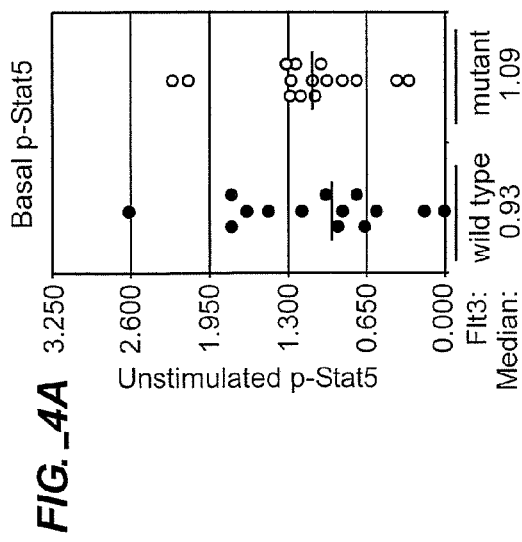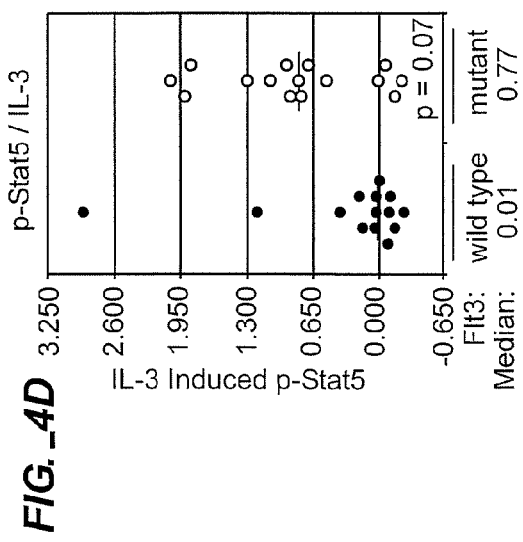
FIG._4A  FIG._4B  FIG._4C  FIG._4D  FIG._4E  FIG._4F

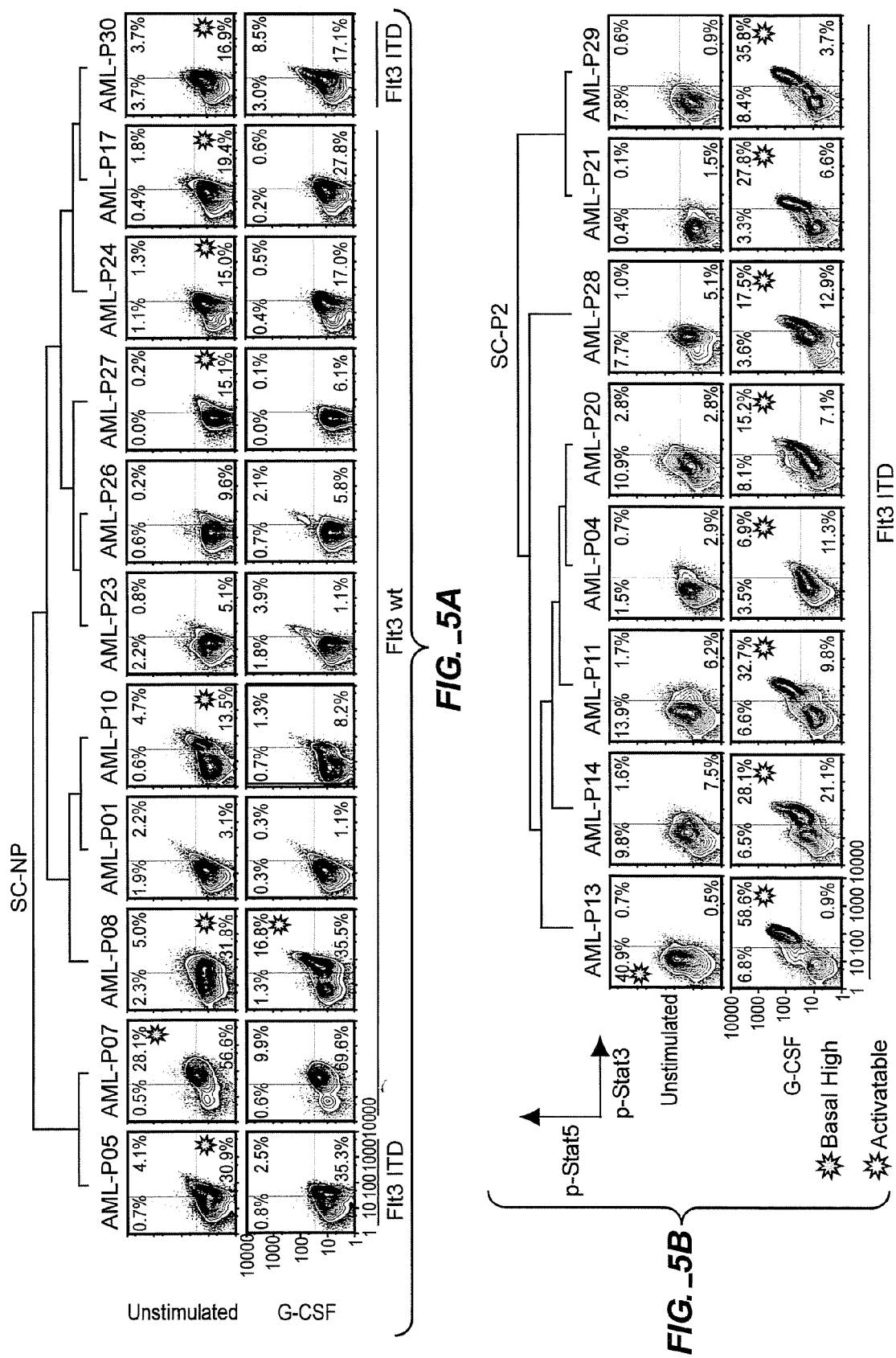
FIG. _5A
FIG. _5B

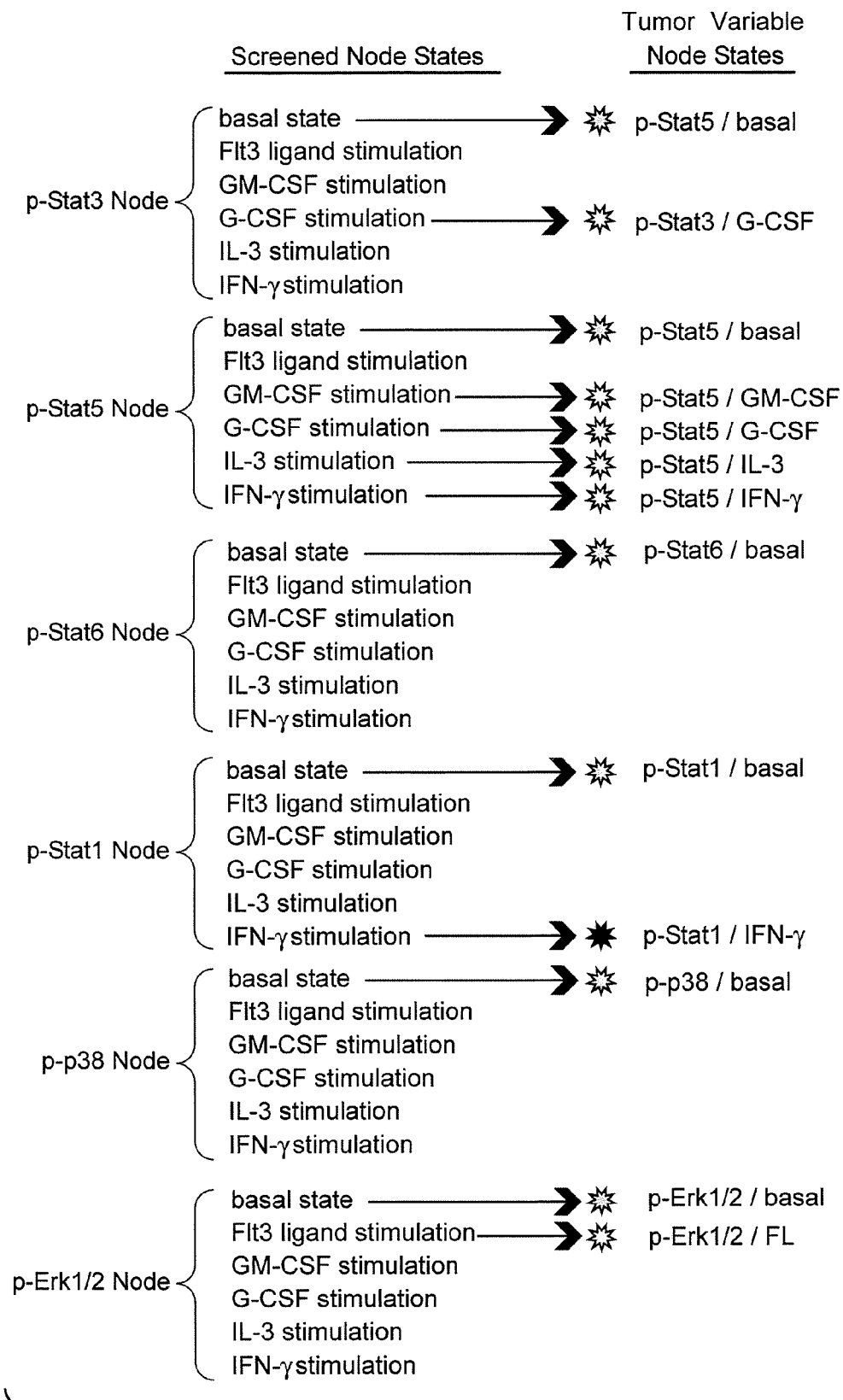
FIG._6A

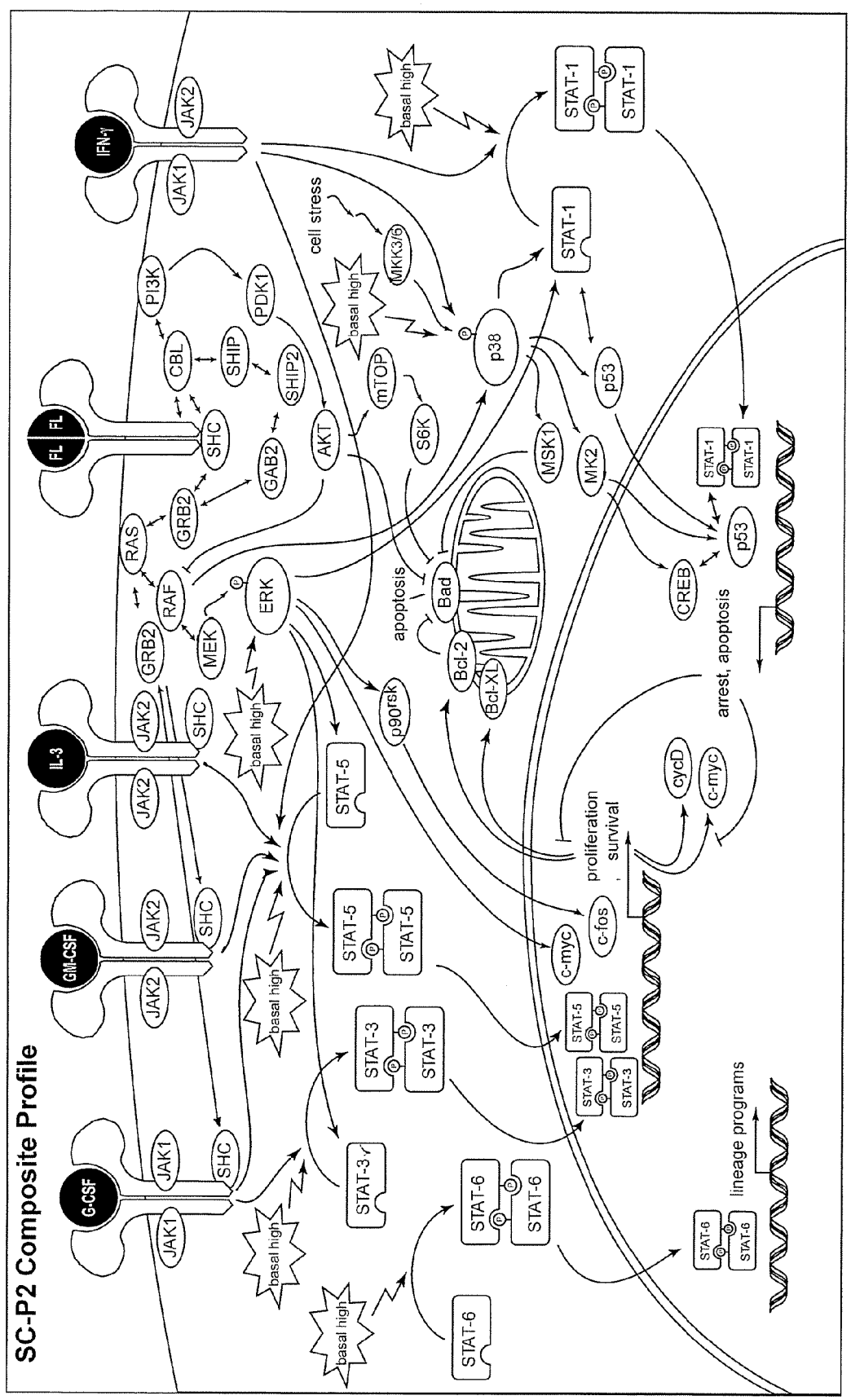
FIG._6B-1

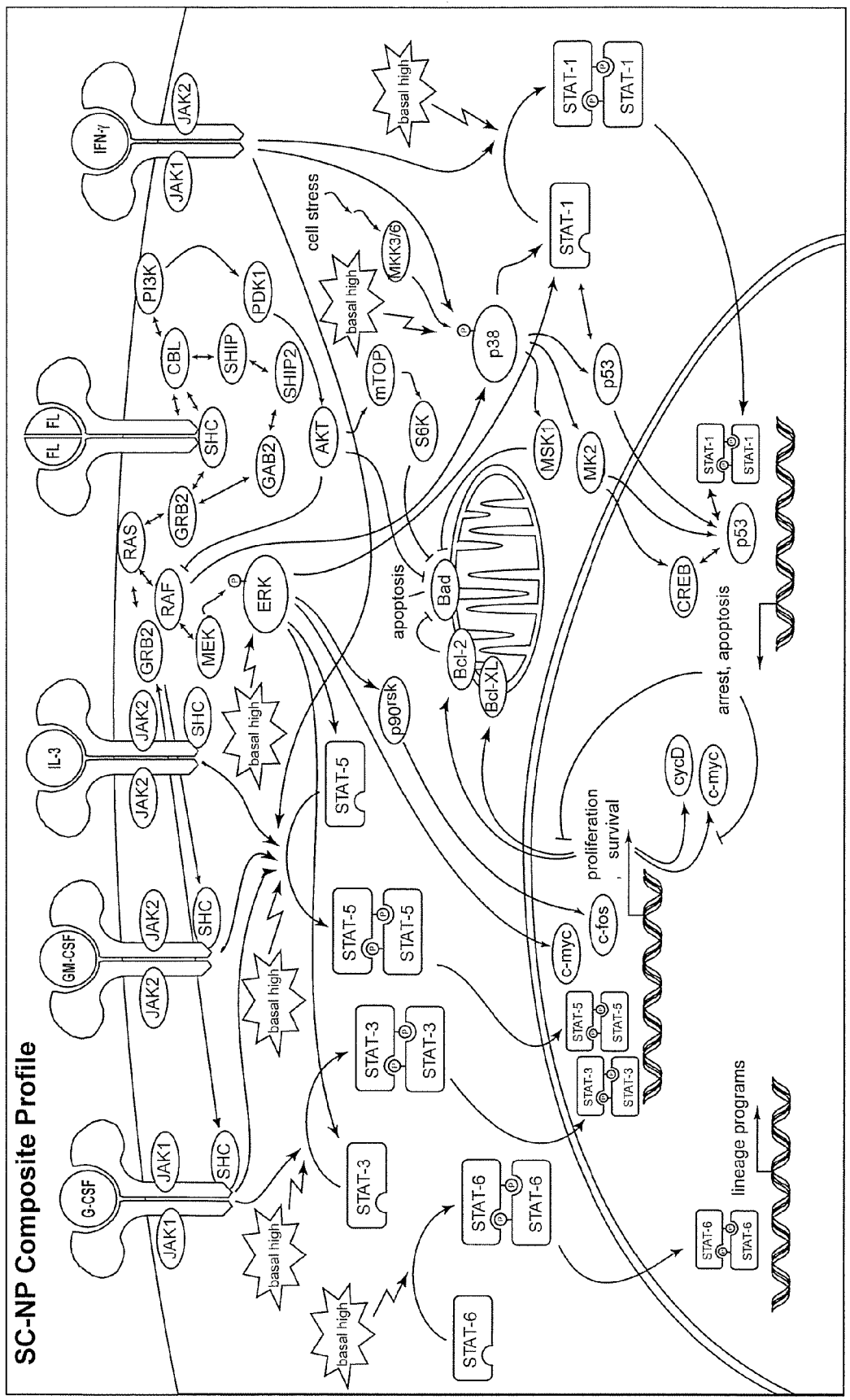
FIG._6B-2

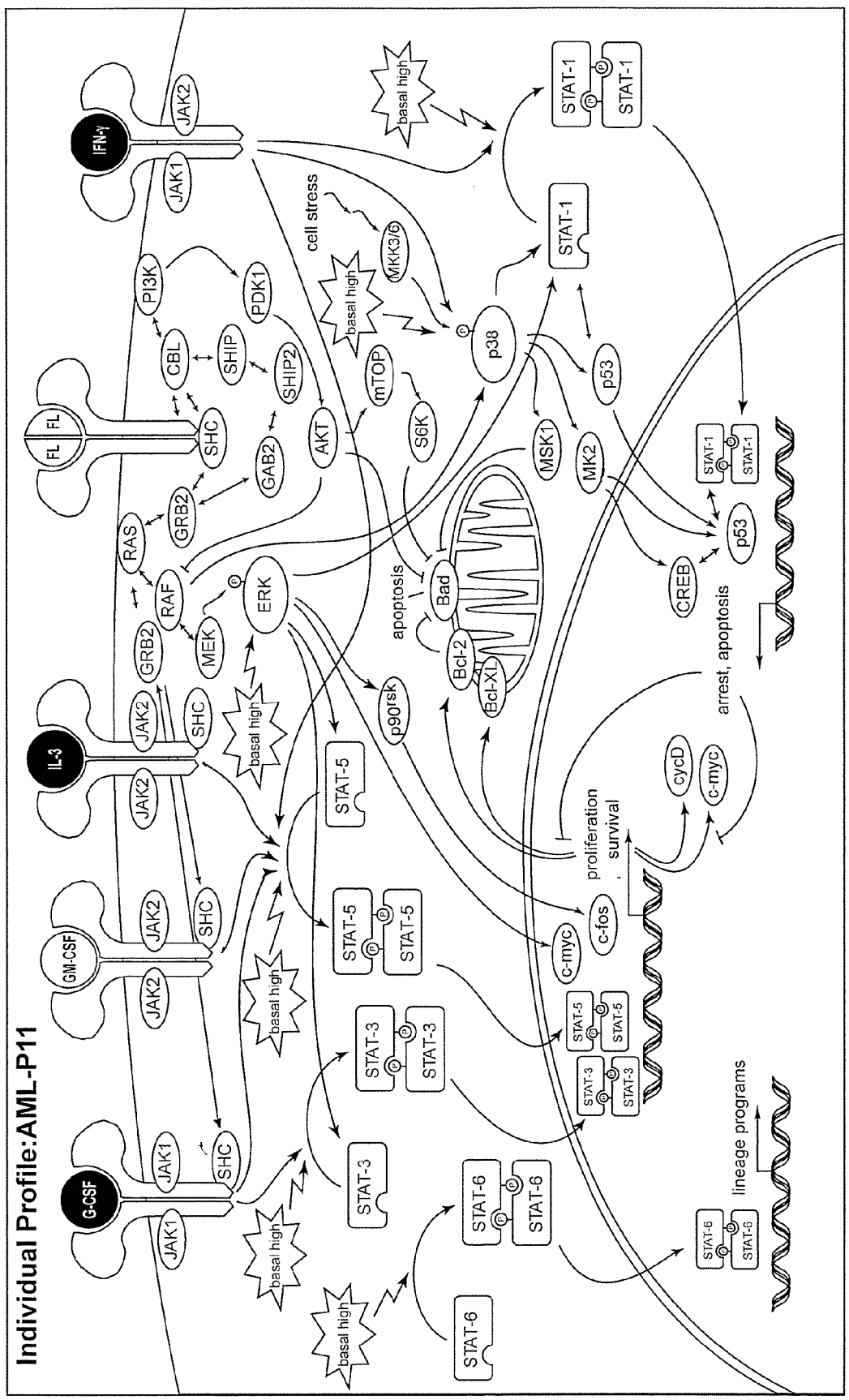
FIG. _7A

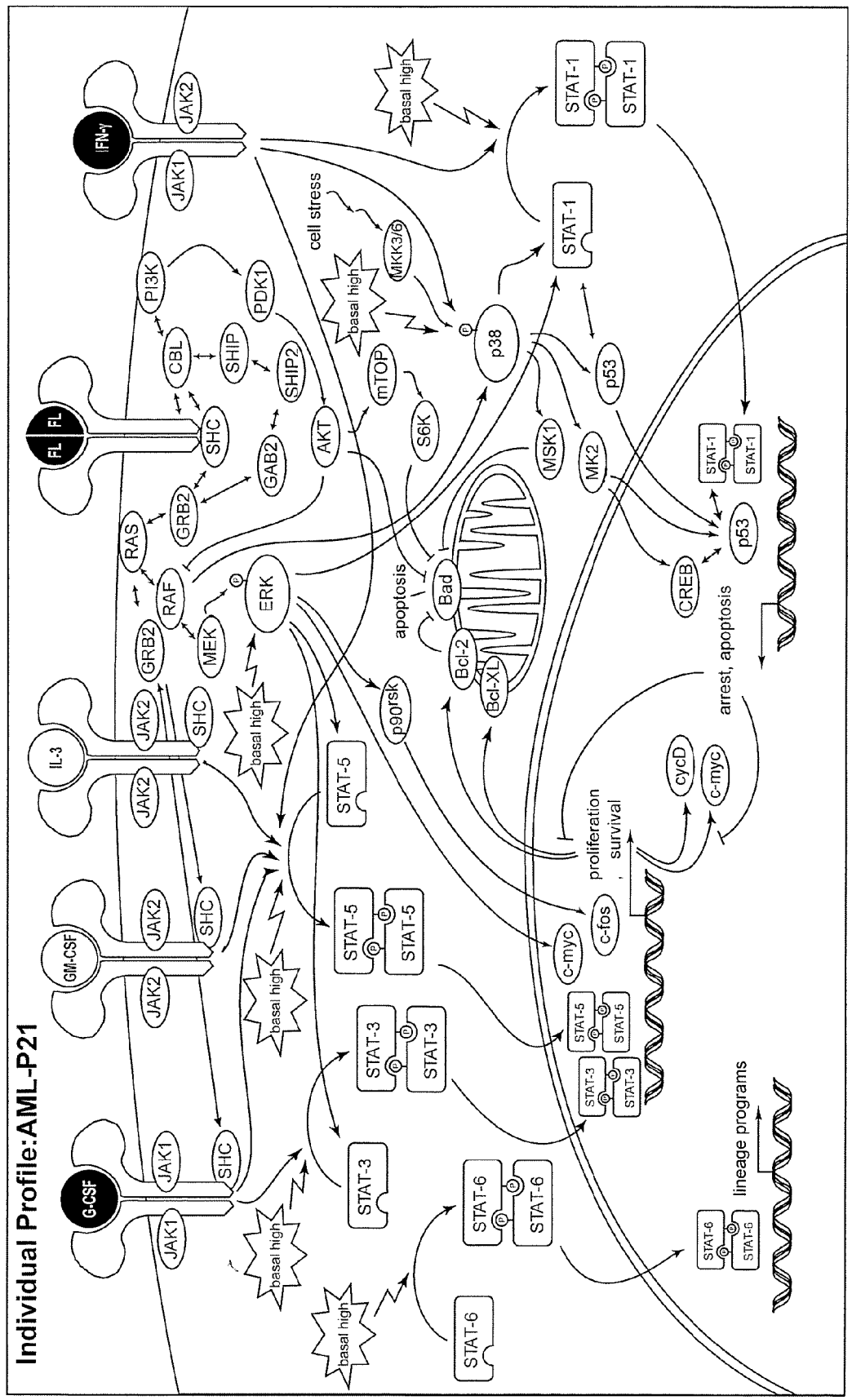
FIG._7B

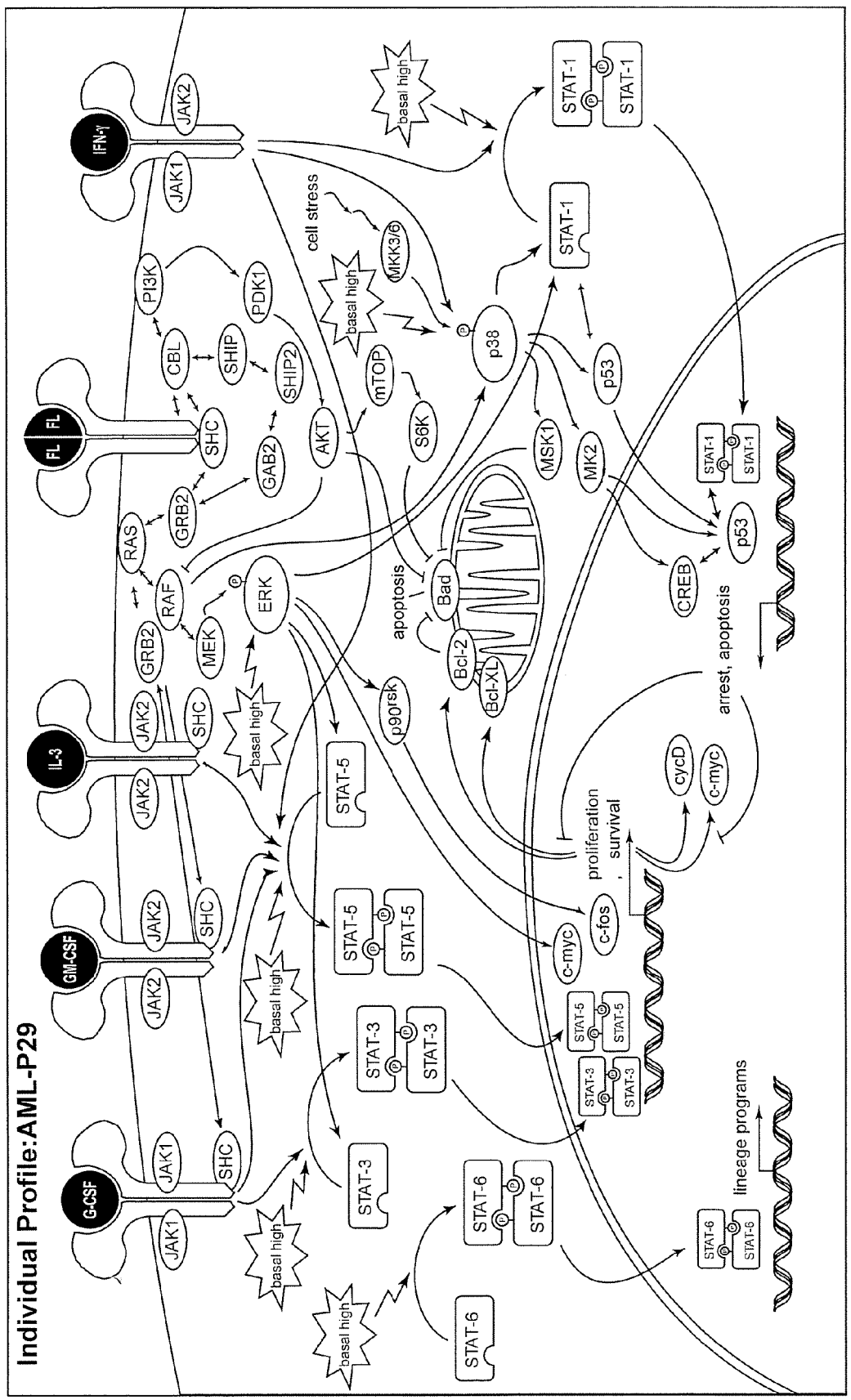
FIG._7C

METHODS AND COMPOSITIONS FOR RISK STRATIFICATION

This application is a divisional of U.S. patent application Ser. No. 10/898,734 filed on Jul. 21, 2004, now U.S. Pat. No. 7,393,656, which is hereby expressly incorporated by reference in its entirety.

FIELD OF THE INVENTION

The invention relates generally to the field of protein detection using flow cytometry. More specifically, the invention relates to using polychromatic flow cytometry to identify signal transduction events and cellular activation profiles. The invention further relates to the use of potentiators that impact activation states and thus allow for further characterization of signal transduction events and activation profiles.

BACKGROUND OF THE INVENTION

Proteins are major components of cells and the spatiotemporal expression pattern and the subcellular localization of proteins determine the shape, structure, and function of cells. Many proteins are dynamically regulated so that their activity is altered in response to certain intrinsic or extrinsic cues frequently referred to herein as "activation events". Such regulation generally occurs in the context of protein-protein interaction networks commonly described as signal transduction cascades. The individual members of such cascades often exist in either active or non-active states, and it is the conversion between these states that leads to propagation or inhibition of a signal through the cascade. Given their integral role in cellular development and function, dysregulation of such cascades can lead to numerous diseases, and in particular those diseases involving improper cell proliferation such as cancer.

Researchers investigating signal transduction cascades have traditionally used methods that rely on lysates of cellular populations, e.g. western blots. Such methods have a number of inherent limitations that can obscure key information. For example, using populations of cells to produce a lysate hightens the possibility that rare cell events will be diluted to an extent that key activation events are no longer evident. In addition, the use of lysates can only approximate the native cellular activation profiles of signal cascades, as lysis inherently alters the cascade environment. Given such limitations, new methods capable of focusing on the individual members of signal transduction cascades in native environments are necessary to better understand the role of activation events in disease.

Accordingly, the present invention provides an approach for the simultaneous determination of the activation states of a plurality of proteins in single cells. This approach permits the rapid detection of heterogeneity in a complex cell population based on activation states, and the identification of cellular subsets that exhibit correlated changes in activation within the cell population. Moreover, this approach allows the correlation of cellular activities or properties, including the ability to classify disease states based on signal transduction activation state. In addition, the use of potentiators of cellular activation allows for further characterization of such pathways and cell populations.

SUMMARY OF THE INVENTION

In a preferred embodiment, the instant invention provides a method for detecting the activation state of at least two activatable proteins in each cell of a cell population. The first step of this method is to provide a population of cells that have the two activatable proteins. That step is followed by contacting the population of cells with a plurality of activation state-specific binding elements. These activation state-specific binding elements have at least a first activation state-specific binding element that binds to a first isoform of the first activatable protein; and a second activation state-specific binding element that binds to a first isoform of the second activatable protein. The presence or absence of binding of the elements is then detected using flow cytometry to determine the activation state of the two proteins.

In an additional embodiment, the two binding elements are labeled with different labels.

In an additional embodiment, the cells tested are primary cells.

In an additional embodiment, the activation state information of the first and second activatable proteins is used to determine the cellular status of at least one cell.

In an additional embodiment, the cellular status determined is drug susceptibility.

In an additional embodiment, the population of cells is contacted with a candidate agent prior to being contacted with the binding elements.

In an additional embodiment, the candidate agent is a potentiator.

In an additional embodiment, the potentiator is a cytokine.

In an additional embodiment, the potentiator is a growth factor.

In an additional embodiment, the activation state of at least one of the activatible proteins is a phosphorylation state.

In an additional embodiment, at least one of the activatible proteins is a kinase.

In an additional embodiment, at least one of the activatible proteins is a caspase.

In an alternative embodiment, the instant invention provides a method for detecting the activation state of at least one activatable protein in each cell of a population of cells. The first step of the method is to provide a population of cells comprising the first activatable protein. The next step involves contacting the population of cells with a plurality of substrates, where the plurality of substrates includes at least one substrate that is modified by the activatable protein. Flow cytometry can then be used to detect the activation state of the activatable protein by measuring the amount of substrate that has been modified.

In additional embodiments, the present invention provides methods and compositions for simultaneously detecting the activation state of a plurality of activatable proteins in single cells using flow cytometry. The invention further provides methods and compositions of screening for bioactive agents capable of coordinately modulating the activity or activation state of a plurality of activatable proteins in single cells. The methods and compositions can be used to determine the protein activation profile of a cell for predicting or diagnosing a disease state, and for monitoring treatment of a disease state. Further, the methods and compositions of the present invention can be used optionally to sequentially detect the activation state of a plurality of activatable proteins in single cells. In addition, the methods and compositions of the present invention can be used optionally detect the activation state of a single protein or modulate the activity or activation state of a single protein.

The invention provides populations of cells, single cells, cell lysates, proteins, and samples comprising populations of cells, single cells, cell lysates, proteins useful in the methods of the present invention. In particular, the invention provides activatable proteins and activation state-specific antibodies that bind to a specific isoform of an activatable protein. In one aspect, the activation state-specific antibodies are conjugated to a label, preferably a fluorescent label, and more preferably a FRET label.

In one aspect, the invention provides methods of detecting the activation state of at least a first and a second activatable protein in single cells, the method comprising the steps of: a) providing a population of cells comprising the first and the second activatable proteins; b) contacting the population of cells with a plurality of activation state-specific antibodies, wherein the plurality of activation state-specific antibodies comprise: i) at least one first activation state-specific antibody that is capable of binding to a corresponding isoform of the first activable protein in the population of cells; and ii) at least one second activation state-specific antibody that is capable of binding to a corresponding isoform of the second activatable protein in the population of cells; and c) using flow cytometry to detect the binding of the first and second activation state-specific antibodies in single cells of the population of cells, wherein the binding of the first activation state-specific antibody is indicative of a specific activation state of the first activatable protein, and the binding of the second activation state-specific antibody is indicative of a specific activation state of the second activatable protein.

In a further aspect, the first activatable protein is a kinase. Also in a further aspect, the first activatable protein is a caspase.

In a further aspect, the first activatable protein is a first kinase and the second activatable protein is a second kinase. Also in a further aspect, the isoform of the first kinase is a first phosphorylated kinase, and the isoform of the second kinase is a second phosphorylated kinase. In another aspect, the first activation site-specific antibody binds to the first phosphorylated kinase, and the second activation site-specific antibody binds the second phosphorylated kinase.

In a further aspect, the first activatable protein is a first caspase and the second activatable protein is a second caspase. Also in a further aspect, the isoform of the first caspase is a cleaved product of a first pro-caspase, and the isoform of the second caspase is a cleaved product of a second pro-caspase. In another aspect, the plurality of activation site-specific antibodies comprise a first activation site-specific antibody that binds to the isoform of the first caspase, and a second activation site-specific antibody that binds to the isoform of the second caspase.

In another aspect, the invention provides methods of detecting the activation state of at least a first activatable protein in single cells, the method comprising the steps of: a) providing a population of cells comprising at least the first activatable protein; b) contacting the population of cells with a plurality of substrates; wherein the plurality of substrates comprise at least a first substrate that is capable of being modified by a corresponding isoform of the first activatable protein in the population of cells; and c) using flow cytometry to detect the modification of the first substrate in single cells of the population of cells, wherein the modification is indicative of a specific activation state of the first activatable protein.

In a further aspect, the population of cells further comprises a second activatable protein; the plurality of substrates further comprise a second substrate that is capable of being modified by a corresponding isoform of the second activable protein in the population of cells; and step c) further comprises using the flow cytometry to detect the modification of the second substrate in single cells of the population of cells, wherein the modification of the second substrate is indicative of a specific activation state of the second activatable protein.

In another aspect, the invention provides methods of detecting a protein activation state profile of single cells based on the activation state of at least a first activatable protein in the cells, the method comprising the steps of: a) providing a population of cells comprising at least the first activatable protein; b) contacting the population of cells with a plurality of substrates; wherein the plurality of substrates comprise at least a first substrate that is capable of being modified by a corresponding isoform of the first activatable protein in the population of cells; c) contacting the population of cells with a plurality of activation state-specific antibodies, wherein the activation state-specific antibodies comprise at least one first activation state-specific antibody that is capable of binding to a corresponding isoform of the first activatable protein in the population of cells; and d) using flow cytometry to simultaneously detect: i) the binding of the first activation state-specific antibody in single cells of the population of cells, wherein the binding of the first activation state-specific antibody is indicative of a specific activation, state of the first activatable protein; and ii) the modification of the first substrate the single cells, wherein the modification is indicative of the specific activation state of the first activatable protein.

In a further aspect, the population of cells further comprises a second activatable protein; the plurality of substrates further comprises a second substrate that is capable of being modified by a corresponding isoform of the second activatable protein in the population of cells; and step d) further comprises using the flow cytometry to detect the modification of the second substrate in the single cells, wherein the modification is indicative of a specific activation state of the second activatable protein.

In a further aspect, the plurality of activation state-specific antibodies further comprises a second activation state-specific antibody that is capable of binding to a corresponding isoform of the second activatable protein in the population of cells, and step c) further comprises using the flow cytometry to detect the binding of the second activation state-specific antibody the single cells of the population of cells, wherein the binding of the second activation state-specific antibody is indicative of the specific activation state of the second activatable protein.

In another aspect, the invention provides methods of screening for a bioactive agent capable of modulating the activity of at least a first activatable protein in cells, the method comprising: a) providing a population of cells, each of the cells comprising at least the a first activable protein, a second activatable protein, and a third activatable protein, wherein the first activable protein can activate the second activatable protein thereby forming a specific isoform of the second activable protein (isoform-2), and wherein the second activable protein can activate the third activatable protein thereby forming a specific isoform of the third activatable protein (isoform-3); b) contacting the cells with a second activation state-specific antibody, a third activation state-specific antibody, and a candidate bioactive agent, wherein the second activation state-specific antibody is capable of binding to the isoform-2, and wherein the third activation state-specific antibody is capable of binding to the isoform-3; c) using fluorescent activated cell sorting (FACS) to sort single cells of the population of cells based on the presence of the isoform-2 and the isoform-3; and d) determining the ratio of the isoform-2 to the isoform-3 in the single cells in the presence and absence of the candidate bioactive agent, wherein a difference in the ratio of the isoform-2 to the isoform-3 in the presence and absence of the candidate bioactive agent is indicative of the ability of the candidate bioactive agent to modify the activity of the first activatable protein.

In a further aspect, the first activatable protein is activated by an activating agent.

In a further aspect, the first activatable protein is a caspase. In another aspect, the first activatable protein is a kinase; in an additional aspect, the kinase is PI3K; and in a further aspect the PI3K is activated by a growth factor or by activation of a cell surface receptor.

In a further aspect, the kinase is PI3K; the second activatable protein is PIP2; the third activatable protein is PIP3; the isoform-2 is PIP 4,5 bisphosphate; and the isoform-3 is PIP 3,4,5.

In a further aspect, the first activatable protein is ICAM-2; the activity is apoptosis; the second activatable protein is PIP2; the third activatable protein is PIP3; the isoform-2 is PIP 4,5 bisphosphate; and the isoform-3 is PIP 3,4,5. In a further aspect step a) further comprises clustering the ICAM-2, ICAM-3, or ICAM-1.

In a further aspect, the plurality of activation state-specific antibodies comprise at least one antibody selected from a group of antibodies consisting of: anti-AKT-phospho-Ser473, anti-AKT phospho-Thr308, anti-p44/42 MAPK phospho-Thr202/Tyr204, anti-TYK2 phospho-Tyr1054/1055, anti-p38 MAPK phospho-Thr180/Tyr182, anti-JNK/SAPK phospho-Thr183/Tyr185, anti-phospho-tyrosine, anti-phospho-threonine, anti-PIP2, and anti-PIP3.

In a further aspect, step a) further comprises contacting the population of cells with an agent that induces the activation of at least the first activatable protein.

In a further aspect, step a) further comprises contacting the population of cells with an agent that induces the activation of at least one of the first and the second activatable proteins.

In a further aspect, step a) further comprises contacting the population of cells with an agent that induces the activation of at least one of the first, the second, and the third activatable proteins.

In a further aspect, the methods further comprise sorting the single cells based on the activation state of the first activatable protein, and the activation state of the second activatable protein.

In a further aspect, the first activation state-specific antibody comprises a first label, wherein the second activation state-specific antibody comprises a second fluorescent label and, wherein the sorting is by fluorescent activated cell sorting (FACS).

In a further aspect, the first activation state-specific antibody comprises a first FRET label; the second activation state-specific antibody comprises a second FRET label and the sorting is by fluorescent activated cell sorting (FACS).

In a further aspect, the first activation state-specific antibody comprises a FRET label; the second activation state-specific antibody comprises a label; and the sorting is by fluorescent activated cell sorting (FACS).

In a further aspect, step a) further comprises fixing the cells.

In a further aspect, the cells are mammalian cells.

In an alternative embodiment, the instant invention provides methods of prognosing a clinical outcome for a patient that include first creating a cytokine response panel representing a statistically sufficient number of individuals, followed by creating a cytokine response panel for the patient; and then comparing said patient's cytokine response panel to the cytokine response panel representing a statistically sufficient number of individuals in order to come to a prognosis of the patient's clinical outcome.

In an additional embodiment, the cytokine response panels are created by first detecting the phosphorylation state of multiple phospho-proteins in non-stimulated cells then detecting the phosphorylation state of multiple phospho-proteins in cytokine-stimulated cells and determining the difference, if any, of the phosphorylation state of the phospho-proteins in the stimulated and non-stimulated cells.

In an additional embodiment, the detection is accomplished by intracellular phospho-specific flow cytometry.

In an additional embodiment, the phospho-proteins are selected from the group consisting of: Stat1, Stat3, Stat5, Stat6, p38, and Erk1/2.

In an additional embodiment, the cytokine is selected from the group consisting of: Flt3 ligand, GM-CSF, G-CSF or IL-3.

BRIEF DESCRIPTION OF THE DRAWINGS

FIGS. 1A and B A cytokine response panel reveals potentiated signal transduction nodes in primary acute myeloid leukemias. FIG. 1A, To survey the signal transduction network of normal and leukemic cells a grid of six stimulation conditions by six phospho-protein targets was designed. Stimulation states, shown in rows, included unstimulated or 20 ng/mL of FL, GM-CSF, G-CSF, IL-3, or IFN-γ. Target phosphorylations were detected using phospho-specific antibodies for Stat 1, Stat3, Stat5, Stat6, p38, and Erk1/2, shown in columns. Each square in the grid represents the response of one phosphorylation site to one condition (termed the state of a signaling node). The relationship between the grid and the flow cytometry data on which it is based is diagrammed for U937 cells. In these cells, the median fluorescence intensity (MFI) that showed the largest increase compared to the unstimulated state was observed for phosphorylation of Stat1 following IFN-γ. FIG. 1B, Representative cytokine response panels of the HL-60 AML cell line, normal CD33+ leukocytes, and six AML patient samples are shown. Repeat experiments using these AML blasts yielded similar results (n=3), and variation among normal, healthy donors was minimal (n=6). The response to stimulation at each signaling node is calculated as log 2 (MFI stimulated/MFI unstimulated).

FIGS. 2A, 2B and 2C Basal and potentiated signaling nodes that varied among tumor samples were used to define an AML biosignature. FIG. 2A, The cytokine response panel was expanded to 30 total AML patient samples and rearranged to highlight the basal and potentiated signaling of each phospho-protein. The first row of each has been colored to show the variation in the basal phosphorylation (relative to the minimum among the AML blasts). Of 900 cytokine responses assayed, 93 (10.3%) displayed a detectable phosphorylation increase following stimulation (greater than 0.55 fold). The variance of node states was used to determine significance. FIG. 2B, Significant cytokine responses were restricted primarily to the 7/30 cytokine response nodes with a variance across tumors greater than 0.1 (yellow circles). FIG. 2C, A graph of the absolute median plotted against the variance for each node state indicates the signal to noise threshold. The seven significant cytokine response states and the six basal phosphorylation states were used as a 13-parameter profile of tumor signal transduction and were termed a biosignature.

FIGS. 3A and 3B AML patients grouped by signal transduction biosignature form four groups that exhibit significant correlations to clinical prognostic markers. FIG. 3A, The 13-parameter biosignatures of differentiated CD33+ myeloid cells from six normal blood donors (DO1-D06), U937 and HL-60 tumor cell lines, and 30 AML patient samples were grouped according to similarity using hierarchical clustering. The heat map for AML and tumor cell line cytokine responses was scaled to the donor sample medians to provide a dynamic color range. Normal donor samples clustered together and are represented as a group. As shown previously, basal responses are relative to the minimum among AML samples. FIG. 3B, Four main groups of AML patients were identified based on the similarity of their signal transduction biosignatures. We designated these groups with Signaling Cluster (SC) nomenclature based on the signaling which defined them and mapped several clinical markers within the identified patient groups. The patient samples with SC-P2 or SC-NP profiles displayed contrasting clinical markers and these markers frequently correlated with the cytokine responses defining the SC (significance assessed using $\chi 2$ tests). SC-P2 and SC-NP represented 33.3% and 36.7% of patients, respectively. No patients with a SC-P2 profile who were treated with chemotherapy showed remission (9/9, p=0.002). The SC-P2 patient samples frequently had mutations in Flt3 (8/10), while patient samples with an SC-NP profile displayed few potentiated cytokine responses and nearly always expressed wild type Flt3 (9/11) (p=0.02). Samples with an SC-P2 profile rarely expressed CD15/Lewis X antigen (9/10, p=0.03). Cytogenetic alterations were divided among branches of SC-P2 and SC-NP (20/20, p<0.001).

FIGS. 4A, 4B, 4C, 4D, 4E and 4F Flt3 mutations in primary AMLs may potentiate myeloid signal transduction nodes. FIG. 4A, Basal and cytokine response node states of patient samples with wild type or mutant Flt3 are shown for all 30 AMLs assayed. The MFI of phosphorylated Stat5 differed little in patients with wild type Flt3 and patients with mutant Flt3. In contrast, GM-CSF induced Stat5 phosphorylation (FIG. 4B) and G-CSF induced Stat5 (FIG. 4C) and Stat3 (FIG. 4E) phosphorylation all correlated with Flt3 mutation (p=0.04, 0.02, and 0.01 respectively). As a way of representing the overall effect of Flt3 mutation on myeloid signaling we summed the cytokine responses of four myeloid signaling states from the biosignature: p-Stat3/G-CSF (FIG. 4E) and p-Stat5/GM-CSF/G-CSF/IL-3 (FIGS. 4B, 4C and 4D, respectively). This summed myeloid cytokine response was significantly higher in AML patients with Flt3 mutations (p=0.005; FIG. 4F).

FIGS. 5A and 5B Representative 2D flow cytometry plots of Stat5 and Stat3 phosphorylation following G-CSF stimulation in AML patient samples with wild type Flt3 (FIG. 5A) and mutant Flt3 (ITD) (FIG. 5B). 2D contour plot representations of Stat5 and Stat3 phosphorylation (y and x axis respectively) in patient samples from SC-NP and SC-P2. Both the level of basal phosphorylation and the response to G-CSF are shown.

FIGS. 6A, 6B-1 and 6B-2 Tumor biosignatures and a potentiated model of tumor cell signaling. FIG. 6A, A general method for identifying a tumor biosignature is shown using an example of STAT and Ras/MAPK signalling node states in AML. FIGS. 6B-1 and 6B-2, Composite maps of tumor networks from profiles SC-NP and SC-P2 were built out of common signaling events observed in each cluster. Highlighted nodes were detected to be high basal or potentiated in most of the samples from a profile group.

FIGS. 7A 7B and 7C Three AML patients profiled as SC-P2 showed similarities and differences in potentiated signaling mechanisms. Pathway maps summarizing the signaling phenotype of individual patient samples are shown for three profiled as SC-P2, as per FIGS. 6B-1.

DETAILED DESCRIPTION OF THE INVENTION

Intracellular assays of signaling cascades have been limited by an inability to measure and correlate functional data based on the activation state of elements within specific signal transduction cascades. Such measurements and correlations are important for distinguishing changes in signaling status arising in rare cell subsets during signaling or in disease manifestations. Correlation of changes in signaling cascades can also find use in classifying pathologic differences in populations. The present invention handles these issues by providing methods and compositions for simultaneously detecting the activation state of a plurality of activatible elements (e.g. proteins) in single cells using flow cytometry and by providing analytical means for correlating such states to differences in populations.

The invention further provides methods and compositions of screening for bioactive agents capable of modulating the activation state of activatible elements in single cells. Thus the methods and compositions are not only useful for predicting or diagnosing a disease state, but also for monitoring treatment of a disease state. For example, determining the phosphorylation states of a set of proteins can allow for the classification and clustering of subpopulations of cells into relevant categories, which in turn aid in making determinations such as prognosis, disease progression, response to particular drugs, etc.

The invention also provides methods and compositions that include the use of potentiators to amplify the amount of functional data that can be gathered in connection with the activation state of particular elements. For example, the methods and compositions of the instant invention can be used to determine the activation profile of cells derived from a single source but which have been individually exposed to different potentiators (e.g. various cytokines), and changes to activation profiles arising due to the influence of distinct potentiators can be incorporated into the analysis.

Activation

As used herein, an "activatible element" or grammatical equivalents thereof, refers to a cellular element that has at least two isoform (and in some cases three or more isoforms) that corresponds to specific forms of the element having a particular biological, biochemical, or physical properties, e.g., an enzymatic activity, a modification (e.g., post-translational modification), or a conformation. In preferred embodiments, the activatible element is a protein. While in general the discussion below refers to activatable proteins, other activatible cellular elements are also included such as lipids, carbohydrates, and metabolites as discussed further below. The activable element can be activated or nonactivated with respect to a particular biological activity, modification, or conformation. Specifically, the "activated" or "active" isoform of the activatible protein has the particular biological activity, modification, or conformation, whereas the "nonactivated" or "non-active" isoform of the activatible protein does not have (or has a lesser or diminished level of) the particular biological activity, modification, or conformation, respectively. In some embodiments, there may be more than one isoform associated with activity or activation state; for example, in the case of activable enzymes there may be an isoform associated with an "open" conformation available for substrate binding, a second "transition state" isoform, and an isoform devoid of activity (e.g., where the activity is inhibited). Similarly, certain proteins may have multiple phosphorylation states, multiple glycosylation states, etc. Thus the activatible elements generally have an "inactive" isoform and at least one "active" isoform. In some cases, however, it may be desirable to include elements in the analysis that do no have isoforms; for example, one readout could be presence or absence of a particular metabolite, e.g. there may not be an "activatible" state.

In a preferred embodiment, the biological, biochemical, or physical property (e.g. enzymatic activity, modification, or conformation) of the activatible element is inducible or "activatible" by an activating agent or by cell signaling events. Examples of activating agents include, but are not limited to, kinases, phosphatases, proteases (e.g., caspases), drugs and hormones. Examples of cell signaling events include, but are not limited to, element clustering or binding of a cognate molecule or ligand. These examples, among others, are discussed in detail below.

The instant invention also makes use of cells that have been "potentiated." In contrast to "activation," a "potentiated" state refers the state of a cell after exposure to a potentiator which then can be activated as the case may be. As described in detail below, potentiators exert their effect on signalling cascades by directly or indirectly impacting the ability of an activatible protein to switch between activation isoforms. Examples of potentiators generally include a wide variety of environmental cues related to cellular activation, both chemical/biochemical in nature (e.g. IIs and IFNs) or physical (thermal, pH, limited media, UV radiation, etc).

As used herein, an "isoform" or grammatical equivalents thereof, refers to a form of an activatible element having a specific detectable biological activity, modification, or conformation. The isoform can be an activated (or active) form, or non-activated (or not active) form of an activatible protein. Particular or specific properties or activities are generally associated with activated isoforms of activatible proteins and will sometimes be referred to herein as "activation state activities."

Types of Activation

Activation of an activatible protein can take a variety of different forms and generally involves an alteration of the biological, biochemical, and/or physical properties of the protein. For example, many activatible proteins are dynamically regulated in response to covalent modification of the protein. Other activation events may be non-covalent; for example, activation of many enzymes is subject to allosteric inhibition, which generally involves the non-covalent binding of an inhibitor molecule.

As will be appreciated by those in the art, a wide variety of activation events can find use in the present invention. In general, the basic requirement is that the activation results in a change in the activatible protein that is detectable by some indication (termed an "activation state indicator"), preferably by altered binding to a labeled binding element or by changes in detectable biological activities (e.g., the activated state has an enzymatic activity which can be measured and compared to a lack of activity in the non-activated state). What is important is to differentiate, using detectable events or moieties, between the isoforms of two or more activation states (e.g. "off" and "on").

Accordingly, the present invention provides for the detection of a wide variety of activation events, including, but not limited to, phosphorylation, cleavage, prenylation, intermolecular clustering, conformational changes, glycosylation, acetylation, cysteinylation, nitrosylation, methylation, ubiquination, sulfation, as well as the production of activated isoforms of selenoproteins and fusion proteins.

One example of covalent modification is the substitution of a phosphate group for a hydroxyl group in the side chain of an amino acid (phosphorylation). A wide variety of proteins are known that recognize specific protein substrates and catalyze the phosphorylation of serine, threonine, or tyrosine residues on their protein substrates. Such proteins are generally termed "kinases." Substrate proteins that are capable of being phosphorylated are often referred to as phosphoproteins. Once phosphorylated, a substrate protein may have its phosphorylated residue converted back to a hydroxyl one by the action of a protein phosphatase that specifically recognizes the substrate protein. Protein phosphatases catalyze the replacement of phosphate groups by hydroxyl groups on serine, threonine, or tyrosine residues. Through the action of kinases and phosphatases a protein may be reversibly or irreversibly phosphorylated on a multiplicity of residues and its activity may be regulated thereby. Thus, the presence or absence or absence of one or more phosphate groups on an activatible protein is a preferred readout in the present invention.

Another example of a covalent modification of an activatible protein is the acetylation of histones. Through the activity of various acetylases and deacetylylases the DNA binding function of histone proteins is tightly regulated. Furthermore, histone acetylation and histone deactelyation have been linked with malignant progression. See Nature, 2004 May 27; 429(6990): 457-63.

Another form of activation involves cleavage of the activatible element. For example, one form of protein regulation involves proteolytic cleavage of a peptide bond. While random or misdirected proteolytic cleavage may be detrimental to the activity of a protein, many proteins are activated by the action of proteases that recognize and cleave specific peptide bonds. Many proteins derive from precursor proteins, or proproteins, which give rise to a mature isoform of the protein following proteolytic cleavage of specific peptide bonds. Many growth factors are synthesized and processed in this manner, with a mature isoform of the protein typically possessing a biological activity not exhibited by the precursor form. Many enzymes are also synthesized and processed in this manner, with a mature isoform of the protein typically being enzymatically active, and the precursor form of the protein being enzymatically inactive. This type of regulation is generally not reversible. Accordingly, to inhibit the activity of a proteolytically activated protein, mechanisms other than "reattachment" must be used. For example, many proteolytically activated proteins are relatively short-lived proteins, and their turnover effectively results in deactivation of the signal. Inhibitors may also be used. Among the enzymes that are proteolytically activated are serine and cysteine proteases, including cathepsins and caspases.

In a preferred embodiment, the activatible enzyme is a caspase. The caspases are an important class of proteases that mediate programmed cell death (referred to in the art as "apoptosis"). Caspases are constitutively present in most cells, residing in the cytosol as a single chain proenzyme. These are activated to fully functional proteases by a first proteolytic cleavage to divide the chain into large and small caspase subunits and a second cleavage to remove the N-terminal domain. The subunits assemble into a tetramer with two active sites (Green, Cell 94:695-698, 1998). Many other proteolytically activated enzymes, known in the art as "zymogens," also find use in the instant invention as activatible elements.

In an alternative embodiment the activation of the activatible element involves prenylation of the element. By "prenylation", and grammatical equivalents used herein, is meant the addition of any lipid group to the element. Common examples of prenylation include the addition of farnesyl groups, geranyl groups, myristoylation and palmitoylation. In general these groups are attached via thioether linkages to the activatible element, although other attachments may be used.

In alternative embodiment, activation of the activatible element is detected as intermolecular clustering of the activatible element By "clustering" or "multimerization", and grammatical equivalents used herein, is meant any reversible or irreversible association of one or more signal transduction elements. Clusters can be made up of 2, 3, 4, etc., elements. Clusters of two elements are termed dimers. Clusters of 3 or more elements are generally termed oligomers, with individual numbers of clusters having their own designation; for example, a cluster of 3 elements is a trimer, a cluster of 4 elements is a tetramer, etc.

Clusters can be made up of identical elements or different elements. Clusters of identical elements are termed "homo" clusters, while clusters of different elements are termed "hetero" clusters Accordingly, a cluster can be a homodimer, as is the case for the $\beta_2$-adrenergic receptor.

Alternatively, a cluster can be a heterodimer, as is the case for $GABA_B$-R. In other embodiments, the cluster is a homotrimer, as in the case of TNFα, or a heterotrimer such the one formed by membrane-bound and soluble CD95 to modulate apoptosis. In further embodiments the cluster is a homo-oligomer, as in the case of Thyrotropin releasing hormone receptor, or a hetero-oligomer, as in the case of TGFβ1.

In a preferred embodiment, the activation or signaling potential of elements is mediated by clustering, irrespective of the actual mechanism by which the element's clustering is induced. For example, elements can be activated to cluster a) as membrane bound receptors by binding to ligands (ligands including both naturally occurring or synthetic ligands), b) as membrane bound receptors by binding to other surface molecules, or c) as intracellular (non-membrane bound) receptors binding to ligands.

In a preferred embodiment the activatible elements are membrane bound receptor elements that cluster upon ligand binding such as cell surface receptors. As used herein, "cell surface receptor" refers to molecules that occur on the surface of cells, interact with the extracellular environment, and transmit or transduce the information regarding the environment intracellularly in a manner that may modulate cellular activity directly or indirectly, e.g., via intracellular second messenger activities or transcription of specific promoters, resulting in transcription of specific genes. One class of receptor elements includes membrane bound proteins, or complexes of proteins, which are activated to cluster upon ligand binding. As is known in the art, these receptor elements can have a variety of forms, but in general they comprise at least three domains. First, these receptors have a ligand-binding domain, which can be oriented either extracellularly or intracellularly, usually the former. Second, these receptors have a membrane-binding domain (usually a transmembrane domain), which can take the form of a seven pass transmembrane domain (discussed below in connection with G-protein-coupled receptors) or a lipid modification, such as myristylation, to one of the receptor's amino acids which allows for membrane association when the lipid inserts itself into the lipid bilayer. Finally, the receptor has an signaling domain, which is responsible for propagating the downstream effects of the receptor.

Examples of such receptor elements include hormone receptors, cytokine receptors, steroid receptors, adhesion receptors and growth factor receptors, including, but not limited to, PDGF-R (platelet derived growth factor receptor), EGF-R (epidermal growth factor receptor), VEGF-R (vascular endothelial growth factor), uPAR (urokinase plasminogen activator receptor), ACHR (acetylcholine receptor), IgE-R (immunoglobulin E receptor), estrogen receptor, thyroid hormone receptor, integrin receptors ($\beta1$, $\beta2$, $\beta3$, $\beta4$, $\beta5$, $\beta6$, $\alpha1$, $\alpha2$, $\alpha3$, $\alpha4$, $\alpha5$, $\alpha6$), MAC-1 ($\beta2$ and cd11b), $\alpha V\beta3$, opiod receptors (mu and kappa), FC receptors, serotonin receptors (5-HT, 5-HT6, 5-HT7), $\beta$-adrenergic receptors, insulin receptor, leptin receptor, TNF receptor (tissue-necrosis factor), cytokine receptors (IL1-a, IL-b, IL-2, IL-3, IL-4, IL-5, IL-6, IL-7, IL-8, IL-9, IL-10. IL-12, IL-15, IL-18, IL-21, CCR5, CCR7, CXCR4, CCR-1-10, CCL20), statin receptors, FAS receptor, BAFF receptor, FLT3 receptor, GMCSF receptor, and fibronectin receptor.

In a preferred embodiment the activatible element is a cytokine receptor. Cytokines are a family of soluble mediators of cell-to-cell communication that includes interleukins, interferons, and colony-stimulating factors. The characteristic features of cytokines lie in their functional redundancy and pleiotropy. Most of the cytokine receptors that constitute distinct superfamilies do not possess intrinsic protein tyrosine kinase domains, yet receptor stimulation usually invokes rapid tyrosine phosphorylation of intracellular proteins, including the receptors themselves. Many members of the cytokine receptor superfamily activate the Jak protein tyrosine kinase family, with resultant phosphorylation of the STAT transcriptional activator factors. IL-2, IL-4, IL-7 and Interferon γ have all been shown to activate Jak kinases (Frank et al. (1995) Proc. Natl. Acad. Sci. USA 92:7779-7783); Scharfe et al. (1995) Blood 86:2077-2085); (Bacon et al. (1995) Proc. Natl. Acad. Sci. USA 92:7307-7311); and (Sakatsume et al. (1995) J. Biol. Chem. 270:17528-17534). Events downstream of Jak phosphorylation have also been elucidated. For example, exposure of T lymphocytes to IL-2 has been shown to lead to the phosphorylation of signal transducers and activators of transcription (STAT) proteins STAT1α, STAT1β, and STAT3, as well as of two STAT-related proteins, p94 and p95. The STAT proteins were found to translocate to the nucleus and to bind to a specific DNA sequence, thus suggesting a mechanism by which IL-2 may activate specific genes involved in immune cell function (Frank et al. supra). Jak3 is associated with the gamma chain of the IL-2, IL-4, and IL-7 cytokine receptors (Fujii et al., (1995) Proc. Natl. Acad. Sci. 92:5482-5486) and (Musso et al. (1995) J. Exp. Med. 181:1425-1431). The Jak kinases have been shown to be activated by numerous ligands that signal via cytokine receptors such as, growth hormone, erythropoietin and IL-6 (Kishimoto (1994) Stem cells Suppl. 12:37-44).

In a preferred embodiment the activatible element is a member of the nerve growth factor receptor superfamily, such as the Tumor necrosis factor α receptor. Tumor necrosis factor α (TNF-α or TNF-alpha) is a pleiotropic cytokine that is primarily produced by activated macrophages and lymphocytes but is also expressed in endothelial cells and other cell types. TNF-alpha is a major mediator of inflammatory, immunological, and pathophysiological reactions. (Grell, M., et al., (1995) Cell, 83:793-802). Two distinct forms of TNF exist, a 26 kDa membrane expressed form and the soluble 17 kDa cytokine which is derived from proteolytic cleavage of the 26 kDa form. The soluble TNF polypeptide is 157 amino acids long and is the primary biologically active molecule.

TNF-alpha exerts its biological effects through interaction with high-affinity cell surface receptors. Two distinct membrane TNF-alpha receptors have been cloned and characterized. These are a 55 kDa species, designated p55 TNF-R and a 75 kDa species designated p75 TNF-R (Corcoran. A. E., et al., (1994) Eur. J. Biochem., 223:831-840). The two TNF receptors exhibit 28% similarity at the amino acid level. This is confined to the extracellular domain and consists of four repeating cysteine-rich motifs, each of approximately 40 amino acids. Each motif contains four to six cysteines in conserved positions. Dayhoff analysis shows the greatest intersubunit similarity among the first three repeats in each receptor. This characteristic structure is shared with a number of other receptors and cell surface molecules, which comprise the TNF-R/nerve growth factor receptor superfamily (Corcoran. A. E., et al., (1994) Eur. J. Biochem., 223:831-840).

TNF signaling is initiated by receptor clustering, either by the trivalent ligand TNF or by cross-linking monoclonal antibodies (Vandevoorde, V., et al., (1997) J. Cell Biol., 137: 1627-1638). Crystallographic studies of TNF and the structurally related cytokine, lymphotoxin (LT), have shown that both cytokines exist as homotrimers, with subunits packed edge to edge in threefold symmetry. Structurally, neither TNF or LT reflect the repeating pattern of the their receptors. Each monomer is cone shaped and contains two hydrophilic loops on opposite sides of the base of the cone. Recent crystal structure determination of a p55 soluble TNF-R/LT complex has confirmed the hypothesis that loops from adjacent monomers join together to form a groove between monomers and that TNF-R binds in these grooves (Corcoran. A. E., et al., (1994) Eur. J. Biochem., 223:831-840).

In preferred embodiment, the activatible element is a receptor tyrosine kinase. The receptor tyrosine kinases can be divided into five subgroups on the basis of structural similarities in their extracellular domains and the organization of the tyrosine kinase catalytic region in their cytoplasmic domains. Sub-groups I (epidermal growth factor (EGF) receptor-like), II (insulin receptor-like) and the EPH/ECK family contain cysteine-rich sequences (Hirai et al., (1987) Science 238: 1717-1720 and Lindberg and Hunter, (1990) Mol. Cell. Biol. 10:6316-6324). The functional domains of the kinase region of these three classes of receptor tyrosine kinases are encoded as a contiguous sequence (Hanks et al. (1988) Science 241: 42-52). Subgroups III (platelet-derived growth factor (PDGF) receptor-like) and IV (the fibro-blast growth factor (FGF) receptors) are characterized as having immunoglobulin (Ig)-like folds in their extracellular domains, as well as having their kinase domains divided in two parts by a variable stretch of unrelated amino acids (Yanden and Ullrich (1988) supra and Hanks et al. (1988) supra).

The family with by far the largest number of known members is the Eph family (with the first member of the family originally isolated from an erythropoietin producing hepatocellular carcinoma cell line). Since the description of the prototype, the Eph receptor (Hirai et al. (1987) Science 238: 1717-1720), sequences have been reported for at least ten members of this family, not counting apparently orthologous receptors found in more than one species. Additional partial sequences, and the rate at which new members are still being reported, suggest the family is even larger (Maisonpierre et al. (1993) Oncogene 8:3277-3288; Andres et al. (1994) Oncogene 9:1461-1467; Henkemeyer et al. (1994) Oncogene 9:1001-1014; Ruiz et al. (1994) Mech. Dev. 46:87-100; Xu et al. (1994) Development 120:287-299; Zhou et al. (1994) J. Neurosci. Res. 37:129-143; and references in Tuzi and Gullick (1994) Br. J. Cancer 69:417-421). Remarkably, despite the large number of members in the Eph family, all of these molecules were identified as orphan receptors without known ligands.

As used herein, the terms "Eph receptor" or "Eph-type receptor" refer to a class of receptor tyrosine kinases, comprising at least eleven paralogous genes, though many more orthologs exist within this class, e.g. homologs from different species. Eph receptors, in general, are a discrete group of receptors related by homology. and easily recognizable, e.g., they are typically characterized by an extracellular domain containing a characteristic spacing of cysteine residues near the N-terminus and two fibronectin type III repeats (Hirai et al. (1987) Science 238:1717-1720; Lindberg et al. (1990) Mol. Cell Biol. 10:6316-6324; Chan et al. (1991) Oncogene 6:1057-1061; Maisonpierre et al. (1993) Oncogene 8:3277-3288; Andres et al. (1994) Oncogene 9:1461-1467; Henkemeyer et al. (1994) Oncogene 9:1001-1014; Ruiz et al. (1994) Mech. Dev. 46:87-100; Xu et al. (1994) Development 120: 287-299; Zhou et al. (1994) J. Neurosci. Res. 37:129-143; and references in Tuzi and Gullick (1994) Br. J. Cancer 69:417-421). Exemplary Eph receptors include the eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors.

In another embodiment the receptor element is a member of the hematopoietin receptor superfamily. Hematopoietin receptor superfamily is used herein to define single-pass transmembrane receptors, with a three-domain architecture: an extracellular domain that binds the activating ligand, a short transmembrane segment, and a domain residing in the cytoplasm. The extracellular domains of these receptors have low but significant homology within their extracellular ligand-binding domain comprising about 200-210 amino acids. The homologous region is characterized by four cysteine residues located in the N-terminal half of the region, and a Trp-Ser-X-Trp-Ser (WSXWS) motif located just outside the membrane-spanning domain. Further structural and functional details of these receptors are provided by Cosman, D. et al., (1990). The receptors of IL-1, IL-2, IL-3, IL-4, IL-5, IL-6, IL-7, prolactin, placental lactogen, growth hormone GM-CSF, G-CSF, M-CSF and erythropoietin have, for example, been identified as members of this receptor family.

In a further embodiment, the receptor element is an integrin other than Leukocyte Function Antigen-1 (LFA-1). Members of the integrin family of receptors function as heterodimers, composed of various $\alpha$ and $\beta$ subunits, and mediate interactions between a cell's cytoskeleton and the extracellular matrix. (Reviewed in, Giancotti and Ruoslahti, Science 285, 13 Aug. 1999). Different combinations of the $\alpha$ and $\beta$ subunits give rise to a wide range of ligand specificities, which may be increased further by the presence of cell-type-specific factors. Integrin clustering is know to activate a number of intracellular signals, such as RAS, MAP kinase, and phosphotidylinosital-3-kinase. In a preferred embodiment the receptor element is a heterodimer (other than LFA-1) composed of a $\beta$ integrin and an $\alpha$ integrin chosen from the following integrins; $\beta 1$, $\beta 2$, $\beta 3$, $\beta 4$, $\beta 5$, $\beta 6$, $\alpha 1$, $\alpha 2$, $\alpha 3$, $\alpha 4$, $\alpha 5$, and $\alpha 6$, or is MAC-1 ($\beta 2$ and cd11b), or $\alpha V \beta 3$.

In another embodiment the activatible elements cluster for signaling by contact with other surface molecules. In contrast to the receptors discussed above, these elements cluster for signaling by contact with other surface molecules, and generally use molecules presented on the surface of a second cell as ligands. Receptors of this class are important in cell-cell interactions, such mediating cell-to-cell adhesion and immunorecognition.

Examples of such receptor elements are CD3 (T cell receptor complex), BCR (B cell receptor complex), CD4, CD28, CD80, CD86, CD54, CD102, CD50 and ICAMs 1, 2 and 3.

In a preferred embodiment the receptor element is a T cell receptor complex (TCR). TCRs occur as either of two distinct heterodimers, $\alpha \beta$ or $\gamma \delta$, both of which are expressed with the non-polymorphic CD3 polypeptides $\gamma$, $\delta$, $\epsilon$, $\zeta$. The CD3 polypeptides, especially $\zeta$ and its variants, are critical for intracellular signaling. The $\alpha \beta$ TCR heterodimer expressing cells predominate in most lymphoid compartments and are responsible for the classical helper or cytotoxic T cell responses. In most cases, the $\alpha \beta$ TCR ligand is a peptide antigen bound to a class I or a class II MHC molecule (Fundamental Immunology, fourth edition, W. E. Paul, ed., Lippincott-Raven Publishers, 1999, Chapter 10, pp 341-367).

In a preferred embodiment the receptor element is a B cell antigen receptor (BCR). Antigen contact with a specific B cell triggers the transmembrane signaling function of the BCR. BCR molecules are rapidly internalized after antigen binding, leading to antigen uptake and degradation in endosomes or lysosomes. In the case of protein antigens, antigen-derived peptides bind in the groove of class II MHC molecules. Upon binding, this complex is sent to the cell surface, where it serves as a stimulus for specific helper T cells. Antigen recognition by the helper T cell induces it to form a tight and long lasting interaction with the B cell and to synthesize B cell growth and differentiation factors. B cells activated in this way may proliferate and terminally differentiate to antibody secreting cells (also called plasma cells) (Fundamental Immunology, fourth edition, W. E. Paul, ed., Lippincott-Raven Publishers, 1999, Chapters 6-7, pp 183-261)

In a preferred embodiment the element is an intracellular adhesion molecule (ICAM). ICAMs-1, -2, and -3 are cellular adhesion molecules belonging to the immunogloblin superfamily. Each of these receptors has a single membrane-spanning domain and all bind to β2 integrins via extracellular binding domains similar in structure to Ig-loops. (Signal Transduction, Gomperts, et al., eds, Academic Press Publishers, 2002, Chapter 14, pp 318-319).

In another embodiment, the activatible element is a member of the large family of G-protein-coupled receptors. It has recently been reported that a G-protein-coupled receptors are capable of clustering. (Kroeger, et al., J Biol Chem 276:16, 12736-12743, Apr. 20, 2001; Bai, et al., J Biol Chem 273:36, 23605-23610, Sep. 4, 1998; Rocheville, et al., J Biol Chem 275 (11), 7862-7869, Mar. 17, 2000). As used herein G-protein-coupled receptor, and grammatical equivalents thereof, refers to the family of receptors that bind to heterotrimeric "G proteins." Many different G proteins are known to interact with receptors. G protein signaling systems include three components: the receptor itself, a GTP-binding protein (G protein), and an intracellular target protein. The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha (α), beta (β) and gamma (γ) subunits, are complexed with the nucleotide guanosine diphosphate (GDP) and are in contact with receptors. When a hormone or other first messenger binds to a receptor, the receptor changes conformation and this alters its interaction with the G protein. This spurs the α subunit to release GDP, and the more abundant nucleotide guanosine triphosphate (GTP), replaces it, activating the G protein. The G protein then dissociates to separate the α subunit from the still complexed beta and gamma subunits. Either the Gα subunit, or the Gβγ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the Gα converts the GTP to GDP, thereby inactivating itself. The inactivated Gα may then reassociate with the Gβγ complex.

Hundreds, if not thousands, of receptors convey messages through heterotrimeric G proteins, of which at least 17 distinct forms have been isolated. Although the greatest variability has been seen in the α subunit, several different β and γ structures have been reported. There are, additionally, many different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) Cell 72, 415; Kouba et al. FEBS Lett. (1993)321, 173; and Birkenbach et al. (1993) J. Virol. 67, 2209.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, histamine, noradrenaline, tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheromones, galanin, gastric inhibitory polypeptide receptor (gip), glucagon-like peptides (glps), glucagon, gonadotropin releasing hormone (gnrh), growth hormone releasing hormone (ghrh), insect diuretic hormone, interleukin-8, leutropin (1 h/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Preferred G protein coupled receptors include, but are not limited to: α1-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2a adenosine receptor, A2b adenosine receptor, A3 adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor (FPR), fMLP-like receptor (FPRL-1), angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, CXCR1 (IL-8 receptor A), CXCR2 (IL-8 receptor B), Delta Opioid receptor, Kappa Opioid receptor, mip-1alpha/RANTES receptor (CRR1), Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor. In addition, there are at least five receptors (CC and CXC receptors) involved in HIV viral attachment to cells. The two major co-receptors for HIV are CXCR4, (fusin receptor, LESTR, SDF1 receptor) and CCR5 (m-trophic). More preferred receptors include the following human receptors: melatonin receptor 1a, galanin receptor 1, neurotensin receptor, adenosine receptor 2a, somatostatin receptor 2 and corticotropin releasing factor receptor 1. Melatonin receptor 1a is particularly preferred. Other G protein coupled receptors (GPCRs) are known in the art.

In a preferred embodiment the activatible elements are intracellular receptors capable of clustering. Elements of this class are not membrane-bound. Instead, they are free to diffuse through the intracellular matrix where they bind soluble ligands prior to clustering and signal transduction. In contrast to the previously described elements, many members of this class are capable of binding DNA after clustering to directly effect changes in RNA transcription.

In a preferred embodiment the intracellular receptors capable of clustering are peroxisome proliferator-activated receptors (PPAR). PPARs are soluble receptors responsive to lipophilic compounds, and induce various genes involved in fatty acid metabolism. The three PPAR subtypes, PPAR $\alpha$, $\beta$, and $\gamma$ have been shown to bind to DNA after ligand binding and heterodimerization with retinoid X receptor. (Summanasekera, et al., J Biol Chem, M211261200, Dec. 13, 2002.)

In another embodiment the activatible element is a nucleic acid. Activation and deactivation of nucleic acids can occur in numerous ways including, but not limited to, cleavage of an inactivating leader sequence as well as covalent or non-covalent modifications that induce structural or functional changes. For example, many catalytic RNAs, e.g. hammerhead ribozymes, can be designed to have an inactivating leader sequence that deactivates the catalytic activity of the ribozyme until cleavage occurs. An example of a covalent modification is methylation of DNA. Deactivation by methylation has been shown to be a factor in the silencing of certain genes, e.g. STAT regulating SOCS genes in lymphomas. See Leukemia See 2004 February; 18(2): 356-8. SOCS1 and SHP1 hypermethylation in mantle cell lymphoma and follicular lymphoma: implications for epigenetic activation of the Jak/STAT pathway. Chim C S, Wong K Y, Loong F, Srivastava G.

In another embodiment the activatible element is a small molecule, carbohydrate, lipid or other naturally occurring or synthetic compound capable of having an activated isoform. In addition, as pointed out above, activation of these elements need not include switching from one form to another, but can be detected as the presence or absence of the compound. For example, activation of cAMP (cyclic adenosine mono-phosphate) can be detected as the presence of cAMP rather than the conversion from non-cyclic AMP to cyclic AMP.

Potentiation

In one embodiment, the instant invention involves determining the activation profile of cells after the introduction of an environmental cue (e.g. by administering a potentiator). In such an embodiment it is not only the absolute level of activation that is determined, but also the role signalling cascades play in the activation of elements. In general, potentiators are used to alter signaling cascades prior to determination of the activation profile of a cell, and the impact of the potentiator is measured as differences in the activation profile as compared to a non-potentiated cell. For example, by simultaneously measuring multiple phosphorylation events at the single cell level across a complex population of tumor cells, it is possible to build and distinguish pathway anomalies in different cell subsets. Similarly, potentiation can be viewed as "priming" of cells. One example of priming is the development of naïve cells into memory cells. One consequence of this priming is that memory cells respond faster as their thresholds for activation are lower than naïve cells, due to their previous exposure to the priming input.

Key to understanding the role of potentiators in the instant invention is to appreciate the fact that an activation profile of any one cell or population of cells includes the determination of the activation state of one or more different activatible elements. Each of these elements forms a specific node in a signalling cascade or network. As many cellular signalling networks are interconnected, cues that impact one node can have an effect on the ability of other nodes to switch between activation states. Therefore, by investigating the activation state of various nodes in the presence or absence of various potentiators it is possible to determine the underlying network structures interconnecting the nodes and to categorize activation profiles by their impact on such underlying structures. Potentiation and its role in categorizing activation profiles is discussed in detail under the heading "Analysis" below and in Example 2.

As pointed out above, potentiators can take the form of a wide variety of environmental cues and inputs. The defining characteristic of a potentiator is that is a cue or input capable of impacting cellular signalling networks. Examples of potentiators include, but are not limited to, physical parameters such as heat, cold, UV radiation, as well as cytokines, drugs, hormones, antibodies, peptides, and protein fragments, either alone or in the context of cells, cells themselves, viruses, and biological and non-biological complexes (e.g. beads, plates, viral envelopes, antigen presentation molecules such as major histocompatibility complex).

In a preferred embodiment, the potentiator is a cell or cell population. For example, a common pool of normal T cells, thought of as effectors, can be exposed to various tumor cell populations from different patients, and the ability of the tumors to generate different signaling profiles in the effectors (and of the effectors to reciprocally stimulate potentiated signaling in the various tumor cells) can be monitored. Similarly, normal T cells from patients with a disease can be mixed with various tumor cell populations (from the same patient) and the signaling potential (activation events) within the normal T cells and the tumor cells can be profiled. Such assays could take place in a single tube and the relevant cell subpopulations (e.g. effectors and tumor cells) identified using antibodies that recognize cell surface epitopes). Furthermore, these assays could take place under a series of potentiating conditions (e.g. co-stimulation using antibodies).

Detection of State

In general, there are a variety of ways to detect the activation state of a particular protein (i.e. activatible element). In one embodiment, labeled binding elements ("BEs") are used, which bind specifically to one isoform of the protein. Alternatively the state of the activatible protein is used for the readout; for example, in the case of cell surface receptors with signalling domains, the activity (or lack thereof) of the signalling domain can be assayed directly. For example, the two isoforms may be no activity (negative signal) versus kinase activity (measured using chromogenic substrates).

Binding Elements

By "binding element," "BE," and grammatical equivalents thereof, is meant any molecule, e.g., nucleic acids, small organic molecules, and proteins which are capable of detecting one isoform of an element over another.

In a preferred embodiment, the BE is a protein, as used herein, the term "protein" means at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradation. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

In a preferred embodiment, the protein BE is an antibody. In a particularly preferred embodiment, the protein BE is an activation state-specific antibody. Accordingly, the methods and compositions of the present invention may be used to detect any particular element isoform in a sample that is antigenically detectable and antigenically distinguishable from other isoforms of the activatible element that are present in the sample. For example, the activation state-specific antibodies of the present invention can be used in the present methods to identify distinct signaling cascades of a subset or subpopulation of complex cell populations; and the ordering of protein activation (e.g., kinase activation) in potential signaling hierarchies.

By "antibody" herein is meant a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. Antibody herein is meant to include full length antibodies and antibody fragments, and may refer to a natural antibody from any organism, an engineered antibody, or an antibody generated recombinantly for experimental, therapeutic, or other purposes as further defined below. The term "antibody" includes antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. Particularly preferred are full length antibodies that comprise Fc variants as described herein. The term "antibody" comprises monoclonal and polyclonal antibodies. Antibodies can be antagonists, agonists, neutralizing, inhibitory, or stimulatory.

The antibodies of the present invention may be nonhuman, chimeric, humanized, or fully human. For a description of the concepts of chimeric and humanized antibodies see Clark et al., 2000 and references cited therein (Clark, 2000, Immunol Today 21:397-402). Chimeric antibodies comprise the variable region of a nonhuman antibody, for example VH and VL domains of mouse or rat origin, operably linked to the constant region of a human antibody (see for example U.S. Pat. No. 4,816,567). In a preferred embodiment, the antibodies of the present invention are humanized. By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) VL and VH frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). The humanized antibody optimally also will comprise at least a portion of an immunoglobulin constant region, typically that of a human immunoglobulin, and thus will typically comprise a human Fc region. Methods for humanizing non-human antibodies are well known in the art, and can be essentially performed following the method of Winter and co-workers (Jones et al., 1986, Nature 321:522-525; Riechmann et al., 1988, Nature 332:323-329; Verhoeyen et al., 1988, Science, 239:1534-1536). Additional examples of humanized murine monoclonal antibodies are also known in the art, for example antibodies binding human protein C (O'Connor et al., 1998, Protein Eng 11:321-8), interleukin 2 receptor (Queen et al., 1989, Proc Natl Acad Sci, USA 86:10029-33), and human epidermal growth factor receptor 2 (Carter et al., 1992, Proc Natl Acad Sci USA 89:4285-9). In an alternate embodiment, the antibodies of the present invention may be fully human, that is the sequences of the antibodies are completely or substantially human. A number of methods are known in the art for generating fully human antibodies, including the use of transgenic mice (Bruggemann et al., 1997, Curr Opin Biotechnol 8:455-458) or human antibody libraries coupled with selection methods (Griffiths et al., 1998, Curr Opin Biotechnol 9:102-108).

Specifically included within the definition of "antibody" are aglycosylated antibodies. By "aglycosylated antibody" as used herein is meant an antibody that lacks carbohydrate attached at position 297 of the Fc region, wherein numbering is according to the EU system as in Kabat. The aglycosylated antibody may be a deglycosylated antibody, which is an antibody for which the Fc carbohydrate has been removed, for example chemically or enzymatically. Alternatively, the aglycosylated antibody may be a nonglycosylated or unglycosylated antibody, that is an antibody that was expressed without Fc carbohydrate, for example by mutation of one or residues that encode the glycosylation pattern or by expression in an organism that does not attach carbohydrates to proteins, for example bacteria.

Specifically included within the definition of "antibody" are full-length antibodies that contain an Fc variant portion. By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, Cg1, Cg2, and Cg3. In some mammals, for example in camels and llamas, IgG antibodies may consist of only two heavy chains, each heavy chain comprising a variable domain attached to the Fc region. By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3.

As used herein, the term "activation state-specific antibody" or "activation state antibody" or grammatical equivalents thereof, refer to an antibody that specifically binds to a corresponding and specific antigen. Preferably, the corresponding and specific antigen is a specific isoform of an activable element. The binding of the activation state-specific antibody is also preferably indicative of a specific activation state of a specific activatible element. Thus, in preferred embodiments, the binding of an activation state-specific antibody to a corresponding isoform of an activable element is indicative of the identity of that element as well as the activation state of that element.

As pointed out above, activation state specific antibodies can be used to detect kinase activity, however additional means for determining kinase activation are provided by the present invention. For example, substrates that are specifically recognized by protein kinases and phosphorylated thereby are known. Antibodies that specifically bind to such phosphorylated substrates but do not bind to such non-phosphorylated substrates (phospho-substrate antibodies) may be used to determine the presence of activated kinase in a sample.

In a further embodiment, an element activation profile is determined using a multiplicity of activation state antibodies that have been immobilized. Antibodies may be non-diffusibly bound to an insoluble support having isolated sample-receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes, and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. In some cases magnetic beads and the like are included.

The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the antibody on the surface, etc. Following binding of the antibody, excess unbound material is removed by washing. The sample receiving areas may then be blocked through incubation with bovine serum albumin (BSA), casein or other innocuous protein or other moiety.

The antigenicity of an activated isoform of an activatible element is distinguishable from the antigenicity of non-activated isoform of an activatible element or from the antigenicity of an isoform of a different activation state. In a preferred embodiment, an activated isoform of an element possesses an epitope that is absent in a non-activated isoform of an element, or vice versa. In another preferred embodiment, this difference is due to covalent addition of moieties to an element, such as phosphate moieties, or due to a structural change in an element, as through protein cleavage, or due to an otherwise induced conformational change in an element which causes the element to present the same sequence in an antigenically distinguishable way. In another preferred embodiment, such a conformational change causes an activated isoform of an element to present at least one epitope that is not present in a non-activated isoform, or to not present at least one epitope that is presented by a non-activated isoform of the element. In some embodiments, the epitopes for the distinguishing antibodies are centered around the active site of the element, although as is known in the art, conformational changes in one area of an element may cause alterations in different areas of the element as well.

Many antibodies, many of which are commercially available (for example, see Cell Signaling Technology's catalogue, the contents which are incorporated herein by reference) have been produced which specifically bind to the phosphorylated isoform of a protein but do not specifically bind to a non-phosphorylated isoform of a protein. Many such antibodies have been produced for the study of signal transducing proteins that are reversibly phosphorylated. In particular, many such antibodies have been produced which specifically bind to phosphorylated, activated isoforms of protein kinases and are sometimes referred to herein as kinase activation state antibodies or grammatical equivalents thereof. Particularly preferred antibodies for use in the present invention include: phospho-AKT Ser473 monoclonal anti-4E2, phospho-p44/42 MAP kinase (Thr202/Tyr204) monoclonal antibody, phospho-TYK2 (Tyr1054/1055) antibody, phospho-p38 MAP kinase (Thr180/Tyr182) monoclonal antibody 28B10, phospho-PKC-PAN substrate antibody, phospho-PKA-substrate, phospho-SAPK/JNK (Thr183/Tyr185) G9 monoclonal antibody, phospho-tyrosine monoclonal antibody (P-tyr-100), p44/42 MAPK, p38 MAPK, JNK/SAPK, and phospho-AKT-Thr308.

In a preferred embodiment, an epitope-recognizing fragment of an activation state antibody rather than the whole antibody is used. In another preferred embodiment, the epitope-recognizing fragment is immobilized. In another preferred embodiment, the antibody light chain that recognizes an epitope is used. A recombinant nucleic acid encoding a light chain gene product that recognizes an epitope may be used to produce such an antibody fragment by recombinant means well known in the art.

Non-activation state antibodies may also be used in the present invention. In a preferred embodiment, non-activation state antibodies bind to epitopes in both activated and non-activated forms of an element. Such antibodies may be used to determine the amount of non-activated plus activated element in a sample. In another preferred embodiment, non-activation state antibodies bind to epitopes present in non-activated forms of an element but absent in activated forms of an element. Such antibodies may be used to determine the amount of non-activated element in a sample. Both types of non-activation state antibodies may be used to determine if a change in the amount of activation state element, for example from samples before and after treatment with a candidate bioactive agent as described herein, coincide with changes in the amount of non-activation state element. For example, such antibodies can be used to determine whether an increase in activated element is due to activation of non-activation state element, or due to increased expression of the element, or both.

In another preferred embodiment, antibodies are immobilized using beads analogous to those known and used for standardization in flow cytometry. Attachment of a multiplicity of activation state specific antibodies to beads may be done by methods known in the art and/or described herein. Such conjugated beads may be contacted with sample, preferably cell extract, under conditions that allow for a multiplicity of activated elements, if present, to bind to the multiplicity of immobilized antibodies. A second multiplicity of antibodies comprising non-activation state antibodies which are uniquely labeled may be added to the immobilized activation state specific antibody-activated element complex and the beads may be sorted by FACS on the basis of the presence of each label, wherein the presence of label indicates binding of corresponding second antibody and the presence of corresponding activated element.

In alternative embodiments of the instant invention, aromatic amino acids of protein BEs may be replaced with D- or L-naphylalanine, D- or L-phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl)alanines, and D- or L-alkylalanines where alkyl may be substituted or unsubstituted methyl, ethyl, propyl, hexyl, butyl, pentyl, isopropyl, iso-butyl, sec-isotyl, iso-pentyl, and non-acidic amino acids of C1-C20.

Acidic amino acids can be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —SO3H) threonine, serine, or tyrosine.

Other substitutions may include nonnatural hydroxylated amino acids may made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Alkyl includes heteroalkyl, with atoms of nitrogen, oxygen and sulfur. Preferred alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the polypeptides may be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant polypeptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues.

Other suitable reagents for derivatizing alpha-amino-containing residues include compounds such as imidoesters, e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosyl residues per se is well known, such as for introducing spectral labels into tyrosyl residues by reaction with aromatic diazonium compounds or tetranitromethane.

N-acetylimidizol and tetranitromethane may be used to form O-acetyl tyrosyl species and 3-nitro derivatives, respectively. Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

In a preferred embodiment, the activation state-specific BE is a peptide comprising a recognition structure that binds to a target structure on an activatible element. A variety of recognition structures are well known in the art and can be made using methods known in the art, including by phage display libraries (see e.g., Gururaja et al. Chem. Biol. (2000) 7:515-27; Houimel et al., Eur. J. Immunol. (2001) 31:3535-45; Cochran et al. J. Am. Chem. Soc. (2001) 123:625-32; Houimel et al., Int. J. Cancer (2001) 92:748-55, each incorporated herein by reference). Alternatively, combinatorial chemistry methods may be used for producing recognition structures such as polymers with affinity for a target structure on an activable protein (see e.g., Barn et al., J. Comb. Chem. (2001) 3:534-41; Ju et al., Biotechnol. (1999) 64:232-9, each expressly incorporated herein by reference). In an additional embodiment, the recognition structure is an anti-laminin single-chain antibody fragment (scFv) (see e.g., Sanz et al., Gene Therapy (2002) 9:1049-53; Tse et al., J. Mol. Biol. (2002) 317:85-94, each expressly incorporated herein by reference). In a preferred embodiment, the activation state-specific BE comprises the following recognition structure: SKVILFE—random peptide loop—SKVILFE. BEs having such recognition structures can bind with high affinity to specific target structures. Further, fluorophores can be attached to such BEs for use in the methods of the present invention.

In a preferred embodiment the BE is a nucleic acid. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al., Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made. Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

Nucleic acid BEs may be naturally occurring nucleic acids, random nucleic acids, or "biased" random nucleic acids. For example, digests of prokaryotic or eukaryotic genomes may be used as is outlined above for proteins. Where the ultimate expression product is a nucleic acid, at least 10, preferably at least 12, more preferably at least 15, most preferably at least 21 nucleotide positions need to be randomized, with more preferable if the randomization is less than perfect. Similarly, if the ultimate expression product is an protein, at least 5, preferably at least 6, more preferably at least 7 amino acid positions need to be randomized, again, more are preferable if the randomization is less than perfect.

In a preferred embodiment, the BE is a synthetic compound. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

Alternatively, a preferred embodiment utilizes natural compounds, as BEs, in the form of bacterial, fungal, plant and animal extracts that are available or readily produced.

Additionally, natural or synthetically produced compounds are readily modified through conventional chemical, physical and biochemical means. Known pharmacological agents may be subjected to directed or random chemical modifications, including enzymatic modifications, to produce BEs that may be used in the instant invention.

In another preferred embodiment the BE is a small organic compound. BEs can be synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or BEs that can then be used in the present invention.

In a preferred embodiment the BE is a carbohydrate. As used herein the term carbohydrate is meant to include any compound with the general formula $(CH_2O)_n$. Examples of preferred carbohydrates are di-, tri- and oligosaccharides, as well polysaccharides such as glycogen, cellulose, and starches.

In a preferred embodiment the BE is a lipid. As used herein the term lipid herein is meant to include any water insoluble organic molecule that is soluble in nonpolar organic solvents. Examples of preferred lipids are steroids, such as cholesterol, and phospholipids such as sphingomeylin.

Labels

The methods and compositions of the instant invention provide BEs comprising a label or tag. By label is meant a molecule that can be directly (i.e., a primary label) or indirectly (i.e., a secondary label) detected; for example a label can be visualized and/or measured or otherwise identified so that its presence or absence can be known. A compound can be directly or indirectly conjugated to a label which provides a detectable signal, e.g. radioisotopes, fluorescers, enzymes, antibodies, particles such as magnetic particles, chemiluminescers, or specific binding molecules, etc. Specific binding molecules include pairs, such as biotin and streptavidin, digoxin and antidigoxin etc. Preferred labels include, but are not limited to, optical fluorescent and chromogenic dyes including labels, label enzymes and radioisotopes.

Using the example of two activation state specific antibodies, by "uniquely labeled" is meant that a first activation state antibody recognizing a first activated element comprises a first label, and second activation state antibody recognizing a second activated element comprises a second label, wherein the first and second labels are detectable and distinguishable, making the first antibody and the second antibody uniquely labeled.

In general, labels fall into four classes: a) isotopic labels, which may be radioactive or heavy isotopes; b) magnetic, electrical, thermal labels; c) colored, optical labels including luminescent, phosphorous and fluorescent dyes or moieties; and d) binding partners. Labels can also include enzymes (horseradish peroxidase, etc.) and magnetic particles. In a preferred embodiment, the detection label is a primary label. A primary label is one that can be directly detected, such as a fluorophore.

Preferred labels include optical labels such as fluorescent dyes or moieties. Fluorophores can be either "small molecule" fluors, or proteinaceous fluors (e.g. green fluorescent proteins and all variants thereof).

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., Science 263 (5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12): 5408-5417 (1993)), β-galactosidase(Nolan, et al., Proc Natl Acad Sci USA 85(8):2603-2607 (April 1988)) and *Renilla*

WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558). All of the above-cited references are expressly incorporated herein by reference.

Particularly preferred labels for use in the present invention include: Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC are known in the art. Quantitation of fluorescent probe conjugation may be assessed to determine degree of labeling and protocols including dye spectral properties are also well known in the art.

In another preferred embodiment, the fluorescent label is a GFP and, more preferably, a *Renilla, Ptilosarcus*, or *Aequorea* species of GFP.

In a preferred embodiment, a secondary detectable label is used. A secondary label is one that is indirectly detected; for example, a secondary label can bind or react with a primary label for detection, can act on an additional product to generate a primary label (e.g. enzymes), etc. Secondary labels include, but are not limited to, one of a binding partner pair; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. For example, suitable binding partner pairs include, but are not limited to: antigens (such as proteins (including peptides) and small molecules) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. Preferred binding partner pairs include, but are not limited to, biotin (or imino-biotin) and streptavidin, digeoxinin and Abs, and Prolinx™ reagents.

In a preferred embodiment, the binding partner pair comprises an antigen and an antibody that will specifically bind to the antigen. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$ to $10^{-9}$ $M^{-1}$, with less than about $10^{-5}$ to $10^{-9}$ $M^{-1}$ being preferred and less than about $10^{-7}$ to $10^{-9}$ $M^{-1}$ being particularly preferred.

In a preferred embodiment, the secondary label is a chemically modifiable moiety. In this embodiment, labels comprising reactive functional groups are incorporated into the molecule to be labeled. The functional group can then be subsequently labeled (e.g. either before or after the assay) with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or heterobifunctional linkers as are well known (see 1994 Pierce Chemical Company catalog, technical section on cross-linkers, pages 155-200, incorporated herein by reference).

In preferred embodiments, multiple fluorescent labels are employed in the methods and compositions of the present invention. In a preferred embodiment, each label is distinct and distinguishable from other labels.

As will be appreciated in the art antibody-label conjugation may be performed using standard procedures or by using protein-protein/protein-dye crosslinking kits from Molecular Probes (Eugene, Oreg.).

In a preferred embodiment labeled antibodies are used for functional analysis of activatible proteins in cells. In performing such analysis several areas of the experiment are considered: (1) identification of the proper combination of antibody cocktails for the stains (2), identification of the sequential procedure for the staining using the antigens (i.e., the activatible protein) and antibody clones of interest, and (3) thorough evaluation of cell culture conditions' effect on cell stimulation. Antigen clone selection is of particular importance for surface antigens of human cells, as different antibody clones yield different result and do not stain similarly in different protocols. Selection of cell types and optimization of culture conditions is also a critical component in detecting differences. For example, some cell lines have the ability to adapt to culture conditions and can yield heterogeneous responses.

The usage of multicolor, multiparameter flow cytometry requires primary conjugated antibodies at defined fluorophores to protein ("FTP") ratios. It is generally not sufficient to give a range of FTP ratios, but rather it is necessary to quantitate the final product thoroughly as FTP ratios differing in 2 molecules can represent significant decreases in phospho-epitope staining. It is also important to note that each fluorophore's optimal FTP is unique and can differ amongst antibody clones to phospho-epitopes.

In a preferred embodiment, the optimal ratio for any protein fluorophore (i.e. PE, APC, PE-TANDEM CONJUGATES (PE-TR, PE-Cy5, PE-CY5.5, PE-CY7, PE-Alexa colors (PE-AX610, PE-AX647, PE-680, PE-AX700, PE-AX750), APC-TANDEM CONJUGATES APC-AX680, APC-AX700, APC-AX750, APC-CY5.5, APC-CY7), GFP, BFP, CFP, DSRED, and all the derivates of the algae proteins including the phycobilliproteins is 1:1 (one ab to one protein dye).

In additional embodiments, the FTP ratio is 1-6 for internal stains; for AX488 the FTP is preferably 2-5 and more preferably 4; for AX546 the FTP ratio is preferably 2-6 and more preferably 2; for AX594 the FTP ratio is preferably 2-4; for AX633 the FTP is preferably 1-3; for AX647 the FTP ratio is preferably 1-4 and more preferably 2. For AX405, AX430, AX555, AX568, AX680, AX700, AX750 the FTP ratio is preferably 2-5.

Alternatively, detection systems based on FRET, discussed in detail below, may be used. FRET finds use in the instant invention, for example, in detecting activation states that involve clustering or multimerization wherein the proximity of two FRET labels is altered due to activation. In a preferred embodiment, at least two fluorescent labels are used which are members of a fluorescence resonance energy transfer (FRET) pair.

FRET is phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Förster radius (Ro), which is typically 10-100 Å. Changes in the fluorescence emission spectrum comprising FRET pairs can be detected, indicating changes in the number of that are in close proximity (i.e., within 100 Å of each other). This will typically result from the binding or dissociation of two molecules, one of which is labeled with a FRET donor and the other of which is labeled with a FRET acceptor, wherein such binding brings the FRET pair in close proximity. Binding of such molecules will result in an increased fluorescence emission of the acceptor and/or quenching of the fluorescence emission of the donor.

FRET pairs (donor/acceptor) useful in the invention include, but are not limited to, EDANS/fluorescein, IAEDANS/fluorescein, fluorescein/tetramethylrhodamine, fluorescein/LC Red 640, fluorescein/Cy 5, fluorescein/Cy 5.5 and fluorescein/LC Red 705.

In another aspect of FRET, a fluorescent donor molecule and a nonfluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, TAMRA, DABCYL, QSY 7 and QSY 33. Useful fluorescent donor/quencher pairs include, but are not limited to EDANS/DABCYL, Texas Red/DABCYL, BODIPY/DABCYL, Lucifer yellow/DABCYL, coumarin/DABCYL and fluorescein/QSY 7 dye.

The skilled artisan will appreciate that FRET and fluorescence quenching allow for monitoring of binding of labeled molecules over time, providing continuous information regarding the time course of binding reactions.

Preferably, changes in the degree of FRET are determined as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

The ratio-metric fluorescent reporter system described herein has significant advantages over existing reporters for protein integration analysis, as it allows sensitive detection and isolation of both expressing and non-expressing single living cells. In a preferred embodiment, the assay system uses a non-toxic, non-polar fluorescent substrate that is easily loaded and then trapped intracellularly. Modification of the fluorescent substrate by a cognate protein yields a fluorescent emission shift as substrate is converted to product. Because the reporter readout is ratiometric it is unique among reporter protein assays in that it controls for variables such as the amount of substrate loaded into individual cells. The stable, easily detected, intracellular readout eliminates the need for establishing clonal cell lines prior to expression analysis. This system and other analogous flow sorting systems can be used to isolate cells having a particular receptor element clustering and/or activation profile from pools of millions of viable cells.

The methods and composition of the present invention may also make use of label enzymes. By label enzyme is meant an enzyme that may be reacted in the presence of a label enzyme substrate that produces a detectable product. Suitable label enzymes for use in the present invention include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., Previews 247:6-9 (1998), Young, J. Virol. Methods 24:227-236 (1989), which are each hereby incorporated by reference in their entirety.

By radioisotope is meant any radioactive molecule. Suitable radioisotopes for use in the invention include, but are not limited to $^{14}C$, $^{3}H$, $^{32}P$, $^{33}P$, $^{35}S$, $^{125}I$, and $^{131}I$. The use of radioisotopes as labels is well known in the art.

As mentioned, labels may be indirectly detected, that is, the tag is a partner of a binding pair. By "partner of a binding pair" is meant one of a first and a second moiety, wherein the first and the second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Other suitable binding pairs include polypeptides such as the FLAG-peptide [Hopp et al., BioTechnology, 6:1204-1210 (1988)]; the KT3 epitope peptide [Martin et al., Science, 255: 192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)] and the antibodies each thereto. As will be appreciated by those in the art, binding pair partners may be used in applications other than for labeling, as is described herein.

As will be appreciated by those in the art, a partner of one binding pair may also be a partner of another binding pair. For example, an antigen (first moiety) may bind to a first antibody (second moiety) that may, in turn, be an antigen for a second antibody (third moiety). It will be further appreciated that such a circumstance allows indirect binding of a first moiety and a third moiety via an intermediary second moiety that is a binding pair partner to each.

As will be appreciated by those in the art, a partner of a binding pair may comprise a label, as described above. It will further be appreciated that this allows for a tag to be indirectly labeled upon the binding of a binding partner comprising a label. Attaching a label to a tag that is a partner of a binding pair, as just described, is referred to herein as "indirect labeling".

By "surface substrate binding molecule" or "attachment tag" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5 substrate [Field et al., Mol. Cell. Biol., 8:2159-2165 (1988)]; the c-myc tag and the 8F9, 3C7, 6E10, G4, B7 and 9E10 antibody substrates thereto [Evan et al., Molecular and Cellular Biology, 5:3610-3616 (1985)]; and the Herpes Simplex virus glycoprotein D (gD) tag and its antibody substrate [Paborsky et al., Protein Engineering, 3(6):547-553 (1990)]. In general, surface binding substrate molecules useful in the present invention include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin.

Production of antibody-embedded substrates is well known; see Slinkin et al., Bioconj. Chem., 2:342-348 (1991); Torchilin et al., supra; Trubetskoy et al., Bioconj. Chem. 3:323-327 (1992); King et al., Cancer Res. 54:6176-6185 (1994); and Wilbur et al., Bioconjugate Chem. 5:220-235 (1994) (all of which are hereby expressly incorporated by reference), and attachment of or production of proteins with antigens is described above. Calmodulin-embedded substrates are commercially available, and production of proteins with CBP is described in Simcox et al., Strategies 8:40-43 (1995), which is hereby incorporated by reference in its entirety.

As will be appreciated by those in the art, tag-components of the invention can be made in various ways, depending largely upon the form of the tag. Components of the invention and tags are preferably attached by a covalent bond.

The production of tag-polypeptides by recombinant means when the tag is also a polypeptide is described below. Production of tag-labeled proteins is well known in the art and kits for such production are commercially available (for example, from Kodak and Sigma). Examples of tag labeled proteins include, but are not limited to, a Flag-polypeptide and His-polypeptide. Methods for the production and use of tag-labeled proteins are found, for example, in Winston et al., Genes and Devel. 13:270-283 (1999), incorporated herein in its entirety, as well as product handbooks provided with the above-mentioned kits.

Biotinylation of target molecules and substrates is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known (Id.).

Methods for labeling of proteins with radioisotopes are known in the art. For example, such methods are found in Ohta et al., Molec. Cell 3:535-541 (1999), which is hereby incorporated by reference in its entirety.

Production of proteins having tags by recombinant means is well known, and kits for producing such proteins are commercially available. For example, such a kit and its use is described in the QIAexpress Handbook from Qiagen by Joanne Crowe et al., hereby expressly incorporated by reference.

The functionalization of labels with chemically reactive groups such as thiols, amines, carboxyls, etc. is generally known in the art. In a preferred embodiment, the tag is functionalized to facilitate covalent attachment. The covalent attachment of the tag may be either direct or via a linker. In one embodiment, the linker is a relatively short coupling moiety, which is used to attach the molecules. A coupling moiety may be synthesized directly onto a component of the invention and contains at least one functional group to facilitate attachment of the tag. Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer. In a preferred embodiment, the covalent attachment is direct, that is, no linker is used. In this embodiment, the component preferably contains a functional group such as a carboxylic acid that is used for direct attachment to the functionalized tag. It should be understood that the component and tag may be attached in a variety of ways, including those listed above. In a preferred embodiment, the tag is attached to the amino or carboxl terminus of the polypeptide. As will be appreciated by those in the art, the above description of the covalent attachment of a label applies to the attachment of virtually any two molecules of the present disclosure.

In a preferred embodiment, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag will depend on the site of attachment to either a linker, as outlined above or a component of the invention. Thus, for example, for direct linkage to a carboxylic acid group of a protein, amino modified or hydrazine modified tags will be used for coupling via carbodiimide chemistry, for example using 1-ethyl-3-(3-dimethylaminopropyl)-carbodiimide (EDAC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the tag, such as is commercially available for many of the tags described herein.

Alternative Activation State Indicators

An alternative activation state indicator useful with the instant invention is one that allows for the detection of activation by indicating the result of such activation. For example, phosphorylation of a substrate can be used to detect the activation of the kinase responsible for phosphorylating that substrate. Similarly, cleavage of a substrate can be used as an indicator of the activation of a protease responsible for such cleavage. Methods are well known in the art that allow coupling of such indications to detectable signals, such as the labels and tags described above in connection with binding elements. For example, cleavage of a substrate can result in the removal of a quenching moiety and thus allowing for a detectable signal being produced from a previously quenched label.

FACS Analysis

In a preferred embodiment, the present invention provides methods for determining an activatible element's activation profile for a single cell. The methods comprise sorting cells by FACS on the basis of the activation state of at least two activatible elements. BEs (e.g. activation state-specific antibodies) are used to sort cells on the basis of activatible element activation state, and can be detected as described below. Alternatively, non-BE systems as described above can be used in any system described herein.

When using fluorescent labeled components in the methods and compositions of the present invention, it will recognized that different types of fluorescent monitoring systems, e.g., FACS systems, can be used to practice the invention. Preferably, FACS systems are used or systems dedicated to high throughput screening, e.g 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation that has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. In general, known robotic systems and components can be used.

In a preferred embodiment, flow cytometry is used to detect fluorescence. Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4, and Remade et al., Proc. Natl. Sci. USA (2000) 18:553-8, each expressly incorporated herein by reference) as well as confocal microscopy. In general, flow cytometry involves the passage of individual cells through the path of a laser beam. The scattering the beam and excitation of any fluorescent molecules attached to, or found within, the cell is detected by photomultiplier tubes to create a readable output, e.g. size, granularity, or fluorescent intensity.

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety of FACS systems are known in the art and can be used in the methods of the invention (see e.g., WO99/54494, filed Apr. 16, 1999; U.S.S.N. 20010006787, filed Jul. 5, 2001, each expressly incorporated herein by reference).

In a preferred embodiment, a FACS cell sorter (e.g. a FACSVantage™ Cell Sorter, Becton Dickinson Immunocytometry Systems, San Jose, Calif.) is used to sort and collect cells based on their activation profile (positive cells) in the presence or absence of potentiation.

In one embodiment, the cells are first contacted with fluorescent-labeled activation state-specific BEs (e.g. antibodies) directed against specific isoforms of specific activatible elements. In such an embodiment, the amount of bound BE on each cell can be measured by passing droplets containing the cells through the cell sorter. By imparting an electromagnetic charge to droplets containing the positive cells, the cells can be separated from other cells. The positively selected cells can then be harvested in sterile collection vessels. These cell-sorting procedures are described in detail, for example, in the FACSVantage™ Training Manual, with particular reference to sections 3-11 to 3-28 and 10-1 to 10-17, which is hereby incorporated by reference in its entirety.

In another embodiment, positive cells can be sorted using magnetic separation of cells based on the presence of an isoform of an activatible element. In such separation techniques, cells to be positively selected are first contacted with specific binding element (e.g., an antibody or reagent that binds an isoform of an activatible element). The cells are then contacted with retrievable particles (e.g., magnetically responsive particles) that are coupled with a reagent that binds the specific element. The cell-binding element-particle complex can then be physically separated from non-positive or non-labeled cells, for example, using a magnetic field. When using magnetically responsive particles, the positive or labeled cells can be retained in a container using a magnetic filed while the negative cells are removed. These and similar separation procedures are described, for example, in the Baxter Immunotherapy Isolex training manual which is hereby incorporated in its entirety.

In a preferred embodiment, methods for the determination of a receptor element activation state profile for a single cell are provided. The methods comprise providing a population of cells and sorting the population of cells by FACS. Preferably, cells are separated on the basis of the activation state of at least two activatible elements. In a preferred embodiment, a multiplicity of activatible element activation-state antibodies are used to simultaneously determine the activation state of a multiplicity of elements.

In a preferred embodiment, cell sorting by FACS on the basis of the activation state of at least two elements is combined with a determination of other FACS readable outputs, such as the presence of surface markers, granularity and cell size to provide a correlation between the activation state of a multiplicity of elements and other cell qualities measurable by FACS for single cells.

In a preferred embodiment cell sorting is done on the basis of element clustering. In one embodiment element clustering can be identified using a doublet discriminator.

A doublet discriminator is so named because of its initial use in discriminating a doublet of G0 or G1 stage cells from a single G2 or M stage cell. As is well known in the art, cells in the G0 and G1 stages of the cell cycle have a single complement of DNA, while cells in the G2 and M stages have doubled their DNA complement in anticipation of cell division. Accordingly, a FACS machine only detecting the amount of DNA within a cell would not be able to discriminate between a doublet of G0 or G1 stage cells, two cells containing a single complement of DNA each, and a G2 or M stage cell, a single cell containing a double complement of DNA. However, because a doublet discriminator also incorporates cell size detection, as discussed below, the doublet can discriminated from the single G2 or M stage cell as being twice the size, though having the same amount of DNA.

As used herein a doublet discriminator functions by comparing two FACS readable outputs. The first of these two FACS readable outputs is fluorescent intensity. In general, a FACS machine will use a laser to excite fluorochromes and make use of photomultiplier tubes to detect the photons emitted by these fluorochromes. The emitted photons are then converted to a voltage reading, termed the voltage pulse distribution. Fluorescent intensity can be measured either as the maximum intensity of the voltage pulse distribution or by integrating the voltage pulse distribution, rather than only taking the maximum, to give a more precise value. The second FACS readable output necessary for doublet discrimination is signal pulse width. Signal pulse width is a measurement of the time taken for the cell to pass through the laser beam and is commonly termed the "Time of Flight" (TOF). As the TOF is proportional to the size of the cell passing through the laser, with larger cells taking longer time periods to pass through the beam and smaller cells taking shorter time periods, the TOF is also proportional to the surface area of that cell.

The doublet discriminator is effective in detecting element clustering due to the proportionality between signal pulse width and surface area. By normalizing the fluorescent intensity over the cell's surface area, clustering is detected as an increase in intensity per unit of surface area as compared to intensity in a non-clustered state. This normalized fluorescent intensity is then plotted over time to represent an increase or decrease in clustering after a certain event, such as administration of a bioactive agent. An example of detecting clustering using a doublet discriminator is presented below in Example 1.

As will be appreciated, the present invention also provides for the ordering of element clustering events in signal transduction. Particularly, the present invention allows the artisan to construct an element clustering and activation hierarchy based on the correlation of levels of clustering and activation of a multiplicity of elements within single cells. Ordering can be accomplished by comparing the activation state of a cell or cell population with a control at a single time point, or by comparing cells at multiple time points to observe subpopulations arising out of the others.

The present invention provides a valuable method of determining the presence of cellular subsets within cellular populations. Ideally, signal transduction pathways are evaluated in homogeneous cell populations to ensure that variances in signaling between cells do not qualitatively nor quantitatively mask signal transduction events and alterations therein. As the ultimate homogeneous system is the single cell, the present invention allows the individual evaluation of cells to allow true differences to be identified in a significant way.

Thus, the invention provides methods of distinguishing cellular subsets within a larger cellular population. As outlined herein, these cellular subsets often exhibit altered biological characteristics (e.g. activation states, altered response to potentiation) as compared to other subsets within the population. For example, as outlined herein, the methods of the invention allow the identification of subsets of cells from a population such as primary cell populations, e.g. peripheral blood mononuclear cells, that exhibit altered responses (e.g. drug resistance or susceptibility) as compared to other subsets. In addition, this type of evaluation distinguishes between different activation states, altered responses to potentiation, cell lineages, cell differentiation states, etc.

As will be appreciated, these methods provide for the identification of distinct signaling cascades for both artificial and stimulatory conditions in complex cell populations, such a peripheral blood mononuclear cells, or naive and memory lymphocytes.

Additional Techniques

As will be appreciated by one of skill in the art, the instant methods and compositions find use in a variety of other assay formats in addition to FACS analysis. For example, a chip analogous to a DNA chip can be used in the methods of the present invention. Arrayers and methods for spotting nucleic acid to a chip in a prefigured array are known. In addition, protein chips and methods for synthesis are known. These methods and materials may be adapted for the purpose of affixing activation state BEs to a chip in a prefigured array. In a preferred embodiment, such a chip comprises a multiplicity of element activation state BEs, and is used to determine an element activation state profile for elements present on the surface of a cell.

In an alternative embodiment, a chip comprises a multiplicity of the "second set BEs," in this case generally unlabeled. Such a chip is contacted with sample, preferably cell extract, and a second multiplicity of BEs comprising element activation state specific BEs is used in the sandwich assay to simultaneously determine the presence of a multiplicity of activated elements in sample. Preferably, each of the multiplicity of activation state-specific BEs is uniquely labeled to facilitate detection.

In an alternative embodiment confocal microscopy can be used to detect activation profiles for individual cells. Confocal microscopy relies on the serial collection of light from spatially filtered individual specimen points, which is then electronically processed to render a magnified image of the specimen. The signal processing involved confocal microscopy has the additional capability of detecting labeled binding elements within single cells, accordingly in this embodiment the cells can be labeled with one or more binding elements. In preferred embodiments the binding elements used in connection with confocal microscopy are antibodies conjugated to fluorescent labels, however other binding elements, such as other proteins or nucleic acids are also possible.

In an additional embodiment the methods and compositions of the instant invention can be used in conjunction with an "In-Cell Western Assay." In such an assay, cells are initially grown in standard tissue culture flasks using standard tissue culture techniques. Once grown to optimum confluency, the growth media is removed and cells are washed and trypsinized. The cells can then be counted and volumes sufficient to transfer the appropriate number of cells are aliquoted into microwell plates (e.g., Nunc™ 96 Microwell™ plates). The individual wells are then grown to optimum confluency in complete media whereupon the media is replaced with serum-free media. At this point controls are untouched, but experimental wells are incubated with a bioactive agent, e.g. EGF. After incubation with the bioactive agent cells are fixed and stained with labeled antibodies to the activation elements being investigated. Once the cells are labeled, the plates can be scanned using an imager such as the Odyssey Imager (LiCor, Lincoln Nebr.) using techniques described in the Odyssey Operator's Manual v1.2., which is hereby incorporated in its entirety. Data obtained by scanning of the multiwell plate can be analysed and activation profiles determined as described below.

Types of Bioactive Candidates that can be Used

In a preferred embodiment, the invention provides methods for screening for a bioactive agent capable of modulating element activity. For example, drugs and drug candidates can be screened to either evaluate the effect of the drug/candidate on activation profiles, or to create desired profiles. The methods comprise contacting a cell with a candidate bioactive agent and determining element activation in said cell using the techniques outlined herein, including FACS.

In a preferred embodiment, the method comprises contacting a plurality of cells with a plurality of candidate bioactive agents and sorting the cells by FACS on the basis of the activation of at least one element.

By "candidate bioactive agent", "candidate agent", "candidate modulator", "candidate modulating agent", or "exogeneous compound" or grammatical equivalents herein is meant any molecule, e.g., protein, small organic molecule, carbohydrates (including polysaccharides), polynucleotide, lipids, etc. Specifically included in the definition of candidate bioactive agent are drugs. Generally a plurality of assay mixtures can be run in parallel with different agent concentrations to obtain a differential response to the various concentrations. Typically, one of these concentrations can serve as a negative control, i.e., at zero concentration or below the level of detection. In addition, positive controls can be used.

Candidate agents encompass numerous chemical classes. In a preferred embodiment, the candidate agents are small molecules. In another preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate agents are obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

In a preferred embodiment, candidate agents are synthetic compounds, as described above in connection with binding elements. One advantage of the present method is that it is not necessary to characterize the candidate agent prior to the assay. Using the methods of the present invention, any candidate agents can be screened for the ability to modulate (e.g., increase or decease) the activity of an activatible element. In addition, as is known in the art, coding tags using split synthesis reactions may be used to essentially identify the chemical moieties tested.

Alternatively, a preferred embodiment utilizes libraries of natural compounds, as candidate agents, in the form of bacterial, fungal, plant and animal extracts that are available or readily produced.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate agents include proteins, nucleic acids, and chemical moieties.

In a preferred embodiment, the candidate agents are proteins, as defined above. In a preferred embodiment, the candidate agents are naturally occurring proteins or fragments of naturally occurring proteins. Thus, for example, cellular extracts containing proteins, or random or directed digests of proteinaceous cellular extracts, may be tested, as is more fully described below. In this way libraries of prokaryotic and eukaryotic proteins may be made for screening against any number of candidate agents. Particularly preferred in this embodiment are libraries of bacterial, fungal, viral, and mammalian proteins, with the latter being preferred, and human proteins being especially preferred.

In a preferred embodiment, the candidate agents are peptides of from about 2 to about 50 amino acids, with from about 5 to about 30 amino acids being preferred, and from about 8 to about 20 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

The library should provide a sufficiently structurally diverse population of randomized agents to effect a probabilistically sufficient range of diversity to allow interaction with a particular activatible protein. Accordingly, an interaction library must be large enough so that at least one of its members will have a structure that interacts with an activatible protein or other specific components of the signal transduction pathway involving the activatible protein. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for a target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, when the candidate agent is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from *Xenopus*, can have potent anti-tumor and anti-microbial activity. Short peptide fragments of a protein kinase C isozyme (βPKC), have been shown to block nuclear translocation of βPKC in *Xenopus* oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate modulators as well.

Thus, a number of molecules or protein domains are suitable as starting points for the generation of biased randomized candidate modulators. A large number of small molecule domains are known, that confer a common function, structure or affinity. In addition, as is appreciated in the art, areas of weak amino acid homology may have strong structural homology A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, and Traf.

In a preferred embodiment, the candidate modulating agent is a polypeptide. In another preferred embodiment, the polypeptide is a cyclic peptide having at least 4 to 20 amino acids. Also in another preferred embodiment, the polypeptide is a catalytically inactive polypeptide. Examples of catalytically inactive polypeptides include, but are not limited to, catalytically inactive activatible proteins and, more specifically a catalytically inactive kinases (e.g., PI3K) or caspases. In a further aspect, the candidate modulating agent is peptide fragment of an activatible protein, wherein the peptide fragment comprises an amino acid sequence that is a subsequence of the full-length amino acid sequence of the activatible protein.

In a preferred embodiment, the candidate agents are nucleic acids as described above in connection with binding elements.

In a preferred embodiment, the candidate agents are organic moieties as described above in connection with binding elements.

As will be appreciated by those in the art, it is possible to screen more than one type of candidate agent at a time, e.g., by combining the candidate agents in the methods of the present invention. Thus, the library of candidate agents used may include only one type of agent (i.e. peptides), or multiple types (peptides and organic agents).

General Screening Methods

In a generalized protocol for determining an activation profile, cells are initially suspended in a small volume of media. The cells can then be aliquoted into a multiwell plate or other appropriate substrate and can be incubated in the presence or absence of a bioactive agent. After incubation is allowed to continue for an appropriate time and at an appropriate temperature the incubation can be terminated and the cells can be fixed as is well known in the art.

Once fixed, the cells can be pelleted and resuspended in methanol to permeabilize, although other methods of permeabilization are also compatible with the instant invention. Cells can be stored at this point or combined with labeled binding elements and analyzed right away.

By "combined" is meant the combining of the various components in a reaction mixture in vitro or in a cell in vivo under conditions which promote an activity that is detectable using known methods or using the methods of the present invention (e.g., the binding of an antibody to a corresponding antigen or isoform of an activatible protein, or activation state of an activatible protein).

Analysis begins by creating a response panel. The response panel is approximated in a two dimensional array of nodes (in rows) and states (in columns), similar to the experimental layout of the multiwell plate. The nodes correspond to each of the proteins being studied in the profile. Other response panels having other characteristics can also find use in the instant invention. The response panels represent the FACS (or other detection method) output for each sample from the multiwell plate. Typically, the log 2 of [MFI stimulated/MFI unstimulated] is taken, however other normalization methodologies are known and can be used in conjunction with the instant invention. For basal nodes, the log 2 of [MFI basal x/MFI sample minimum basal] can be used to place measurements on the same scale. In order to identify an activation profile, the node states for all samples are collected and the variance across samples is studied. When multiple timepoints are included, each timepoint of a sample can be treated as a separate sample. Those node states with variance greater than that seen in a normal cell are typically included in the activation profile.

As discussed above, the instant invention provides methods and compositions for the detection of the activation of elements in cells. As used herein the term cells and grammatical equivalents herein in meant any cell, preferably any prokaryotic or eukaryotic cell.

Suitable prokaryotic cells include, but are not limited to, bacteria such as *E. coli*, various *Bacillus* species, and the extremophile bacteria such as thermophiles, etc.

Suitable eukaryotic cells include, but are not limited to, fungi such as yeast and filamentous fungi, including species of *Aspergillus, Trichoderma*, and *Neurospora*; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tulapia, tuna, carp, flounder, halibut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

Suitable cells also include those cell types implicated in a wide variety of disease conditions, even while in a non-diseased state. Accordingly, suitable eukaryotic cell types include, but are not limited to, tumor cells of all types (particularly melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Particularly preferred are primary disease state cells, such as primary tumor cells. Suitable cells also include known research cells, including, but not limited to, Jurkat T cells, NIH3T3 cells, CHO, COS, etc. See the ATCC cell line catalog, hereby expressly incorporated by reference.

In a preferred embodiment the cells used in the present invention are taken from a patient. As used herein "patient" refers to both human and other animals as well as other organisms, such as experimental animals. Thus the methods and compositions are applicable to both human and veterinary applications. In a preferred embodiment the patient is a mammal, and in a more preferred embodiment the patient is human.

Screening of Agents in the Potentiated Model

In a generalized protocol for study of potentiation, cells (e.g. including but not limited to any cell type described above in connection with the general screening methods) are initially suspended in a small volume of media and counted. An appropriate amount of viable cells from each should be present in the sample (for four core stains), plus an appropriate amount for each stored sample. Cells are then diluted to an appropriate concentration, and an appropriate volume of each is aliquoted into a multiwell plate or other appropriate substrate, as shown below (See Example 3). Potentiators are then added an appropriate concentration and volume into each column of cells. Potentiation is allowed to continue for an appropriate time and at an appropriate temperature. To end potentiation, cells can be washed to remove the potentiator. Potentiatied cells can then be incubated with a bioactive agent in order to screen the effects of that agent. Exposure to the agent can be terminated at various time points by fixing the cells as is known in the art.

After potentiation, the cells can be pelleted and resuspended in methanol to permeabilize, although as discussed above, other methods of permeabilization are also compatible with the instant invention. Cells can be stored at this point or incubated with labeled binding elements and analyzed right away.

Analysis proceeds as described above, including the creation of a response panel, normalization of the nodes, and variances calculated.

Once the nodes have been normalized and the variances determined, unsupervised clustering of biosignature node states is used to group samples. Distribution of clinical parameters in resulting groups is determined using statistical significance testing (e.g. Chi Squared and Student's t-test on previously defined hypotheses). Groups of samples with similar potentiation can then be given designations and pathway maps, based on all possible pathway interactions observed, can be highlighted and dimmed according to observations of each group. In general, if more than half the samples in the group display potentiation above the median for all samples, then that pathway is highlighted. Otherwise, the pathway is dimmed.

Pathway maps can be built out for individual samples based on their observed potentiation, and based on these maps a sample can be phenotyped as belonging to a group (and will be predicted to have similar characteristics as that group). Once a predictive panel for is made for a group, it can be validated on an additional set of samples similar to the original. With the additional data, the map can be minimized and optimized to be as accurate as possible with as few as possible node state measurements for a given sample.

Analysis

Advances in flow cytometry have enabled the individual cell enumeration of up to thirteen simultaneous parameters (De Rosa et al., 2001) and are moving towards the study of genomic and proteomic data subsets (Krutzik and Nolan, 2003; Perez and Nolan, 2002). As the number of parameters, epitopes, and samples have increased, the complexity of flow cytometry experiments and the challenges of data analysis have grown rapidly. An additional layer of data complexity has been added by the development of stimulation panels which enable the study of signal transduction nodes under a growing set of experimental conditions. In order to deal with the resulting experimental and informatics challenges, the instant invention provides techniques of arraying flow cytometry experiments and approximating the results as fold changes using a heat map to facilitate evaluation.

There are a large number of useful ways that flow cytometry experiments can be displayed, such as arraying. Generally speaking, arrayed flow cytometry experiments simplify multidimensional flow cytometry data based on experimental design and observed differences between flow cytometry samples. One common way of comparing changes in a set of flow cytometry samples is to overlay histograms of one parameter on the same plot. Arrayed flow cytometry experiments ideally contain a control population of unstained, control stained, or unstimulated cells against which experimental samples are compared. This control is placed in the first position of the array, and subsequent experimental samples follow the control in the sequence. However, large numbers of histograms or sets of 2D flow cytometry plots can be unwieldy.

Differences between experimental samples can be highlighted by coloring the peaks relative to the change in median fluorescence index (MFI) of each sample. The change from this basal state is calculated as:

$$x' = \log_2\left(\frac{x_{experimental}}{x_{basal}}\right)$$

[Equation 1-1, change of node state from basal]

In Equation 1-1, the fold change for a parameter (e.g., protein phosphorylation, protein expression level) is represented by the change between an experimental, stimulated (e.g. potentiated) MFI and a control MFI, such as the MFI of the same cells without stimulation. Because the $\log_2$ of the change is taken, increases are positive values, decreases are negative values, and small changes are close to zero. To clearly convey the results of an experiment, the same color values can be arrayed according to the experimental design. In an experiment of this relatively small size, the advantage of an arrayed approach is less obvious, and it is the expansion of this technique to a large number of targets, samples, timepoints, and cell subsets that has driven the development of arrayed flow cytometry.

A specific example is useful in describing these aspects of the instant invention. The target phospho-protein in this example, Stat1, is termed a signaling node, and the stimulation conditions under which it is studied are termed node states. This general language is useful for arrayed flow cytometry experiments because it describes diverse cell signaling mechanisms. Thus, mechanisms by which intracellular signals traverse the cell, including phosphorylation, proteolytic cleavage, ubiquitinylation, acetylation, expression level and other post-translational protein states. Flow cytometry assays are described to monitor each of these events and thus numerous proteomic events can be mapped simultaneously in single cells.

Arraying several signal transduction nodes under a common set of conditions, which results in a response panel, provides a two dimensional profile of a target cell population. In this particular example the signaling of six phospho-proteins in the U937 cell line are compared. These phospho-proteins can be assayed simultaneously in individual cells or assayed sequentially in replicate samples. In this way every channel of multiparameter data can be compared simultaneously and samples analyzed in parallel can be combined and compared. This technique is especially useful when moving a well-developed series of assays into a model where each sample will be profiled uniformly (e.g., patient samples). By subtracting the responses in one panel from another sample, or a universal control, a researcher can quickly identify the remaining signaling mechanisms that differ between the two samples.

Arrayed flow cytometry can also be used to screen individual or combined stimulations for a fixed set of signaling nodes. In a plate-based arrayed flow cytometry experiment, the rows and columns represent a grid of stimulation conditions being tested for a response. Each well in a plate might contain the same cells which, as a population, function as a signal transduction test tube. Stimuli are given at x, y coordinates and, following a set time of stimulation, the cells are fixed and each set of cells stained simultaneously for the same set of multiple targets. The natural formatting of arrayed flow cytometry experiments in 96-well plates carries several advantages. Equipment allowing multichannel addition of reagents lowers experimental error, enforces uniformity, and makes it possible to start and stop in tandem a large number of biochemical experiments with short time frames.

In another example of arrayed flow cytometry, signaling mechanisms in peripheral blood leukocytes (PBL) are compared at four minute timepoints following potentiation with phorbol 12-myristate 13-acetate (PMA)/ionomycin. Cells were stained with a surface marker for myeloid lineage cells (CD33) and phosphorylation of four signaling proteins (p38, Stat1, and p53). Signaling was initiated sequentially in a reverse timecourse, and all samples were fixed and stained in unison. Particularly striking in this experiment is that the response of some phospho-proteins is only revealed when a subset of cells is analyzed separately from the background of quiescent non-responders. This result would have been extremely difficult to obtain using classical, mono-parameter technologies for analysis of phospho-proteins (e.g., Western blotting), and would have likely involved physical isolation of myeloid cells from total PBL, a process which can disrupt intracellular signaling.

In order to clarify the differences between experimental samples and controls, MFI changes are approximated as a $\log_2$ fold change. Enumerating signal transduction events in this way makes flow cytometry data portable to statistical methods and clustering algorithms. (Note that the use of the term "clustering" in this context is different from receptor clustering; this context refers to algorithms that cluster data points together in any number of ways. Additionally, cross-platform comparison of samples can be performed when diverse parameters are placed on a similar fold induction scale (e.g., protein expression, RNA content, DNA content and cell cycle representation, protein phosphorylation under diverse conditions, length of repeated genetic elements, patient survival time, cell death following ex vivo stimulation).

Once a vital set of parameters is identified, unsupervised clustering of samples with similar profiles provides a powerful way to identify groups and relationships within a population of samples. According to conventions developed by DNA microarray biologists, populations from flow cytometry can be arranged where each cell or sample of interest is placed in a column and each parameter of interest is placed in a row, analogous to experiments and genes. Once the appropriate populations and parameters have been entered, a number of clustering techniques can be done. Generally, successful use of unsupervised clustering relies on parameters of interest being intelligently chosen, or selected using an algorithm as with variance mapping (see below), such that most or all factors being clustered are important to the group of samples being clustered. This is because unsupervised clustering groups samples solely based on similarities in the values reported for each signaling node state. This technique carries the risk that the groups identified this way might not be clinically relevant, but provides a strong incentive because potentially artificial, pre-organized groups are avoided. As outlined below this approach was used to identify signaling pathologies in acute myeloid leukemia. Compounds with specific activity on a fixed system can also be identified easily using this approach.

Prior to clustering of flow cytometry data, the populations of interest and the method for characterizing these populations are determined. In arrayed flow cytometry there are at least two general ways of identifying populations for clustering:

1. "Outside-in" comparison of parameter sets for individual samples or subset (e.g., patients in a trial). In this more common case, cell populations are homogenous or lineage gated in such a way as to create distinct sets considered to be homogenous for targets of interest. An example of sample-level comparison would be the identification of signaling profiles in the tumor cells of a patient and correlation of these profiles with non-random distribution of clinical responses. This is considered an outside-in approach because the population of interest is pre-defined prior to the mapping and comparison of its profile to other populations.

2. "Inside-out" comparison of parameters at the level of individual cells in a heterogeneous population. An example of this would be the signal transduction state mapping of mixed hematopoietic cells under certain conditions and subsequent comparison of computationally identified cell clusters with lineage specific markers. This could be considered an inside-out approach to single cell studies as it does not presume the existence of specific populations prior to classification. A major drawback of this approach is that it creates populations which, at least initially, require multiple transient markers to enumerate and may never be accessible with a single cell surface epitope. As a result, the biological significance of such populations can be difficult to determine. The main advantage of this unconventional approach is the unbiased tracking of cell populations without drawing potentially arbitrary distinctions between lineages or cell types.

Each of these techniques capitalizes on the ability of flow cytometry to deliver large amounts of multiparameter data at the single cell level. For cancer, a third "meta-level" of tumor data exists because tumors are generally treated as a single entity and classified according to historical techniques. These techniques have included organ or tissue of origin, degree of differentiation, proliferation index, metastatic spread, and genetic or metabolic data regarding the patient.

In addition, the present invention provides variance mapping techniques for mapping tumor signalling space. These methods represent a significant advance in the study of tumor biology because it enables comparison of tumors independent of a putative normal control. Traditional differential state analysis methods (e.g., DNA microarrays, subtractive Northern blotting) generally rely on the comparison of tumors from each patient sample with a normal control, generally adjacent and theoretically untransformed tissue. Alternatively, they rely on multiple clusterings and reclusterings to group and then further stratify patient samples according to phenotype. In contrast, variance mapping of tumor states compares tumor samples first with themselves and then against the parent tumor population. As a result, node states with the most diversity among tumors provide the core parameters in the differential state analysis. Given a pool of diverse tumors, this technique allows a researcher to identify the molecular events that underlie differential tumor pathology (e.g., tumor responses to chemotherapy), as opposed to differences between tumors and a proposed normal control.

The variance ($\sigma^2$) is one way can be represented the diversity of states observed for a node across a set of tumor samples. For arrayed flow cytometry experiments the variance of a node state is calculated as the average squared deviation of each sample's measurement from the mean of the sample set:

$$\sigma^2 = \frac{\sum (x - \bar{x})^2}{N}$$

[Equation 1-2, variance of a node state]

In Equation 1-2, x is each sample's $\log_2$ fold node state measurement, $\bar{x}$ is the average of x across all samples, and N is the number of samples. Parameters where node state measurements vary frequently and by large amounts will have the highest variance. One area for refinement using this technique is in the comparison of diverse parameters that may not always report similar differences in MFI for technical reasons. The MFI shift for a node state can be lowered due to poor fluorophore labeling of a BE or high BE staining background. These issues generally reduce the variance of a node state, causing potentially significant information to be overlooked. In performing clinical profiling of node states, it is important to work with well characterized reagents and to compare nodes and their states on similar scales.

When variance mapping is used to profile the signaling space of patient samples, tumors whose signaling is perturbed in similar ways are grouped together, regardless of tissue or cell type of origin (see profiling of AML). Similarly, two tumors that are thought to be relatively alike based on lineage markers or tissue of origin could have vastly different abilities to interpret environmental stimuli and would be profiled in two different groups. What we have found with this technique is that the potentiated signaling of acute myeloid leukemia tumor samples is predictive of the patient response to cytotoxic chemotherapy (see profiling of AML). A set of normal tissues generally display low variance when profiled with the same technique ($\sigma^2 < 0.1$). Some variance detected in normal tissues could be reflective of subclinical pathology, as the technique would be expected to detect perturbations to individual cell signaling from immune responses and infections. These observations suggested a working variance threshold for informative node states in arrayed flow cytometry experiments ($\sigma^2 = 0.1$). This variance threshold indicates that arrayed flow cytometry is extremely sensitive, and advances in precision will further lower background noise and enable lower values for this threshold. In tumors, the variance for many node states is well above the threshold (median $\sigma^2$ for significant nodes in profiling of AML was 0.34). These results show that variance mapping of tumor signaling detects significant differences in the evolution of tumor signaling networks.

When clusters of signaling profiles have been identified it is frequently useful to determine whether other factors, such as clinical responses, presence of gene mutations, and protein expression levels, are non-randomly distributed within the groups. If experiments or literature suggest such a hypothesis in an arrayed flow cytometry experiment, it can be judged with simple statistical tests, such as the Student's t-test and the $\chi^2$ test. Similarly, if two variable factors within the experiment are thought to be related, the $r^2$ correlation coefficient from a linear regression is used to represent the degree of this relationship. Each of these tests is used to evaluate arrayed flow cytometry data as outlined below, and their appropriate use in analysis of a pool of tumor patient samples is introduced here.

Many hypotheses that are tested in arrayed flow cytometry experiments ask whether the values of a flow cytometry node state are significantly different between two groups. To ask whether the means from two populations are significantly different, a Student's t-test is an appropriate way of obtaining a p-value. For example, as shown in the Examples below, we test the hypothesis that an increased response of Stat3 to G-CSF is found in patient samples with mutations in the Flt3 gene. The Student's t-test is most frequently used in such cross-platform comparisons of arrayed flow cytometry data with other parameters. The t-value for such a test is calculated:

$$t\text{-value} = \left| \frac{\bar{x}_A - \bar{x}_B}{\sqrt{\left(\frac{s_A}{N_A}\right) + \left(\frac{s_B}{N_B}\right)}} \right|$$

[Equation 1-3, $t$-value for two means]

In Equation 1-3, $\bar{x}_A$ is the mean of a node state across group A, $s_A$ is the standard deviation of the node states across group A, and $N_A$ is the number of samples in group A. The denominator of Equation 1-2 is also referred to as the standard error. Together with the degrees of freedom (df), in this case is N−2, the t-value is used to look up the p-value for the hypothesis in a statistical table. In cases where the samples are organized into discrete groups (e.g., "mutation positive" and "mutation negative") for both parameters being compared it is appropriate to use a $\chi^2$ test to determine a p-value. This test is most common when comparing factors within signaling profile derived cluster groups, such as the presence or absence of gene mutation among samples with a specific signaling profile. A p-value calculated with a $\chi^2$ test represents the degree to which a parameter was non-randomly distributed among the groups. The $\chi^2$ value for a set of parameters (p1, p2, p3, . . . ) for two groups (A and B) is calculated by comparing the observed distribution to the expected distribution. The expected distribution for parameter p1 in group A ($E_A^{p1}$) is calculated as:

$$E_A^{p1} = \left( \frac{O_A^{p1} + O_B^{p1}}{N} \right) \sum O_A$$

[Equation 1-4, expected distribution for $p1$ in $A$]

In Equation 1-4, $O_A^{p1}$ is the observed number of p1 samples in group A, N is the total number of samples being compared, and $\Sigma O_A$ is the total number of samples observed in group A. The expected value calculated in Equation 1-2 is used with the observed value to calculate the $\chi^2$ value:

$$X^2 = \sum \frac{(O-E)^2}{E}$$

-continued

[Equation 1-5, $X^2$ test for an observed distribution]

The sum in Equation 1-5 is performed across all possible combinations of parameters and groups. The resulting $\chi^2$ value and the degrees of freedom (in this simple case, the number of parameters) are then used to look up the p-value in a statistical table.

Generally, a p-value is considered significant when it is below a threshold value of $\alpha$=0.05, indicating that the chance of the observed effect taking place randomly was less than one in twenty. A p-value that is equal to or less than 0.001 is generally taken to indicate the observation is extremely significant. However, in some tests the threshold value must be corrected. A potential danger of t-tests arises when multiple t-tests are performed without first designating a hypothesis. For example, sometimes researchers split tumor patient groups into groups (e.g., "tumor" and "normal" or "tumor A" and "tumor B") and then test the significance of many parameters (e.g., expression of 5,000 genes) to each of these groups. In this case, the probability that the averages for any one gene would appear different due to chance has increased with each gene being tested, and the $\alpha$-value should be scaled accordingly. If the alpha value is not scaled, one may observe false positives present among actual hits with higher p-values.

One straightforward way to scale an $\alpha$-value is to divide it by the number of parameters or hypotheses being tested. Therefore, if 5,000 factors were tested simultaneously within two groups, the significance threshold should be set at the much more stringent value of $\alpha$=0.00001. Other solutions to this issue employ groups of genes as hypothesis units, lowering the number of tests, and the testing of pre-existing hypotheses. We adapted our profiling methods to avoid the perils of multiple t-tests by using variance mapping and unsupervised clustering (see AML profiling). Once groups are identified in this way, a $\chi^2$ test can be used to determine whether individual parameters (e.g., chemotherapy response) were non-randomly distributed among the groups. In addition, following identification of signaling profiles using variance mapping, t-tests can be appropriately employed to determine the significance of individual hypotheses, such as the basal and potentiated activity of Stat5 in Flt3 wild type and mutant patient samples (see AML profiling).

A desired outcome in many arrayed flow cytometry experiments is the determination of how a network of signaling molecules function together to regulate cellular processes such as apoptosis and proliferation. A powerful technique for visualizing multidimensional information employs self-organizing maps (SOMs) to sketch a picture for the researcher of relationships between parameters—in the present invention, signal transduction node states. A basic algorithm to map relationship space among parameters begins by determining the square of the Pearson product momentum correlation coefficient (r) between the parameters in the analysis:

$$r = \frac{N \sum (XY - (\sum X)(\sum Y))}{\sqrt{([N \sum X^2 - (\sum X)^2][N \sum Y^2 - (\sum Y)^2])}}$$

[Equation 1-6, Pearson coefficient]

In the application of Equation 1-5 to arrayed flow cytometry, X and Y are the fold MFI values from two node states for which the relationship is being calculated, N is the number of samples, and the sum takes place for all values in the set of samples. Those relationships that are above a significance threshold ($r^2 > 0.5$) are then used as a measure of relationship distance between the signaling nodes. Each related node is placed, with some elasticity, at a distance of $1-r^2$ from the nodes to which it is related. This technique has been used to map the relationships between a set of leukemia nodes: Bcl-2 expression, p53 accumulation, and five p53 phosphorylations (unpublished work of Jonathan Irish). This technique provides an intuitive map of signaling as a network of related nodes or node-states. SOMs are a powerful tool for hypothesis generation and data visualization, but should not be taken to indicate causality. A continuing goal for arrayed flow cytometry SOMs is to represent clearly nodes and node states on different levels of the analysis while still preserving the relationships between states.

Arrayed flow cytometry analysis of leukemia patient samples indicates that primary tissue samples differ strikingly from cells adapted to grow in culture. In moving to a primary cell assay for signal transduction, we were surprised to find that primary tumor cells are not necessarily constitutively dysregulated, as was suggested by many years of literature on the subject (Benekli et al., 2002; Gouilleux-Gruart et al., 1997; Spiekermann et al., 2002). Instead, we understand now that tumor cells have developed signaling responses reflective of increased proliferation, inhibition of apoptosis, and other tumor escape mechanisms. These pathways, which are revealed with environmental cues, are considered "potentiated." Evaluating both basal and potentiated states of signal transduction nodes is a preferred method to elucidate tumor signaling pathology (see AML profiling).

With the development of response panels and a potentiated model of signaling we have found it useful to develop new language to describe the landscape of cell signaling. In addition, such pathological signaling phenotypes can be used to classify human disease, stratify patient risk, and, ultimately, to target disease therapies to patient groups in whom they will be most effective. This generalized model of potentiated signaling outlines a central driving force behind the selective pressures that create tumors: gain proliferative signals without triggering cell death. In acute myeloid leukemia, such proliferative signals take the form of potentiated responses of Stat5 to the myeloid cytokines G-CSF, GM-CSF, and IL-3, and of Flt3 effectors to Flt3-ligand (see AML profiling), and a loss of apoptosis is achieved through Bcl-2 family member expression, loss of Stat1 signaling, changes in p38 MAPK regulation, and suppression of p53 activity (Jonathan Irish, unpublished data). The responses of these signaling nodes to environmental cues (e.g. potentiation) are very useful in the identification of a tumor profile that was clinically relevant. Thus, the present invention shows that tumor cells that resist chemotherapy contain latent signals that are activated by environmental cues. Therefore, understanding dysregulated tumor signaling mechanisms can include evaluation of the expression levels of oncogenes and tumors suppressors, as well as the capacity of signaling molecules to become active.

There are several logical conclusions that can be derived from the three classes of node states outlined in the potentiated model. Potentiation of a node state among a group of cells or samples is relative to an experimentally defined control group, such as a set of samples where the node is non-potentiated or differently potentiated. The definition of the basal node state is relative to the experimental conditions and reflects the possibility that there may be unexpected factors affecting what is considered to be the basal state. Put another way, this model of tumor cell signaling requires an internal control for every node in every sample's profile. As a practical result, a large portion of sample to sample variability is removed from response panel profiles of potentiated signaling. Furthermore, under the potentiated model of tumor signaling a set of experimental samples can be compared not only against a putative normal set, but also against other tumors that display different signaling phenotypes. This is especially important when the normal population is rare, was not obtained from a patient along with the tumor, or when it is unclear what a normal precursor would be for a particular tumor. As shown below (see AML profiling), this type of potentiated signaling model allows definition of tumor groups solely by differences in cell signaling.

Another deduction that can be made, based on the potentiated model, is if a node state in all or nearly all samples or cells reacts to a given environmental cue in the same way, then it is not potentiated, despite its ability to be responsive. While counterintuitive, it is an important component of the potentiated model. Practically, this means that to describe a node state as potentiated, there must be a control population of significant size within the cohort of profiled samples. And although this population need not be defined a priori, it must be shown at some point to have significance to the experiment by identifying additional parameters associated with the population (e.g., gene mutations, tumor markers, clinical response).

This model of information nodes and the states that they occupy provides flexible terms to describe processes wherein cellular proteins adopt conformations, post-translational modifications, or localizations in order to convey specific signals. In this context, a response panel used to profile a diseased cell is being employed in the same way as a series of diagnostic commands a programmer uses to identify bugs in a faulty computer program. In both cases, the inputs are chosen to maximize the information in the output and to reveal where instructions are being incorrectly interpreted.

By identifying disrupted signaling nodes in tumors, accurate diagnostics of therapeutic response and identification of molecular targets for pharmacological intervention can be developed. In many cases the dysregulated signal transduction of a tumor cell would signal for programmed cell death. These negative consequences of proliferative signaling, which are normally carried out by apoptotic tumor suppressor pathways, are frequently lost or inactivated in tumors. In those tumors where apoptotic pathways are inactivated by another signal, such as expression of anti-apoptosis molecules (e.g., Bcl-2, Bcl-XL, Toso), there is an opportunity to target the mechanism of anti-apoptosis and reactivate programmed cell death. Expression of some oncogenes, therefore, can be modeled as an accumulation of proliferative signals that send both pro-life and pro-death instructions simultaneously. Cooperating with these oncogenes are other mutations that disable the pro-death signaling consequences. This model is consistent with results indicating that reversal of oncogene expression leads to rapid death of tumor cells (Chin et al., 1999; Felsher, 2003).

Inherent to the potentiated model and arrayed flow cytometry methods is the control of stimulated node states with the basal or resting state. This built in control enables a level of clarity that is difficult to obtain with other normalization techniques, where sample to sample variations would dominate the profile (e.g., comparing each sample to a normal control). This is especially true for patient samples. It is important to note that there are frequently informative variations among the basal node states; the basal states are historically important to tumor signaling and, in the example of acute myeloid leukemia, most basal states varied widely across samples (with the notable exception of Stat1, see AML profiling). In order to include the basal state of a node, one should place the basal values on the same scale as the responses. This can be achieved by comparing each basal state to a fixed point among the tumor disease samples, such as the minimum or median value observed $$x' = \log_2\left(\frac{x}{x_{min}}\right)$$

[Equation 1-7, scaled basal node state]

Equation 1-7 will provide a spread of basal values on a comparable $\log_2$ scale, but should not be taken to indicate any information regarding change from a normal state.

Hardware/General Techniques

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps that are obvious and known in the art that will increase the sensitivity of the assay are intended to be within the scope of this invention. For example, there may be additionally washing steps, blocking steps, etc.

In a preferred embodiment, the reaction mixture or cells are contained in a well of a 96 well plate or other commercially available multiwell plate. In an alternate preferred embodiment, the reaction mixture or cells are in a FACS machine. Other multiwell plates useful in the present invention include, but are not limited to 384 well plates and 1536 well plates. Still other vessels for containing the reaction mixture or cells and useful in the present invention will be apparent to the skilled artisan.

The addition of the components of the assay for detecting the activation state or activity of an activatible protein, or modulation of such activation state or activity, may be sequential or in a predetermined order or grouping under conditions appropriate for the activity that is assayed for. Such conditions are described here and known in the art. Moreover, further guidance is provided below (see, e.g., in the Examples).

In a preferred embodiment, the methods of the invention include the use of liquid handling components. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of heat exchangers such as controlled blocks or platforms to provide accurate temperature control of incubating samples from 0° C. to 100° C.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In a preferred embodiment, useful detectors include a microscope(s) with multiple channels of fluorescence; plate readers to provide fluorescent, ultraviolet and visible spectrophotometric detection with single and dual wavelength endpoint and kinetics capability, fluoroescence resonance energy transfer (FRET), luminescence, quenching, two-photon excitation, and intensity redistribution; CCD cameras to capture and transform data and images into quantifiable formats; and a computer workstation.

In a preferred embodiment, the detecting is by FACS. In another aspect, the detecting is by high-pressure liquid chromatography (HPLC), for example, reverse phase HPLC, and in a further aspect, the detecting is by mass spectromety.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

The following example serves to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety, including the parent application U.S. Ser. No. 10/193,462, filed July 2002, which claims the benefit of the filing dates of U.S. Ser. No. 60/304,434 and U.S. Ser. No. 60/310,141.

EXAMPLES

Example 1

In this Example, using the methods and compositions of the present invention, the present inventors (also referred to herein as "we") show that Leukocyte Function Antigen-1 (LFA-1) is essential in the formation of immune cell synapses and has a role in the pathophysiology of various autoimmune diseases. In this Example, using the methods and compositions of the present invention, the present inventors demonstrate that ICAM-2 induced an LFA-1 signal transduction pathway that is linked to receptor clustering and activation by both the microtubule and actin cytoskeleton. ICAM-2 exhibited a 21.7 pM/cell binding affinity as determined by single cell analysis. ICAM-2/LFA-1 engagement induced activation of PKC and a reorganization of both the actin and microtubule cytoskeleton. These events resulted in a Syk dependent activation of the p44/42 MAPK pathway upon cytotoxic T cell effector-target cell binding via active LFA-1. ICAM-2 mediated human CD56$^+$CD8$^+$ perforin release and resultant cytotoxicity to target leukemia cells. In comparison to the other ICAMs, ICAM-3 was found to be most similar to ICAM-2's effect and dissimilar to ICAM-1. In IL-2 pre-activated human PBMC, ICAM-2>ICAM-3>>ICAM-1 in mediating perforin release of a CD56$^+$CD8$^{med}$ population. All ICAMs contributed to perforin and granzyme-A loss in CD56$^+$CD8$^{high}$ populations. These results identify a specific functional consequence for ICAM-2/LFA-1 in subset-specific cytotoxic T cell immunity.

Introduction

Leukocyte Function Antigen-1 (LFA-1) is an α,β heterodimer integrin involved in leukocyte adhesion (van Kooyk, Y., and Figdor, C. G. (2000) Curr Opin Cell Biol 12, 542-547). At present, it is well understood that LFA-1 participates in lymphocyte adhesion, with prominent roles in the formation of the immunological synapse (Dustin, M. L., and Shaw, A. S. (1999) Science 283, 649-650), and lymphocyte extravasation and recirculation (Volkov, Y., et al., (2001). Nat Immunol 2, 508-514). LFA-1 adhesion is governed by the intercellular adhesion molecule (ICAMs)-1, -2, and -3 ligands (van Kooyk and Figdor, 2000). Patients afflicted with Leukocyte Adhesion Deficiency disorder (LAD), a syndrome in which the LFA-1 integrin is mutated or missing, suffer sever recurrent bacterial infections and impaired overall immunity (Bunting, M., et al., (2002) Curr Opin Hematol 9, 30-35). Among these clinical manifestations, the LFA-1 knockout mouse has suggested that LFA-1 may have a potential role in mediating tumor regression in adoptive immunotherapy (Mukai, S., et al., (1999) Cell Immunol 192, 122-132; Nishimura, T., et al., (1999) J Exp Med 190, 617-627). Although these studies genetically link a lymphocyte adhesion molecule with impaired immune function, the molecular details that mediate these immunopathologies are less well understood.

Investigations of LFA-1 have primarily focused on the integrin's adhesive role. It is unclear as to how the physical processes of LFA-1 integrin activation and receptor clustering are interconnected and translated into cellular signals upon ligand binding. It is less understood how the absence of these events leads to the devastating effects of LAD and the impaired immune responses in LFA-1 knockout mice. We therefore sought to decipher the molecular details of a model interaction of ICAM-LFA-1 to understand LFA-1 signaling mechanisms initiated upon cell-to-cell contact. Utilizing multiparameter single cell analysis to monitor LFA-1 receptor dynamics upon treatment with a soluble ICAM-2, we found that both the actin and the microtubule cytoskeleton couple ICAM-2 adhesion to LFA-1 activation and clustering. The microtubule cytoskeleton constrained the LFA-1 conformational change (activation), an event that preceded LFA-1 clustering as measured by multiparameter flow cytometry. The induced LFA-1 activation led to the activation of the p44/42 Mitogen Activated Protein Kinase pathway (MAPK; RAF/MEK/ERK), an event that was dependent on both Pyk2 and Syk kinase activities.

The present inventors investigated these molecular details of the ICAM-2 mediated LFA-1 activation in the adhesion between cytotoxic T cells and a target leukemia cell, an event that requires cell-to-cell contact. ICAM-2 stimulation of human CD56$^+$CD8$^+$ T cells could induce perforin/granzyme-A mediated cytotoxicity of leukemia cells. This directed killing was shared by ICAM-3 and to a lesser extent by ICAM-1, two other LFA-1 ligands. These results distinguish a signaling mechanism for ICAM-2/LFA-1 directed cytotoxic T lymphocyte immunity and suggest possible mechanisms by which tumor secretion of ICAM-2 and possibly ICAM-3 might allow for evasion of a directed cytotoxic T cell immune response.

Results

Recombinant ICAM-2 Promotes LFA-1 Mediated Adhesion

The present inventors chose a model Jurkat T cell line as a system to initially dissect the LFA-1 signaling mechanism and then verified the findings in human T cells. A biochemically purified ICAM-2 protein was produced to study ICAM-2/LFA-1 interactions in the absence of other ligands. We purified human ICAM-2 from retrovirally transduced NIH3T3 cells using immunoaffinity chromatography and subsequent gel filtration. We compared it to an ICAM-2-FC fusion protein produced in NSO murine myeloma cells. These murine-based mammalian expression systems were chosen on the basis that they yielded a bioactive form of ICAM-2. Biochemical analysis of ICAM-2FC protein was consistent with the expected molecular weight of the fusion protein (76 kD) and purified human ICAM-2 displayed a molecular weight of 72-74 kD. This size was similar to the 75 kD ICAM-2 purified from Jurkat T cells (data not shown).

The present inventors generated a FITC conjugated ICAM-2 (ICAM-2-FITC) to study LFA-1 receptor dynamics by flow cytometry and laser scanning confocal microscopy (LSCM). We tested for ligand binding of the LFA-1 receptor by monitoring the binding kinetics of ICAM2-FITC on single cells. Low binding was observed in the first 150 seconds, whereupon there was a progressive increase until 750 seconds, and leveled thereafter. In contrast, an anti-LFA-1 antibody displayed an initial spike in the first 50-100 seconds and equilibrated until 800 seconds. Pre-activating LFA-1 by treatment with PMA (McDowall, A., et al., (1998) J Biol Chem 273, 27396-27403) showed an immediate binding of ICAM-2. The gradual ICAM-2 binding after 150 seconds suggested an enhanced LFA-1 binding for its ICAM-2 ligand after some binding-induced event—a property not observed using the anti-LFA-1 or upon PMA activated LFA-1. Binding of ICAM-2-FITC was not observed in trypsinized cells (data not shown) and was blocked by antibodies to LFA-1 (described below). Therefore, there appeared to be an increase in binding of the ICAM-2 ligand as a function of time, suggesting the presence of an induced binding site on the target cells.

Analysis of the ICAM-2 binding population by flow cytometry showed a dependency on both the actin cytoskeleton and temperature. ICAM-2 adhesion was enhanced at 37° C. vs. 4° C. Pre-treatment with the actin depolymerizing agent cytochalisin D revealed two ICAM-2 binding populations at both 37° C. and 4° C., contrasting with the binding phenomena observed for anti-LFA-1. Saturation of ICAM-2-FITC was observed at 37° C. more readily than at 4° C. (data not shown). Single cell binding affinity measurements for ICAM-2 were obtained by computing the percent ICAM-2-FITC bound per cell. Curve fit analysis indicated a dissociation constant of $0.21 \pm 0.07$ M/$10^4$ cells. This value equates to 21.7 pM/cell, representing the first ligand binding measurements reported for ICAM-2 within the physiological context of cell surface LFA-1. Thus, quantitative single cell analysis of ICAM-2 ligand binding suggests strong binding at physiological temperatures.

Soluble ICAM-2 Induces LFA-1 Clustering and Cytoskeleton Polarization

The present inventors investigated if LFA engagement altered cytoskeletal structures and observed a reorganization of both the actin and microtubule cytoskeleton upon ICAM-2 stimulus. The present inventors monitored the cytoskeletal architecture by flow cytometry and observed a simultaneous change in the actin and microtubule organization upon ICAM-2 binding, an effect consistent with depolymerization. ICAM-2 treatment induced a rapid clustering of LFA-1 within one minute, with multiple clustering events at five minutes. Using the ICAM-2-FITC ligand to visualize the cell surface, indicated that the ICAM-2 ligand induced clustering of the LFA-1 receptor. The clustering event showed some colocalization using a non-blocking 2 integrin antibody (clone CTB104). Thus, we speculated that ICAM-2 binding to LFA-1 induced a signal that resulted in a reorganization of the LFA-1/ICAM-2 complex. We therefore decided to investigate this in relation to the observed changes in the actin/microtubule cytoskeleton.

The present inventors assessed LFA-1 receptor dynamics by multiparameter flow cytometry upon ICAM-2 binding to correlate LFA-1 activation and clustering. We utilized the doublet discriminator module on a FACSCalibur machine to distinguish between distributed and focalized fluorescence pulses (FFP) upon laser excitation of single cells. Incubation of ICAM-2 at 37° C. vs. 4° C. displayed a decrease in the FFP, an effect that was greatly enhanced upon cytochalisin D treatment. ICAM-2-FITC surface binding was monitored by the fluorescence intensity and normalized against the time-of-flight (TOF) of the fluorescence pulse (FP). We interpreted the value of ICAM-2-FITC intensity per TOF as a quantitative assessment for LFA-1 clustering, as the TOF is proportional to the laser-excited cellular area. Computing this value as a function of time for an ICAM-2 stimulus is proportional to the increased clustering events observed by LSCM.

ICAM-2 Adhesion Induces a Conformational Change in LFA-1 that is Regulated by the Microtubule Cytoskeleton.

Although the enhanced ICAM-2 adhesion and induced LFA-1 clustering is reflective of overall increased avidity for the ICAM-2 ligand, it does not necessarily reflect an LFA-1 activation state (high affinity state) (McDowall et al., 1998). Upon LFA-1 activation, a conformational change exposes an epitope that is recognized by the mAb24 antibody (Neeson, P. J., et al., (2000) J Leukoc Biol 67, 847-855). A mAb24-Alexa633 conjugate was used to assess the activation state of LFA-1 upon ICAM-2 stimulus by flow cytometry. Unstimulated cells did not display mAb24 binding, contrasting the induction observed with PMA treatment. ICAM-2 stimulated cells displayed a bimodal population in active LFA-1, an effect that was attenuated by cytochalisin D. Treatment with microtubule disrupting agents, nocodazole and taxol, resulted in full activation of LFA-1 upon ICAM-2 stimulus. In contrast, disrupting the actin cytoskeleton via cytochalisin D diminished the ICAM-2 induced LFA-1 activation, although it enhanced LFA-1 receptor clustering and subsequent ICAM-2 binding. Therefore, the actin and microtubule cytoskeletal network differentially impact LFA-1 activity and avidity.

The present inventors monitored LFA-1 activation and clustering simultaneously as a function of ICAM-2 stimulus per time by flow cytometry. Correlating the mean fluorescence of mAb24 antibody with the LFA-1 clustering value revealed LFA-1 activation preceeded LFA-1 clustering within 30 seconds there was a significant increase in binding of the mAb24 antibody but only a modest increase in clustering. However, after another 30 seconds up to 30 minutes the relative binding of mAb24 increased somewhat but there was a significant increase in the clustering value. Thus, these results suggest that the ICAM-2 ligand induced activation of LFA-1 is followed by subsequent LFA-1 clustering.

The present inventors observed that treating cells with a PKC inhibitor, bisindolymaleimide I (BIM I), inhibited ICAM-2 induced LFA-1 activation as measured by using mAb24 binding. ICAM-2 adhesion, as measured by the binding of ICAM-2-FITC, was not affected. This suggested that the ligand induced receptor conformational change was dependent on intracellular kinases. Interestingly, ICAM-2 induced a calcium influx, a component necessary in PKC activation (data not shown). Thus, these observations suggest that the ICAM-2 ligand induced exposure of the mAb24 neoepitope triggers a PKC dependent intracellular signaling event. We decided to investigate the downstream signaling consequences of ICAM-2 binding to LFA-1.

ICAM-2 Induces p44/42 MAPK Activity Through LFA-1

Flow cytometric based kinase profiling experiments were performed to identify a signaling pathway downstream of PKC activation upon ICAM-2 stimulus. Treatment with ICAM-2 induced both p44/42 MAPK phosphorylation and activation. An ICAM-2 titration correlated with phosphorylation of p44/42 MAPK as determined by single cell flow cytometric analysis, results congruent with kinase activity analysis. Titration of mAbs to specific integrins competed with ICAM-2 binding, and thus diminished the induced p44/42 MAPK phosphorylation. This inhibition was not observed after pretreatment with mAbs to various integrins indicating that the ICAM-2/LFA-1 interaction was mediating the p44/42 MAPK activation.

Activation of PKC, PYK2, and SYK are Necessary for the ICAM-2/LFA-1 Induction of p44/42 MAPK Activity The present inventors undertook flow cytometric based p44/42 MAPK kinase inhibition and activation profiling to identify necessary components for LFA-1 signaling. PKC inhibitor BIM I, cytoskeletal disrupting agents cytochalisin D, taxol, nocodozole, and sequestering of divalent cations by EDTA diminished the ICAM-2 induced p44/42 MAPK signal, suggesting that the ligand-induced events of LFA-1 are mechanically linked to signal transduction by the actin-microtubule cytoskeleton. To identify upstream kinases that were responsible for signal transmission from LFA-1 to p44/42 MAPK, a series of kinase inhibitors were applied and tested for their ability to abrogate the ICAM-2 induced p44/42 MAPK activity, whereas Herbimycin A and Emodin, inhibitors of src and p56lck had no effect. Tyrphostin A9 and piceatannol, specific inhibitors of proline-tyrosine kinase 2 (Pyk2) and Spleen-tyrosine kinase (Syk), respectively (Avdi, et al., (2001) J Biol Chem 276, 2189-2199; Fuortes, et al., (1999) J Clin Invest 104, 327-335) abrogated the ICAM-2 induced activation of p44/42 MAPK and its upstream activator Raf-1.

The present inventors tested whether Pyk2 and Syk interacted with a particular integrin. Pyk2 and Syk were phosphorylated and co-immunoprecipitated with the integrin upon ICAM-2 treatment, indicating Pyk2 and Syk translocated to the membrane. This was coincident with phosphorylation of Pyk2 and Syk upon ICAM-2 stimulus as a function of time. Phosphorylation of $PKC_{II}$, and Pyk2 were detected at one minute, followed by Syk phosphorylation at 5 minutes. We confirmed that Pyk2 and Syk activities were dependent on PKC activation. Taken together with the above results, this suggested that the LFA-1 signaling mechanism imparted by ICAM-2 is at least initiated by PKC and relayed to the p44/42 MAPK pathway by Pyk2 and Syk.

LFA-1 is Involved in Effector-Target Cell Adhesion and Facilitates Human Cytotoxic T Cell Activation Since LFA-1 is involved in adhesion between lymphocytes, a process that occurs at several immunological synapses, we were interested in investigating the molecular events identified for the ICAM-2/LFA-1 interaction in a physiological context. It has been suggested that a clustered topographic presentation of ICAM-2, independent of expression levels, is an effective target structure by which natural killer cells initiated cytotoxicity (Helander, T. S., et al., (1996) Nature 382, 265-268). We first applied a FACS based effector-target killing assay to quantitatively monitor target cell lysis of HL60 leukemic cells upon treatment with stimulated human PBMC at various effector: target cell ratios. Flow cytometric detection of target cell lysis has been reported to be more sensitive than the standard chromium release assays (Lecoeur, H., et al., (2001) J Immunol Methods 253, 177-187). We labeled HL60 cells with the fluorescent dye CFSE and monitored the cell quantity by flow cytometry in standard effector-target cell based assays. Soluble ICAM-2 could initiate target cell lysis in the presence of IL-2 but not in the absence of IL-2. In IL-2 pre-activated cells, ICAM-1 and ICAM-3 did not initiate as potent a cytotoxic cell response in contrast to ICAM-2.

Since natural killer cells (NK) comprise a heterogeneous population, namely specific cytotoxic T lymphocytes (CTL, with $C8^+$ subsets therein), NK cells ($CD16^+$ and subsets therein), and $CD4^+$ TH1 cells (Biron, C. A., and Brossay, L. (2001) Curr Opin Immunol 13, 458-464.), we determined if ICAM-2 was unique to a particular human NK cell subset. We utilized the multidimensional gating capability of flow cytometry to identify distinct cellular populations that were contributing to the cytolytic activity observed in human PBMC. We also monitored intracellular levels of perforin and granzyme-A by flow cytometry, two proteins that mediate target cell lysis by NK cells in these populations. We identified 6 distinct populations by CD8 and CD56 surface stains in human PBMC and gated on these subsets for all subsequent intracellular functional assays. We performed effector-target cytotoxicity assays in the presence of ICAM-1, ICAM-2, and ICAM-3 soluble ligand and HL60 target cells. We did not observe significant changes in population subset frequencies post stimulation. The $CD56^+CD8^{low}$ population displayed no significant changes in intracellular perforin or granzyme-A upon stimulation with ICAM-1, -2, or -3. The $CD56^+CD8^{med}$ population displayed a slight increase (1.5-2 fold) in the frequency of the perforin negative population for ICAM-2 and ICAM-3 (21.5% ICAM-2>19.8% ICAM-3>13.7% ICAM-1). The $CD56^+CD8^{high}$ population displayed a loss in both granzyme-A and perforin for ICAM-1, -2, -3 stimulations compared to unstimulated with a significant loss in the granzyme-A negative population for ICAM-2 (58.3%) compared to ICAM-1 (4.12%) or ICAM-3 (3.07%). The $CD56^-CD8^{high}$ also displayed a loss of both granzyme-A and perforin by all ICAM stimulations. Since it was not possible to positively identify the subsets within the $CD56^-CD8^-$ population, they were omitted from analysis.

Quantifying the intracellular amounts of perforin and granzyme-A in the CD56CD8 subsets relative to unstimulated cells also identified similarities and differences for the ICAMs as evidenced below. ICAM-2 and ICAM-3 mediated loss of granzyme-A and perforin to a greater extent than ICAM-1. Additionally, in IL-2 pre-activated cells, differences where seen with the ICAM stimulations: ICAM-2>ICAM-3>>ICAM-1 displayed a loss of perforin, particularly in the $CD56^+CD8^{med/high}$ populations. ICAM-2 and ICAM-3 also induced perforin loss in the $CD56^+CD8^{low}$, however ICAM-2 required preactivation by IL-2. There were lower levels of granzyme-A detected for the $CD8^{high}$ subsets ($CD56^+$ or $CD56^-$) for ICAM-2>ICAM-3>ICAM-1> unstimulated. In the presence of IL-2 pre-activation, all the ICAMs induced release of granzyme-A in the $CD56^+CD8^{high/med}$ populations, with a particular decrease by ICAM-2. No significant changes were seen in the $CD56^+CD8^{low}$ population for granzyme-A. These differences were similar at various effector-target cell ratios (50:1, 25:1, 12.5:1) (data not shown). Thus, similarities and difference exist for ICAM-1, -2, and -3 stimulation of cytolytic activity in CD56CD8 subsets. All three ICAMs mediated perforin release in the $CD56^-CD8^{high}$ populations. ICAM-2 and ICAM-3 were most similar in mediating perforin/granzyme-A release in the $CD56^+CD8^{high}$ and $CD56^+CD8^{med}$ populations.

We focused on the $CD56^+CD8^+$ cells (both the $CD8^{med}$ and $CD8^{high}$ subsets) and tested if inhibition of Syk, p44/42 MAPK or disruption of the cytoskeleton detrimentally affected effector-target (E:T) cell conjugation as measured by a flow cytometric conjugate formation assay (Morgan, M. M., et al., (2001) J Immunol 167, 5708-5718). Disruption of cytoskeletal actin and microtubules enhanced E:T conjugate formation congruent with prior results that disruption by these agents enhanced LFA-1 activation. Inhibition of Syk by piceatannol inhibited conjugate formation whereas inhibiting p44/42 MAPK by PD98059 did not. These results suggest that Syk activity is necessary for LFA-1 adhesion of effector-target cells and is consistent with a report indicating that Syk/ZAP-70 are necessary for LFA-1 to LFA-1 activation on the same cell (Soede, R. D., et al., (1999) J Immunol 163, 4253-4261).

p44/42 MAPK appeared to not be necessary for E:T conjugate formation. Monitoring active LFA-1 and intracellular activation of p44/42 depicted a time dependent correlation between these two markers in CD56$^+$CD8$^+$ cells as stimulated by ICAM-2.

Discussion

In this report it was observed that (1) ICAM-2 can induce LFA-1 clustering, activation, and cytoskeletal reorganization in the absence of exogenous activators such as cytokines or TCR signaling; (2) LFA-1 transmits a signal to the p44/42 MAPK pathway involving PKC, Pyk2, and Syk upon ligand binding; and (3) LFA-1 receptor dynamics are mechanically coupled to signal transduction by both the actin and microtubule cytoskeleton network. The physiological outcome of these molecular events triggered perforin and granzyme A mediated CD56$^+$CD8$^+$ T cell cytotoxicity that were mostly shared by ICAM-2 and ICAM-3 but not ICAM-1.

2 integrin signaling mechanisms vary depending on the system of study and are centered on adhesive roles in cell morphology and motility (Dib, K. (2000) Front Biosci 5, D438-451). 2 integrin signaling has been shown to involve cytoskeletal reorganization via tyrosine phosphorylation of paxillin, vav, and GTPase activating proteins among others (Fuortes, M., et al., (1994) J Cell Biol 127, 1477-1483; Zheng, L., et al., (1996) Proc Natl Acad Sci USA 93, 8431-8436). Studies focused on LFA-1 mediated leukocyte adhesion (CD11a/CD18) have shown a regulatory role for PKC in LFA-1 avidity (Bleijs, D. A., et al., (2001) J Biol Chem 276, 10338-10346; Hedman, H., and Lundgren, E. (1992) J Immunol 149, 2295-2299) and have demonstrated that TCR signaling can activate LFA-1 (Peterson, E. J., et al., (2001) Science 293, 2263-2265). It has also been shown that chemokines, in the absence of TCR signaling, can serve as activators of LFA-1 during lymphocyte/endothelial contact (Constantin, G., et al., (2000) Immunity 13, 759-769). It has not been clear how LFA-1 integrin adhesion, clustering, and activation are coupled to intracellular signaling events, in the absence of external (chemokine) or internal (TCR or costimulatory molecule) stimulation.

A synthesized peptide of ICAM-2's first Ig domain (PI, amino acids 21-42) can induce LFA-1 mediated adhesion at high concentrations (62 M), which was comparable to a 48-fold lower ICAM-2 soluble protein concentration (1.3 M) in a bulk cellular adhesion assay (Kotovuori, A., et al., (1999) J Immunol 162, 6613-6620). However, P1 binding did not induce the active conformation of LFA-1 and did not induce calcium influx (Kotovuori et al. 1999), whereas full length ICAM-2 binding resulted in active LFA-1 (see FIG. 6D from U.S. Ser. No. 10/193,462) and a calcium influx event (data not shown). The calculated ICAM-2 affinity of 217±66 nM (per 10$^4$ cells) contrasts the 605±55 nM $k_D$ reported using BIAcore analysis of an engineered "active" locked I domain of LFA-1 (Shimaoka, M., et al. (2001) Proc Natl Acad Sci USA 98, 6009-6014). The reported affinities for ICAM-2 binding here take advantage of single cell resolution within a physiological context, something not possible utilizing purified or genetically engineered LFA-1. The differences observed for peptide vs. protein concentrations are likely attributed to impurities in the peptide synthesis and/or presence of carbohydrate moieties native to the endogenous ICAM-2, which comprise greater than 30 kD of its approximate 66 kD molecular weight and have been suggested to orient ICAM-2 binding to LFA-1 (Casasnovas, J. M., et al. (1997) Nature 387, 312-315; de Fougerolles, A. R., et al. (1991) J Exp Med 174, 253-267).

We investigated the role of the actin and microtubule cytoskeleton in LFA-1 receptor activation and clustering as induced by the ICAM-2 ligand by multiparameter flow cytometry. Disruption of the actin cytoskeleton enhanced LFA-1 clustering and ICAM-2 binding, corroborating previous studies that suggested the actin cytoskeleton constrains LFA-1 mobility (Lub, M., et al., (1997) Mol Biol Cell 8, 341-351). Interestingly, actin depolymerization abrogated the ICAM-2 induced LFA-1 activation. In contrast, disruption of the microtubules by both nocodazole and taxol enhanced LFA-1 activation as determined by exposure of the neo-epitope recognized by the mAb24. Recently, it has been reported that depolymerization of microtubules increases the lateral mobility of 2 integrins in macrophage cell lines (Zhou, X., et al., (2001) J Biol Chem 276, 44762-44769); therefore its conceivable that the microtubules regulate the conformational change upon ligand binding necessary for exposure of the LFA-1 activation epitope. These observations suggest the actin-microtubule cytoskeleton regulates both the high-avidity and high affinity state of LFA-1 upon ligand binding. We observed that LFA-1 signal transduction was abrogated in the presence of all cytoskeletal disrupting agents tested (cytochalisin D, nocodazole, and taxol) indicating that the LFA-1 receptor is linked to signal transduction machinery by the cytoskeleton. Thus, the mechanistic uncoupling of the high avidity and high affinity states of LFA-1 suggests that intracellular events that regulate/mediate these two states exist at the LFA-1 integrin-cytoskeletal juncture and relay the LFA-1 receptor dynamics to intracellular signaling proteins upon ligand binding.

Several chemical inhibition screens were designed to identify the proteins involved in the LFA-1 to p44/42 MAPK signaling event. Both Pyk2 and Syk were identified to be necessary for activation of the p44/42 MAPK pathway and were dependent on PKC activity upon ICAM-2 binding. Phosphorylation of Pyk2 has been associated with homotypic adhesion mediated by an LFA-1/ICAM-1 interaction in B cells (McDonald, J. T., et al., (2000) Immunol Invest 29, 71-80). In addition, Pyk2 activation has been shown to be necessary for p44/42 MAPK activity in other model systems (Barsacchi, R., et al., J. (1999) FEBS Lett 461, 273-276; Lev, S., et al., (1995) Nature 376, 737-745). Syk is a tyrosine kinase essential in III 3 signaling (SacI, A., et al., (2000) Biochem J 351 Pt 3, 669-676), and links Fc RI signaling to the ras/MAPK pathway (Jabril-Cuenod, et al., (1996) J Biol Chem 271, 16268-16272). Inhibition or ablation of Syk, either by pharmacological means (via inhibition by piceatannol), biochemical means (dominant negative Syk), or genetic means (Syk$^{-/-}$ mice) inhibits natural cytotoxicity (Brumbaugh, K. M., et al., (1997) J Exp Med 186, 1965-1974; Colucci, F., et al., (1999) J Immunol 163, 1769-1774). Thus LFA-1 activation signaling to Syk, a kinase that has been shown to be important for NK cell function, provides a biochemical link between surface integrin activation and effector cell function.

The present inventors demonstrated that both Pyk2 and Syk are necessary in ICAM-2 induced LFA-1 signaling to Raf-1, the upstream kinase in the p44/42 MAPK (RAF/MEK/ERK) cascade. Inhibition of p44/42 MAPK did not prevent the occurrence of CD56$^+$CD8$^+$ cell conjugation. By immunofluorescence analysis, it has been shown that treatment of the NK leukemic cell line YT with the p44/42 MAPK inhibitor PD98059 inhibits perforin redistribution to the site of effector-target cell contact (Wei, S., et al., (1998) J Exp Med 187, 1753-1765). In addition, the p44/42 MAPK pathway has been shown to be important in the regulation of cytoxicity in natural killer cells (Jiang, K., et al., (2000) Nat Immunol 1, 419-425). Thus, the p44/42 MAPK pathway, here demonstrated to become active upon LFA-1/ICAM-2 binding, has been shown to be connected to at least perforin granule exocytosis. Thus, the LFA-1 signaling pathway as elicited by ICAM-2 contains signaling junctures that map to both the effector-target cell adhesion event and activation of cytolytic machinery in the human CD56$^+$CD8$^+$ cytotoxic T cell population. These results provide direct evidence for a functional consequence of LFA-1 integrin adhesion with cytolytic signaling mechanisms.

We also observed that ICAM-2 was similar to ICAM-3 in mediating cytolytic activity as evidenced by release of perforin and granzyme-A in effector-cell conjugation, effects of which contrasted ICAM-1 (see FIG. 8 from U.S. Ser. No. 10/193,462). We have previously observed similarities between ICAM-2 and ICAM-3 intracellular signaling mechanism that also differed from that of ICAM-1 (Perez, O. D., et al., (2002) Immunity 16, 51-65). However, the results do not exclude the possibility of ICAM-2 stimulating other yet to be identified cytotoxic capable subsets, as high cytolytic activity was observed in bulk PBMC (see FIG. 9 from U.S. Ser. No. 10/193,462).

Prior investigations into cytotoxic T cells have established that blocking the LFA-1/ICAM interactions inhibits effector-target cell adhesion and therefore concluded that it also blocks cytolytic activity in NK cells (Donskov, F., et al., (1996) Nat Immun 15, 134-146; Krensky, A. M., et al., (1984) J Immunol 132, 2180-2182; Matsumoto, G., et al., (2000) Eur J Immunol 30, 3723-3731). Functional studies of NK cells from LFA-1$^{-/-}$ mice have demonstrated that LFA-1 adhesion is necessary for IL-2 activated NK killing (Matsumoto et al., 2000) and also that LFA-1$^{-/-}$ CD8$^+$ T cells are defective for T cell activation and effector function (Shier, P., et al., (1999) J Immunol 163, 4826-4832). Interestingly, NK cell cytotoxicity is defective in NK cells from LAD patients (Shibuya, K., et al., (1999) Immunity 11, 615-623). It has only recently been shown that the directed killing of cytotoxic T lymphocytes involves polarization of the microtubule-organizing center (MTOC) towards LFA-1 at the CTL-target site (Kuhn, J. R., and Poenie, M. (2002) Immunity 16, 111-121), an indication that LFA-1 may possess a functional role other than strictly adhesion.

In conclusion we find that ICAM-2, as an LFA-1 ligand, can mediate activation and clustering of the LFA-1 receptor—an event that in turn polarizes the microtubule and actin cytoskeleton and activates the p44/42 MAPK pathway. These events were found to be necessary for effector-target cell binding of CD56$^+$CD8$^+$ T cells, and perforin/granzyme A mediated cytolytic activity. This effect was shared by ICAM-3. The mechanisms governing LFA-1 receptor dynamics and intracellular signaling reported here suggest LFA-1 signaling functionally contributes in CD56$^+$CD8$^+$ cytolytic activity in addition to possessing an adhesive role upon which other molecular interactions occur. Improper localization of the MTOC has been shown to inhibit exocytosis of lytic granules in CD8$^+$ tumor infiltrating T cells, thereby ablating perforin mediated cytolytic activity necessary for a CTL response in murine tumor models (Radoja, S., et al., (2001) J Immunol 167, 5042-5051). Ironically, defective CD8$^+$ tumor infiltrating T cells can effectively mediate cell killing in vitro (Radoja, S., et al., (2001) J Immunol 166, 6074-6083), suggesting tumor mediated inhibitory mechanisms exist within the tumor microenvironment. The production of soluble ICAMs (1 and 3) has been observed in sera from cancer and autoimmunity patients, though analysis has not been extended to ICAM-2 (Bloom, et al., (2002) J Rheumatol 29, 832-836). Only one report has indicated that elevated levels of soluble ICAM-2 were present in leukemia patients and decreased upon chemotherapy (Mustjoki, S., et al., (2001) Br J Haematol 113, 989-1000). The etiology of these observations is unknown. In the context of the work presented here, it is plausible to speculate that either dysregulation of surface ICAM-2 or secretion of soluble ICAM-2 can prematurely trigger or block CD56$^+$CD8$^+$ cytolytic activity at the effector-target site and permit tumor escape from T cell lysis. Other, specific roles, of ICAM-2 in its interaction with other integrin ligands could lead to a better understanding of events that promulgate from the effector:target cell interface Materials and Methods Immunological and Chemical Reagents mAbs to 1, 2, 3, 4, 5, 6, 1, 4, 5, $_L$, LFA-1, Pyk2, SyK, Mac-1, ICAM-1, and ICAM-3 (PharMingen). CD3, CD4, CD8, CD19, CD56, CD45 direct conjugates (FITC/PE/PERCP/APC/Biotin), granzyme-A-FITC (PharMingen). Perforin-CY5 and CD8-CY5PE (gift from the Herzenberg Laboratory, Stanford University). ICAM-2 mAb and ICAM-2-FITC (IC2/2 Research Diagnostics). Anti-phospho PYK2(Y402), anti-phospho-p44/42 (pT185Py187) (Biosource). Anti-phospho PKC/(Thr638), anti-phospho-Syk(Tyr525/526), anti-phosphoRaf1(Ser259) (Cell Signaling Technologies). Protein and chemical reagents used: fluorescein isothiocyanate (FITC) (Pierce), Alexa fluor dye series 488, 546, 568, 633, taxol-alexa546, phalloidin-alexa633, and CFSE (Molecular Probes). Tyrphostin A9 and 18, SB203580, piceatannol, bisindolylmaleimide I and II, herbimycin A (Calbiochem). Emodin, genistein, DMSO, PMA, PHA, staurosporine, ionomycin, propidium iodide, cytochalisin D (Sigma). Protein A/G agarose (SCBT). Recombinant human IL-2 (Roche), recombinant human ICAM-1-FC, ICAM2-FC, ICAM3-FC (Genzyme). Secondary antibodies to mouse and rabbit IgG (Santa Cruz). Mock treatments consisted of mouse IgG (for antibodies), 1% BSA (for proteins), or 0.001% DMSO vehicle (for chemicals).

Cell Culture

NIH3T3 cells were maintained in DMEM, 10% DCS, 1% PSQ (Duelbecco Modified Eagle Media, 10% Donor calf serum, 1% penicillin-streptomycin (1000 units/ml and 2 mM L-glutamine PSQ). Jurkat T-cells were maintained in RPMI-1640, 10% FCS, 1% PSQ at 1×10$^5$ cells/ml and serum starved 12 hours for all functional assays. Cells were maintained at 5% CO$_2$/37° C. humidified incubator. Human peripheral blood monocytes were obtained by Ficoll-plaque density centrifugation (Amersham Pharmacia, Uppsala, Sweden) of whole blood from healthy donors (Stanford Blood Bank) and depleted for adherent cells. Magnetically activated cell sorting was used to negatively isolate naïve CD8$^+$ T cells for studies as indicated (Dynal, Oslo, Norway).

Soluble ICAM-2 Generation and Synthesis of ICAM-2-FITC and ICAM2-Beads

Full length ICAM2 cDNA was obtained from Jurkat cells and cloned into retroviral vector PBM-Z-IN at the BamHI/Sal1 site as described (Perez et al., 2002). Human ICAM-2 was overexpressed in NIH3T3 cells by retroviral infection and harvested by immunoaffinity chromatography. ICAM-2 was affinity purified using a two step lysing procedure and subsequent purification on an anti-ICAM-2 solid support. Cells were lysed in buffer A (20 mM Tris pH 7.5, 150 mM NaCl 1 mM EDTA 1 mM EGTA, 0.1% NP40, 2.5 mM Na$_2$PO$_4$, 1 mM-glycerolphosphate, 1 mM Na$_3$V0$_4$, 1 ug/ml Leupeptin, 1 mM PMSF, protease inhibitor cocktail tablet (Boehringer Mannheim) for 5 min 4° C., and subsequently permeabilized with 50% v/v with buffer B (Buffer A plus 1% Triton-X-100) for 30 min 4° C. Supernatant was harvested by centrifugation (14,000 RPM, 5 min, 4° C.). An Anti-ICAM-2 pAb to the C-terminal (4 mgs, Santa Cruz) was conjugated to an Affi-Gel Hz activated support (Biorad) as suggested by manufacturer. This support couples Ig molecules via the FC region, resulting in higher antigen binding capacity. Batch lysate of harvested supernatant was performed (4° C., for 2 hrs), and washed 4 times in buffer C (0.1% Tween-20, PBS pH 7.4). ICAM-2 protein was eluted by 4.5 M NaCl (in Tris pH 6.8), dialyzed overnight (in PBS pH 7.4, 0.001% azide, 0.01% glycerol, 4° C.), concentrated using size exclusion spin chromatography and stabilized using 0.01% glycerol. Anti-ICAM-2 solid support was re-equilibrated in buffer C, stored in 0.001% thimerosol and re-used up to 3 times. Purity was >98% as assessed by coomasie gel. Size exclusion chromatography removed higher molecular weight aggregates and were not observed on purified ICAM-2 by native gel electrophoresis. 20 mgs were purified by this method and used for this study. ICAM-2-FITC synthesis was achieved by chemical conjugation to NHS-Fluorescein (Pierce) and unreactive dye was removed by gel filtration. ICAM-2-FITC probe did not integrate into trypsinized Jurkat cells or bind when blocked by LFA-1 antibody clones TS1/22 or TS1/18 (Developmental Hybridoma Studies Bank) or unlabeled ICAM-2 protein as determined by flow cytometry. ICAM-2-FITC binding was not blocked by 2 integrin clone CT104 (Santa Cruz). Purified ICAM-2 was comparable to human recombinant ICAM-2FC fusion protein purified from NSO murine myeloma cells (Genzyme). ICAM-1 FC and ICAM-3FC were also purified from NSO cells (Genzyme). Proteins were spun at 14,000 RPM, 5 min prior to use. 1 mg of ICAM-2 protein was conjugated to $2 \times 10^8$ epoxy activated beads as suggested by manufacturer (Dynal). $4 \times 10^5$ beads containing a total of 2 g ICAM-2 protein were used as indicated. Gel imaging was performed on a VersaDoc machine (Biorad) and analyzed using Quantity One quantitation software (Biorad).

Flow Cytometry

Intracellular and extracellular staining was performed as described (Perez and Nolan, 2002). Intracellular probes for active kinases were made by conjugating phospho-specific antibodies to the Alexa Fluor dye series as described and used in phospho-protein optimized conditions (Perez and Nolan, 2002). Kinetic analyses was performed by direct application of fixation buffer in time synchronized 96-wells maintained at 37° C. Intracellular actin and microtubule staining was performed using phalloidin-Alexa633 and taxol-Alexa546 dyes (Molecular Probes). Adhesion and clustering assays were performed using ICAM-2-FITC as described in text. LFA-1 activation was assessed by either mAb24-Alexa633 or mAb24-Alexa546 conjugate, surface stained at 37° C. Flow cytometry data are representative of 3 independent experiments of $10^6$ cells/sample. 10-50,000 events were collected and manually calibrated on a FACSCalibur machine. Data plotted in bar graph format is expressed as geometric mean fluorescence intensity (MFI) and normalized for isotype controls. Log ratios are defined as the MFI of stimulus to the MFI of unstimulated cells. Data was analyzed using Flowjo software (Treestar).

Single Cell ICAM-2 Binding Measurements

Percentage of ICAM-2-FITC binding was expressed as $100*((MFI_{exp}-MFI_{ctl})/(MFI_{final}-MFI_{ctl}))$, where $MFI_{exp}$ equals the mean fluorescent intensity of experimental concentration, $MFI_{ctl}$ equals mean fluorescent intensity of unstained cells, $MFI_{final}$ equals mean fluorescent intensity of final concentration that saturated binding. The samples were incubated with final concentrations as indicted in FIG. 3 from U.S. Ser. No. 10/193,462 for 30 min at 37° C. in 50 μL staining media (def RPMI, 4% FCS), washed 1× (500 μL, PBS pH 7.4, containing 1 mM EDTA), and resuspended in 100 μL (1% paraformaldehyde). Dilution factor of staining conditions and molecular weight of 72.1 kD was used in determining molar concentrations. The staining buffer contained 2.4 mM calcium and 2 mM magnesium. The data were fit to the equation $V=V_{max}[S]/(K_m+[S])$ where V is the percent bound, [S] is the ICAM-2-FITC concentration, and K, is the Michaelis-Menten binding constant using Kaleidagraph software.

Laser Scanning Confocal Microscopy

Jurkat cells were treated as indicated and adhered to poly-L-lysine (Sigma) coated sterilized coverslips (1 mg/ml, 30 min) by mild centrifugation (1000 RPM, 10 min), washed twice in phosphate buffered saline pH 7.4 (PBS) and fixed in 2.7% paraformaldehyde (in PBS). Cells were permeabilized (5 min, 0.1% Triton-X-100 in PBS), washed twice in PBS, blocked in 4% FCS, and subjected to antibody or intracellular staining as indicated. Stained coverslips were mounted and visualized using a Zeiss laser scanning confocal microscope 510.

Immunoprecipitations, Immunoblotting and Kinase Assays

Cell extracts were prepared by washing $2 \times 10^6$ cells (treated as indicated) in ice cold PBS and harvesting in lysis buffer (20 mM Tris pH 7.5, 150 mM NaCl 1 mM EDTA 1 mM EGTA, 1% Triton X-100, 2.5 mM $Na_2PO_4$, 1 mM-glycerolphosphate, 1 mM $Na_3VO_4$, 1 g/ml Leupeptin, 1 mM PMSF, protease inhibitor cocktail tablet (Boehringer Mannheim). Extracts were centrifuged 14,000 RPM (5 min, 4° C.) and 10-20 g (BCA protein assay (Pierce)) were immunoblotted using standard procedures. Immunoprecipitations (IP) were pre-cleared with protein A/G plus-agarose beads, incubated with primary ab (1 h), protein A/G plus-agarose beads (1 h) and washed 4× with lysis buffer. Blots were incubated with the indicated antibodies and developed using ECL (Amersham). Immunoblots stripped and reprobed (as indicated) were done by incubating with stripping buffer (62.5 mM Tris, pH 6.8, 10% SDS, 1%-mercaptoethanol) (30 min, 55° C.). MAPK activity was detected by a p44/42 MAPK kinase kit as suggested by manufacturer (Cell Signaling Technologies).

Cytolytic Activity, Perforin Release Assays, and Conjugate Formation Assays

Target cell lysis was measured by flow cytometric based detection of CFSE labeled HL60 cells. HL60 cells were labeled with 1 g of CFSE (30 min, 37° C.). Targets were washed twice and mock treated, IL-2 activated (100 U/ml), CD3/CD28 activated (1 g/ml), or treated with ICAM2 beads or soluble ICAM-1, -2, or 3 (10 g/ml, 30 min, 37° C.) before plating at $10^4$ target cells/well of a 96-well round bottom plate. CTLs were added at 50:1, 25:1, and 12.5:1 E:T ratio, and incubated at 37° C. for 4 hrs. Cells were then processed for multiparameter flow cytometry and intracellular perforin stain. Percent specific lysis was calculated by the following equation: % specific lysis=100−100×(experimental HL60 count/total control HL60 count). HL60 counts were detectable by the CFSE fluorescence. Percent perforin was calculated by the following equation: % perforin=100×[(experimental perforin MFI−isotype mAb MFI)/(total perforin MFI−isotype mAb MFI)]. MFI refers to mean fluorescent intensity of flow cytometric based intracellular detection. Cell conjugates were determined by flow cytometry as described (Morgan et al., 2001). Chemical inhibition was done at 10 M of indicated compound (30 min, 37° C.) prior to stimulation as indicated. All experiments were performed in triplicate.

Example 2

Phospho-protein driven signaling networks support altered growth factor responses of tumors and are considered crucial to initiation and maintenance of tumor cell pathology. In acute myeloid leukemia (AML), dysregulated growth and inhibition of apoptosis lead to the accumulation of immature myeloid progenitor cells and oncogenic progression. We show here that surveying phospho-protein responses to cytokine stimulation, in addition to widely studied basal phosphorylation states, reveals dysregulated signaling nodes and enables identification of a signaling pathology profile. We further show that unsupervised clustering of phospho-protein profiles can be used to identify AML patient groups that correlate with prognostic indicators, such as mutation of the receptor tyrosine kinase Flt3 and chemotherapy resistance. In patients with Flt3 mutations, the biochemical differences used to define patient groups indicated a potentiated response of Stat3 and Stat5 to the myeloid cytokines GM-CSF and G-CSF.

In a potentiated model of signal transduction, dysregulated cell growth is predicted to be accompanied by sensitized differences in the internal signaling states of cells. One key signal transduction network active in cells that are considered progenitors of AML is the Janus kinase/Signal Transducers and Activators of Transcription (STAT) pathway. Stat proteins are important in hematopoietic cytokine receptor signaling pathways that normally regulate cell proliferation, differentiation, and survival. In AML, several reports suggest that STATs, such as Stat3 and Stat5, are involved in oncogenesis are constitutively activated and might be effective targets for therapeutic intervention. A parallel signaling system known to be constitutively activated in some AMLs is the Ras and mitogen activated protein kinase (Ras-MAPK) pathway (involving the MAPK proteins p38 and Erk1/2). In addition to altered basal phosphorylation of key proteins, a potentiated model of signal transduction predicts that cancer cells may have additional signaling changes that cause them to react in an inappropriate or sensitized manner to environmental inputs. Exposure to such environmental inputs could reveal additional measures of difference in the phospho-protein networks that are reflective—either causal or reactive—of the underlying changes required to initiate or sustain the growth of a particular tumor subtype. Therefore, phospho-protein signaling variations among tumors might be employed as markers of differential disease course and response to treatment.

We sought to test whether signaling could be used to classify pathologic differences in leukemic blasts from a well-characterized cohort of 30 adult AML patients. To meet a standard of measuring multiple events simultaneously in a more native context we applied intracellular phospho-specific flow cytometry to detect multiple phosphorylated, activated signaling molecules in primary leukemic cells drawn from these patients. A cytokine response panel, composed of 36 phospho-protein states (6 basal states and 30 cytokine responses), was designed to survey altered signal transduction of tumor cells (FIG. 1a). Each square in the grid approximates a multidimensional flow cytometry file that contained 30,000 cell events. The cytokine responses of each phospho-protein node were compared to the basal state by calculating the log 2 fold difference in median fluorescence intensity (MFI) of stimulated samples divided by unstimulated. Although the data are visually simplified in a response panel, the multiparameter flow cytometry data are available for a detailed inspection of single-cell phospho-protein responses of interesting subsets.

The cytokine response panel included detection of phosphorylated Stat1, Stat3, Stat5, Stat6, p38, and Erk1/2. These proteins provide a survey of the signaling networks that are suspected contributors to leukemogenesis. We collected data on unstimulated cells and cells stimulated for 15 minutes with 20 ng/mL of Flt3 ligand (FL), GM-CSF, G-CSF, IL-3, or IFN-γ. As an example, we applied this panel to the U937 histiocytic lymphoma cell line (FIG. 1a), the HL-60 AML cell line and multiple samples of a CD33+ subset from normal peripheral blood (FIG. 1b). CD33+ cells represent differentiated cells of myeloid lineage and were used to assess variability in cytokine responses among samples from blood donors. In general, the cytokine responses of normal lymphocyte subsets varied very little between donors ($\sigma2<0.1$, n=6) and signaling in cell lines and CD33+ cells reflected previously reported mechanisms of signal transduction4. We then prepared cytokine response grid for six of the 30 AML patient samples (FIG. 1b, AML-P01 through P06). Repeat measurements of cell lines, differentiated cell samples, and AML samples were collected (n≧3) and verified that the technique and monoclonal antibodies displayed a level of reproducibility similar to previous studies. Importantly, however, the response to stimulation highlighted similarities and differences in signaling across patient tumor samples. For example, although AML-P02 and AML-P03 displayed many similarities, AML-P02 responded to GM-CSF and G-CSF through phosphorylation of Stat5 while AML-P03 responded only to GM-CSF (FIG. 1b). Additionally, although most patient samples and controls in this set displayed potent phosphorylation of Stat1 following IFN-g, AML-P05 and AML-P01 lacked this response. We expanded this cytokine response panel to include all 30 AML patients (FIG. 2a) to search for significant similarities and differences among patient responses. Prior studies of AML oncogenesis focused on constitutive signal transduction pathways and worked from the hypothesis that this activation level might be sufficient to monitor the dysregulation of cell signaling status Differences in basal STAT and Ras-MAPK protein phosphorylation were consistent with previous reports showing widespread, varying constitutive activity of signaling pathways in AML.

However, in support of the hypothesis that differences in underlying tumour mutations might lead to difference in potentiated signaling, phosphoprotein responses in many of the primary AML blasts showed considerable induction and variance of STAT and RAS/MAP-K pathway member phosphorylation (FIG. 2a,b). In addition to the six basal phosphorylation states, we identified seven of the thirty cytokine response states that displayed significant variance across AML patient samples ($\sigma2>0.1$, FIG. 2b, highlighted in yellow). These were: (i) phosphorylation of Stat3 following G-CSF, (ii-v) phosphorylation of Stat5 following GM-CSF, G-CSF, IL-3, and IFN-γ, (vi) Stat1 phosphorylation following IFN-γ, and (vii) phosphorylation of Erk1/2 following FL. Remaining tumor cytokine responses displayed variation at or less than the variance in normal, differentiated CD33+ cells and the two closest node states to the significance threshold did not affect subsequent patient groupings. A graph of the absolute median against the variance indicates the signal to noise threshold and the relationship of variance to the median basal state or cytokine response (FIG. 2c).

Based on the potentiated signaling hypothesis, we predicted that these 13 phospho-protein states represented underlying oncogenic events required to initiate or sustain differential tumor pathology and could be used to stratify patient risk. We composed a signal transduction based classification for AML using unsupervised clustering of these phospho-protein biosignatures. When patients are clustered according to a biological hypothesis and then subsequently tested for correlation to clinical parameters—as opposed to pre-grouping patients by clinical outcome and then testing each node state as a hypotheses—the statistical perils of multiple t-tests can be avoided. This method also allows for disease subgroups to be identified even when normal control cells are rare or difficult to obtain in bulk, as is the case with myeloid progenitor cells, because differences among experimental samples are used to define groups rather than comparison of each sample to a proposed normal control.

To group biosignatures by similarity (FIG. 3a) we employed the complete linkage hierarchical clustering algorithm available in Multiple Experiment Viewer (MeV) http(colon)//www(dot)tigr(dot)org/software/tm4/mev(dot)html). Similarity grouping identified four main clusters of AML patients (FIG. 3b). Each of these was termed a Signaling Cluster (SC) and was referred to based on the primary signaling profile of the cluster: (i) SC-NP displayed little or no potentiated cytokine responses and had varied basal phosphorylation (underlined letters denote the cognate acronym), (ii) SC-PB displayed both potentiated cytokine responses and high basal phospho-protein states, (iii) SC-P1 displayed intense potentiated signaling, low basal phosphorylation, and a p-Stat1 response to IFN-γ, and (iv) SC-P2 displayed many potentiated cytokine responses in the context of low basal phosphorylation.

To test the potentiated signaling hypothesis we asked whether clinical factors previously determined to be prognostic for AML correlated significantly with the biosignature-derived SCs (FIG. 3b). Resistance to course 1 chemotherapy—cytarabine plus an anthracycline given to patients healthy enough to withstand associated cytotoxicity—correlated significantly with SC-P2 (p=0.002, FIG. 3b). Patients in SC-P2 constituted 33% of this cohort (10/30). This finding demonstrates that signal transduction based classification of human cancer, a priori of knowledge of clinical outcome, can produce a patient classification that is predictive of response to therapy.

One genetic change we predicted might potentiate pre-existing myeloid signaling networks was mutation of the Flt3 receptor tyrosine kinase. Abnormalities of Flt3 are detected in approximately 30% of AML patients and are well-established as a negative prognostic indicator in AML11,12.

Experiments in cell lines have suggested that expression of mutant Flt3 gives rise to constitutive Stat5 and Ras-MAPK activity, however this connection was not observed in previously published comparisons of basal Stat5 phosphorylation in Flt3 mutant and wild type patient-derived primary AML blasts27.

Notably, the AML patient samples that displayed high myeloid cytokine responses contained internal tandem duplication of Flt3—whereas the samples with a non-potentiated SC profile lacked these mutations (p=0.02). Of patients with Flt3 mutations that do not cluster in SC-P2, 4/7 showed other mutations including either Asp835 Flt3 mutation or N-Ras mutations (data not shown). As reported by others, we observed no significant difference in the basal phosphorylation of Stat5 in either normal or Flt3-mutant AML patients (FIG. 4a).

Potentiated signaling of Stat5 and, to a lesser extent, Stat3 was common in the AML patient groups displaying Flt3 mutations. Phosphorylation of Stat5 following GM-CSF and G-CSF was significantly potentiated in patients with Flt3 mutations (p=0.04 and 0.02, respectively, FIG. 4a and FIG. 4b). It is notable that Stat3 phosphorylation following G-CSF (which was the only Stat3 biosignature state displaying significant variance among AMLs) also correlated with Flt3 mutation (p=0.01, FIG. 4a and FIG. 4b). To represent the effect of Flt3 mutation on myeloid signal transduction nodes we summed the four cytokine response node states (p-Stat3 following G-CSF, and p-Stat5 following GM-CSF, G-CSF, and IL-3) and graphed the correlation between the myeloid cytokine response and Flt3 mutation in AML patient samples. We observe a striking correlation that strongly support the notion that Flt3 mutations potentiate signaling through pre-existing potentiated pathways in AML (p=0.005, FIG. 4a). This might indicate patients displaying potentiated myeloid signal transduction, and especially those with the profile of SC-P2, might respond well to therapies involving STAT pathway inhibitors.

Additionally, these data suggest that each SC grouping reflects proliferative advantages required for leukemogenesis that, when combined with other genomic and proteomic changes, produced common signatures in the mitogenic signaling network of leukemic cells. Correlation of six cell surface antigens with SC groups or Flt3 identified the unexpected loss of the CD15/Lewis X as significantly correlated with SC-P2 and Flt3 mutation ($\chi^2$ test indicated p=0.03 and p<0.001, respectively, FIG. 3b).

The profile of SC-NP, which included 36.7% of patients (11/30), was comprised primarily by low to no cytokine response and low phosphorylation of Stat1 following IFN-γ (FIG. 3a). Additional responses associated with this group were low Stat5 phosphorylation following IL-3 and low Stat3 phosphorylation following G-CSF, both of which are the opposite of changes observed in SC-P2. Interestingly, in SC-NP there were cytogenetic alterations 10 that fell into a closely related branch (FIG. 3a, hierarchy branch AML-P23 through AML-P30) containing two patients with a 9;11 translocation (AML-P27 and AML-P24) and two patients with a loss of chromosome 5 (AML-P23 and AML-P17). Patients with no detectable cytogenetic alterations formed a closely related branch of SC-P1 (FIG. 3a, hierarchy branch AML-P13 through AML-P20). The division of altered or diploid cytogenetics among branches of SC-NP and SC-P1 was statistically significant (p<0.001). The only other patient with a 9;11 translocation, AML-P03, contained an Asp835 mutation of Flt3 and was profiled as SC-PB. AML-P26, which displayed an SC-NP profile, was the sole patient in this cohort where a copy of chromosome 17, the locus of Stat5 and Stat3, had been lost.

A critical advantage of single cell based biosignatures is that, as shown above, they approximate complex data well enough to allow biologically significant clustering while retaining the underlying flow data for further examination. In addition to validating controls and comparing the magnitude of responses, we examined the original flow cytometry histograms and 2D plots and found that higher dimensional representations of the data identified subsets of cells with unique features. For instance, the 2D contour plots for the GM-CSF and G-CSF response of Stat5 and Stat3 are shown grouped by Flt3 mutational status for 10 representative AML patient samples (FIG. 4b). Note that although Stat3 and Stat5 are both thought to be constitutively active in leukemia and share many structural similarities, Flt3 mutation correlated with potentiated Stat5 phosphorylation following GM-CSF but had no relationship to Stat3 phosphorylation (top row). In contrast, in most cases Flt3 mutation appeared to correlate with potentiation of both the p-Stat5/G-CSF node and the p-Stat3/G-CSF node in individual primary AML blast cells (bottom row). This suggests strongly that Flt3 mutation can, in significant subset(s) of cells as observed in two dimensional flow cytometry, lead to unexpected co-activation of important phospho-protein transcription factors.

Phospho-protein signaling of blast cells from AML-P05 were classified by MeV software as having a profile similar to SC-NP despite the detection of Flt3 mutation. The presence of a defined subset of AML-P05 blast cells with p-Stat5 and p-Stat3 potentiation similar to the profile of SC-P2 was surprising and suggests that some cells may have acquired additional mutations leading to altered signaling (FIG. 4b). AML-P05, like all other patients with Flt3-ITD and a non-SC-P2 profile, went into remission following course 1 chemotherapy ($p<0.001$, FIG. 3b). In addition, the well recognized limitation to classification of tumour micro-heterogeneity might be overcome using multi-parameter approaches that distinguish tumor cell subset responses to input stimuli. Extraction of high dimensional information could be applied to further refine our understanding of systems such as that presented here, especially when additional phospho-proteins or other single cell events are measured simultaneously. Whether these subset differences represent simply non-responsive cells, cancer 'stem' cells2, or other stages of clonal evolution within the tumour remains to be determined.

The mechanism-based classification of AML reported here indicates that the phospho-proteome can be informative of tumor pathology. In addition, the cytokine response approach demonstrated could readily be applied to fields outside cancer research. By provoking cell populations to respond to external stimuli, one can distinguish differences in underlying signaling pathologies and thereby classify patient populations. In this regard it was striking that AML blasts responded to cytokine stimulation as they are commonly thought of as having constitutively active STAT and Ras-MAPK signaling. The finding that potentiated cytokine responses of these tumors can be combined with information on basal phosphorylation states and clustered to create a classification with clinical relevance will be important for clinical groups designing and testing mechanism based cancer therapies. The results suggest that patient chemotherapy regimes, including kinase inhibitors or other therapeutics, might be tailored for and directed to specific cell subsets within biosignature-defined patient response groups.

Materials and Methods

Patients and Preparation of AML Blasts.

The study was approved by the local Ethics Committee and samples collected after informed consent. Samples were selected from a large group of consecutive patients with de novo AML and high peripheral blood blast counts 20. These patients were admitted to the hospital from April 1999 to August 2003, the median age was 60 and ages ranged from 29 to 84. As these patients were selected for high blast counts, enriched AML cell populations were prepared using a simple density gradient separation of peripheral blood samples (Ficoll-Hypaque; NyCoMed, Oslo, Norway; specific density 1.077) before safe, standardized cryopreservation according to previously developed techniques 28. These patients represent the latter portion of a group studied previously for Flt3 signaling and mutation in AML20. The acute myeloid leukemia cell line HL-60 and the monocytoid lymphoma cell line U-937 was from American Type Culture Collection (www(dot)atcc(dot)ord) and cultured in RPMI medium (Invitrogen, Carlsbad, Calif., USA)+10% Fetal Calf Serum (HyClone, South Logan, Utah, USA).

Stimulation of AML Blasts.

Peripheral blood containing >95% AML blasts was thawed into 5 mL Stem Span H3000 defined, serum free medium (Stem Cell Technologies, Vancouver, BC, Canada), counted, and resuspended at 2×106 cells per mL. Six FACS tubes (Falcon 2052, BD-Biosciences, San Jose, Calif.) were then filled with 2 mL of each leukemia sample and allowed to rest at 37° C. for 2 h. AML blasts were resuspended gently to prevent aggregation and allowed to rest at 37° C. for another 45 minutes. At this time vehicle (deficient RPMI medium, Invitrogen, Carlsbad, Calif.) or 40 µL of stimulus was added to each tube to a final concentration of 20 ng/mL. Stimuli included human recombinant Flt3 ligand (FL), GM-CSF, G-CSF, IL-3, and IFN-γ (all cytokines from Peprotech, Inc., Rocky Hill, N.J., USA). Samples were returned to the 37° C. incubator for 15 minutes to allow signal transduction and phosphorylation, after which 100 µL of 32% para-formaldehyde (PFA, Electron Microscopy Services Fort Washington, Pa., USA) was added to each 2 mL tube of cells to a final concentration of 1.6%. Cells were fixed for 15 minutes at room temperature, permeabilized by resuspension in 2 mL ice cold methanol for 10 minutes, and stored at 4° C. until being stained for flow cytometry.

Intracellular Phospho-Specific Flow Cytometry.

PFA fixed, methanol permeabilized AML blasts were rehydrated by adding 2 mL phosphate buffered saline (PBS), gentle resuspension, and then centrifugation. The cell pellet was washed once with 2 mL PBS, resuspended in 150 µL PBS+0.1% BSA (Sigma, St. Louis, Mo., USA), and split evenly into three new FACS tubes. 50 µL of an antibody mix containing 0.065 µg primary conjugated phospho-specific antibody per sample was added to each tube of AML blasts and staining proceeded for 20 minutes at room temperature. Alexa (Ax) dye (Molecular Probes, Eugene, Oreg., USA) coupled primary conjugated antibodies (all from BD-Pharmingen, San Diego, Calif., USA) included antibodies against phospho-Stat3(Y705)-Ax488, phospho-Stat5(Y694)-Ax647, phospho-Stat6(Y641)-Ax488, phospho-Stat1(Y701)-Ax647, phospho-p38(T180/Y182)-Ax488, and phospho-Erk1/2(T202/Y204)-Ax647 and were applied in pairs (Stat5/Stat3, Stat1/Stat6, and Erk/p38) for subsequent detection of Alexa-488 and Alexa 647 (Molecular Probes, Eugene, Oreg.) on FL-1 and FL-4, respectively. Stained AML blasts were then washed by adding 2 mL PBS+0.1% BSA and resuspended in a final volume of 200 µL PBS. Approximately 30,000 ungated events were collected for each sample on a benchtop FACSCalibur dual-laser cytometer (Becton Dickinson, Franklin Lakes, N.J., USA). When employed to detect cells of myeloid lineage in normal PBL, antibodies against CD33 were phycoerythrin conjugated (clone WM53, BD-Pharmingen, San Diego, Calif., USA) and detected on FL-2.

Statistical Analysis.

Changes in phosphorylation of STAT and Ras-MAPK proteins following cytokine stimulation were approximated by calculating the $\log_2$ fold median fluorescence index (MFI) of stimulated over unstimulated cell populations. Differences in basal phosphorylation were compared by calculating the log 2 fold MFI of a sample over the minimum among tumors. To determine the statistical significance of observed versus expected distributions we used a $\chi^2$ test (FIG. 3b), and to determine the significance of the difference in mean of two populations we used a student's t-test ($\alpha=0.05$, FIG. 4a). Standard t-tests were used to validate existing hypotheses.

Example 3

The following example employs the methods and compositions of the instant invention to generate and analyze potentiation data based on exposure to a specific drug.

Initial patient samples, including five collections from each of twelve patients (total 60 samples), are aliquoted into 96-well plates to accommodate the cytokine responses panel shown in Table 1. Each 96 well plate then be stained with either the 4-color or 6-color antibody cocktails detailed in Table 2.

In addition to the patient samples, 3 cell lines (U937, HL60, MV411) are employed for in vitro drug investigation. The cell lines are individually treated with drug at 5 time points (1 hr, 2, hr, 4 hr, 12 hr, 24 hr) prior to cytokine stimulation. The resulting 15 samples are aliquoted into 96-well plates and stained as described above.

Finally, collections from six normal blood donors are processed as "control" samples. These control samples include five collections from each of the six donors and are processed identically to the initial patient samples. In addition, five collections from each of the six donors are processed identically as the three cell lines employed in the in vitro drug investigation.

Flow cytometric data is collected for each of the fully processed samples and analyzed via bioinformatics tools described above and statistical significance analysis is generated based in the processed flow data.

TABLE 1

Generalized protocol for study of potentiation.

1) Cells are suspended in a small volume of serum free H3000 stem span media.
2) Cells are counted. A minimum of 20 million viable cells from each should be present in the sample (for four core stains), plus 5 million for each stored sample.
3) Cells are diluted to $6.2 \times 10^5$ cells/100 uL, and 100 uL of each is aliquoted into a 96-well plate, as shown below (Experimental Layout).
4) Stimulations are added at 10 ng/mL into the colums of cells. Stimulation progresses for 15 minutes at 37° C.
5) To end stimulation, cells are fixed by adding 10 uL 32% PFA to each well (5 min at room temperature).
6) Cells are pelleted and resuspended in methanol to permeabilize. Cells can be stored at this point for 3-6 weeks, or stained with labeled antibodies and analyzed right away.
7) The response panel is approximated in a two dimensional array of nodes (in rows) and states (in columns), similar to the experimental layout. Typically, the $\log_2$ of [MFI stimulated/MFI unstimulated] is taken. For basal nodes, the $\log_2$ of [MFI basal x/MFI tumor sample minimum basal] can be used to place measurements on the same scale.
8) To identify a biosignature, the node states for all tumor samples are collected and the variance across tumors studied. For multiple drug timepoints, each timepoint of a sample is treated as a separate sample. Those node states with variance greater than that seen in a normal cell are typically included in the biosignature.
9) Unsupervised clustering of biosignature node states is used to group samples.
10) Distribution of clinical parameters in resulting groups is determined using statistical significance testing (Chi Squared and Student's t-test on previously defined hypotheses).
11) Groups of patient samples with similar potentiation are given designations.
12) Pathway maps, based on all possible pathway interactions observed, are highlighted and dimmed according to observations of each group. In general, if more than half the samples in the group display potentiation above the median for all samples, then that pathway is highlighted. Otherwise, the pathway is dimmed.
13) Pathway maps can be built out for individual patients based on their observed potentiation, and based on these maps a patient sample can be phenotyped as belonging to a group (and will be predicted to have similar clinical outcome as that group).
14) A predictive panel for the disease is made, composed of biosignature node states, and validated on an additional set of patient samples similar to the original. This panel is minimized and optimized to be as accurate as possible with as few as possible node state measurements for a given sample.

TABLE 2

96 well experimental response panel layout for potentiation example using one sample (corresponding to a patient sample taken at a drug treatment timepoint).

|  | Unstim. (basal) 1 | TGFβ 2 | IL-3 3 | Flt3 ligand 4 | GM-CFS 5 | G-CSF 6 | IFNγ 7 |
|---|---|---|---|---|---|---|---|
| Stain 1 | a | a1 | a2 | a3 | a4 | a5 | a6 | a7 |
| Stain 2 | b | b1 | b2 | b3 | b4 | b5 | b6 | b7 |
| Stain 3 | c | c1 | c2 | c3 | c4 | c5 | c6 | c7 |
| Stain 4 | d | d1 | d2 | d3 | d4 | d5 | d6 | d7 |
| Bank | e | e1 | e2 | e3 | e4 | e5 | e6 | e7 |
| Bank | f | f1 | f2 | f3 | f4 | f5 | f6 | f7 |
| Bank | g | g1 | g2 | g3 | g4 | g5 | g6 | g7 |

Colored rows will be stained for analysis, grey rows, cell numbers permitting, could be banked in methanol for future study.
Banked samples could be used for genetic analysis, staining other targets, or repeat/control stainings.
Designations a1-g7 refer to 96 well plate coordinates.

TABLE 3

4-color and 6-color Stains

|  | Stain 1 | Stain 2 | Stain 3 | Stain 4 |
|---|---|---|---|---|
| 4-color | pstat1(Y701)-AX488<br>pstat3(Y705)-pe<br>pstat6(Y694)-AX647<br>CD33-percpcy5.5 | pstat5(Y694)-AX488<br>p-erk1/2-PE<br>p-p38-AX647<br>CD33-percpcy5.5 | p-flt3-AX488<br>pstat4(Y693)-AX546<br>pstat3(S727)-AX647<br>CD33-percpcy5.5 | p-Flt3-AX488<br>p-erk1/2-PE<br>pstat5(Y694)-AX647<br>CD33-percpcy5.5 |
| 6-color | pstat1(Y701)-AX488<br>pstat3(Y705)-pe<br>pstat6(Y694)-AX647<br>CD33-percpcy5.5<br>CD38-PeCy7<br>CD14-APCCy7<br>TRUCOUNT BEADS | pstat5(Y694)-AX488<br>p-erk1/2-PE<br>p-p38-AX647<br>CD33-percpcy5.5<br>CD38-PeCy7<br>CD14-APCCy7<br>TRUCOUNT BEADS | p-Flt3-AX488<br>pstat4(Y693)-AX546<br>pstat3(S727)-AX647<br>CD33-percpcy5.5<br>CD38-PeCy7<br>CD14-APCCy7<br>TRUCOUNT BEADS | P-Flt3-AX488<br>p-erk1/2-PE<br>pstat5(Y694)-AX647<br>CD33-percpcy5.5<br>CD38-PeCy7<br>CD14-APCCy7<br>TRUCOUNT BEADS |

We claim:

1. A method of determining a phenotype of an individual from whom a first cell population has been obtained, said method comprising:
   determining signaling node states of a plurality of signaling nodes in one or more cells of a first cell population;
   comparing said signaling node states of said plurality of signaling nodes in said first cell population with signaling node states of said plurality of signaling nodes in at least a second cell population or data representing said signaling node states of said plurality of signaling nodes in said second cell population, wherein said compared signaling node states are states that have been determined under culture conditions comprising: (i) a presence of a same potentiator or a fragment thereof, or (ii) a presence of no potentiator, wherein said compared signaling node states are determined by a method comprising:
   contacting each of said cell populations with at least one distinguishably detectable state-specific binding element for each of said signaling node states of said plurality of signaling nodes; and
   detecting a level of binding of each of said distinguishably detectable state-specific binding element for each of said signaling node states of each of said plurality of signaling nodes in each of said cell populations; and
   determining a phenotype of said individual based on said comparison.

2. The method according to claim 1, wherein said potentiator is selected from the group consisting of cytokines, interleukins, hormones, bioactive agents, receptor ligands, cells, and therapeutic agents.

3. The method of claim 1 wherein said detecting is by flow cytometry.

4. The method according to claim 3, wherein said comparing step comprises analysis of flow cytometric data obtained in said determining signaling node states step.

5. The method according to claim 3, wherein said flow cytometric data is selected from the group consisting of mean fluorescent intensity (MFI) and cell population size.

6. The method according to claim 5, wherein said compared signaling node states creates data, and wherein said data is the $\log_2$ fold change in MFI as compared to a control MFI value.

7. The method according to claim 6, wherein said control MFI value is the MFI value of the basal node state of each of said signaling nodes.

8. The method according to claim 7, wherein said control MFI value is the MFI value of a node state of a control cell population.

9. The method according to claim 1, wherein said plurality of signaling node states of said first cell population is compared to a plurality of signaling node states from a plurality of distinct cell populations.

10. The method according to claim 9, wherein said comparing step comprises calculating the variance of said compared signaling node state.

11. The method according to claim 10, further comprises a profiling step, wherein said profiling step comprises clustering said first cell population and said plurality of distinct cell populations based on said signaling node data when said variance is above a threshold level.

12. The method according to claim 11, wherein said clustering is performed using a clustering algorithm.

13. The method according to claim 12, wherein said clustering algorithm is unsupervised.

14. The method according to claim 11, wherein said clustering is based at least in part on cell population meta-level data.

15. The method according to claim 14, wherein said meta-level data is selected from the group consisting of tissue type, degree of differentiation, proliferation index, metastatic spread, genotype, phenotype, disease diagnosis, drug susceptibility, drug resistance, subject status and treatment regimen.

16. The method according to claim 11, wherein at least one other cellular parameter in said first population and said plurality of distinct cell populations is correlated with said clusters using statistical significance testing.

17. The method according to claim 16, wherein said at least one other parameter is selected from the group consisting of tissue type, degree of differentiation, proliferation index, metastatic spread, genotype, phenotype, disease diagnosis, drug susceptibility, drug resistance, subject status and treatment regimen.

18. The method according to claim 9, wherein said plurality of distinct cell populations comprise a phenotype and wherein said phenotype is a known phenotype.

19. The method according to claim 18, wherein said known phenotype is a disease state.

20. The method according to claim 19, wherein said disease state is selected from the group consisting of cancer, autoimmunity, infectious disease, and genetic disease.

21. The method according to claim 9, wherein said plurality of distinct cell populations comprises cell populations of unknown phenotype.

22. The method according to claim 1, wherein the first cell population is derived from an individual, and wherein said determined phenotype of said first cell population is further used in a step selected from the group consisting of: predicting or diagnosing a disease state, targeting a disease therapy, monitoring treatment of a disease state, diagnosing a therapeutic response, identifying molecular targets for pharmacological intervention, and making determinations such as prognosis, disease progression, response to particular drugs and to stratify patient risk.

23. The method of claim 22 wherein the individual is an animal.

24. The method of claim 22 wherein the individual is a mammal.

25. The method of claim 22 wherein the individual is a human.

26. The method of claim 22 further comprising obtaining a result from said step selected from the group consisting of: predicting or diagnosing a disease state, targeting a disease therapy, monitoring treatment of a disease state, diagnosing a therapeutic response, identifying molecular targets for pharmacological intervention, and making determinations such as prognosis, disease progression, response to particular drugs and to stratify patient risk; and communicating to the individual said result of said step.

27. The method of claim 22 wherein said determined phenotype of said first cell population is further used in predicting or diagnosing a disease state, and wherein the method further comprises targeting a disease therapy for said predicted or diagnosed disease state.

28. The method of claim 1, wherein said phenotype from said individual is selected from the group consisting of a disease state, responder to treatment, and non-responder to treatment.

29. A method of determining a phenotype of an individual from whom a first cell population has been obtained, said method comprising:
  contacting said first cell population with at least two distinct potentiators in separate cultures;
  determining signaling node states of a plurality of signaling nodes in one or more cells from each of said separate cultures, comprising:
  contacting said one or more cells from each of said separate cultures with at least one distinguishably detectable state-specific binding element for each of said signaling node states of said plurality of signaling nodes; and
  detecting a level of binding of each of said distinguishably detectable state-specific binding element for each of said signaling node states of each of said plurality of signaling nodes in each of said separate cultures;
  creating a response panel of said first cell population comprising said determined signaling node states of said plurality of signaling nodes;
  comparing said response panel of said first cell population with a response panel of a second cell population; and
  determining a phenotype of said individual based on said comparison.

\* \* \* \* \*